US011072607B2

(12) United States Patent
Patel et al.

(10) Patent No.: US 11,072,607 B2
(45) Date of Patent: Jul. 27, 2021

(54) INHIBITORS OF RIP1 KINASE AND METHODS OF USE THEREOF

(71) Applicant: Genentech, Inc., South San Francisco, CA (US)

(72) Inventors: Snahel Patel, Foster City, CA (US); Gregory Hamilton, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/839,788

(22) Filed: Dec. 12, 2017

(65) Prior Publication Data
US 2018/0170927 A1  Jun. 21, 2018

Related U.S. Application Data

(60) Provisional application No. 62/435,567, filed on Dec. 16, 2016.

(51) Int. Cl.
| | | |
|---|---|---|
| *A61K 31/553* | (2006.01) | |
| *A61K 31/55* | (2006.01) | |
| *A61K 31/551* | (2006.01) | |
| *C07D 487/04* | (2006.01) | |
| *C07D 471/04* | (2006.01) | |
| *C07D 498/04* | (2006.01) | |
| *C07D 519/00* | (2006.01) | |
| *A61P 29/00* | (2006.01) | |
| *A61P 17/06* | (2006.01) | |
| *A61P 9/10* | (2006.01) | |
| *A61P 1/16* | (2006.01) | |
| *A61P 1/18* | (2006.01) | |
| *A61P 13/12* | (2006.01) | |
| *A61P 1/00* | (2006.01) | |
| *A61P 11/00* | (2006.01) | |
| *A61P 25/00* | (2006.01) | |
| *A61P 1/04* | (2006.01) | |

(52) U.S. Cl.
CPC .............. *C07D 471/04* (2013.01); *A61P 1/00* (2018.01); *A61P 1/04* (2018.01); *A61P 1/16* (2018.01); *A61P 1/18* (2018.01); *A61P 9/10* (2018.01); *A61P 11/00* (2018.01); *A61P 13/12* (2018.01); *A61P 17/06* (2018.01); *A61P 25/00* (2018.01); *A61P 29/00* (2018.01); *C07D 487/04* (2013.01); *C07D 498/04* (2013.01); *C07D 519/00* (2013.01)

(58) Field of Classification Search
CPC .... A61K 31/553; A61K 31/55; A61K 31/551; C07D 487/04; C07D 471/04; C07D 498/04

See application file for complete search history.

(56) References Cited

U.S. PATENT DOCUMENTS

| | | | |
|---|---|---|---|
| 5,206,234 A | 4/1993 | Bock et al. | |
| 6,350,741 B1 | 2/2002 | Golec et al. | |
| 9,815,850 B2 * | 11/2017 | Estrada | ................ C07D 261/18 |
| 2004/0002495 A1 | 1/2004 | Sher et al. | |
| 2011/0038877 A1 | 2/2011 | Way et al. | |
| 2017/0008877 A1 | 1/2017 | Patel et al. | |
| 2019/0241565 A1 | 8/2019 | Patel | |

FOREIGN PATENT DOCUMENTS

| | | |
|---|---|---|
| EP | 3318267 A1 | 5/2018 |
| WO | 02/20530 A1 | 3/2002 |
| WO | 03/046222 A1 | 6/2003 |
| WO | 2004/037986 A2 | 5/2004 |
| WO | 2006/031606 A2 | 6/2006 |
| WO | 2008/011190 A1 | 1/2008 |
| WO | 2009/140128 A2 | 11/2009 |
| WO | 2013/059791 A2 | 4/2013 |
| WO | 2014/009495 A1 | 1/2014 |
| WO | 2014/023708 A1 | 2/2014 |
| WO | 2014/125444 A1 | 8/2014 |
| WO | 2014/145022 A1 | 9/2014 |
| WO | 2014/170892 A1 | 10/2014 |
| WO | 2016/027253 A1 | 2/2016 |
| WO | 2017/001645 A1 | 1/2017 |
| WO | 2017/001660 A1 | 1/2017 |
| WO | 2017/004500 A1 | 1/2017 |
| WO | 2017001655 A1 | 1/2017 |
| WO | 2017/096301 A1 | 6/2017 |
| WO | 2017/103851 A1 | 6/2017 |
| WO | 2017/109724 A1 | 6/2017 |
| WO | 2017/112815 A1 | 6/2017 |
| WO | 2017/136727 A2 | 8/2017 |
| WO | 2018/073193 A1 | 4/2018 |
| WO | 2018/109097 A1 | 6/2018 |
| WO | 2019/204537 A1 | 10/2019 |

OTHER PUBLICATIONS

Bertrand et al., "cIAP1 and cIAP2 facilitate cancer cell survival by functioning as E3 ligases that promote RIP1 ubiquitination" Mol Cell 30(6):689-700 (Jun. 2008).
Chen, "Ubiquitination in signaling to and activation of IKK" Immunol Rev. 246(1):95-106 ( 2012).
Cho et al., "Phosphorylation-driven assembly of the RIP1-RIP3 complex regulates programmed necrosis and virus-induced inflammation" Cell 137(6):1112-23 (Jun. 2009).
De Almagro, "Necroptosis: Pathway diversity and characteristics" Semin Cell Dev Biol. 39:56-62 (Mar. 2015).
Degterev et al., "Chemical inhibitor of nonapoptotic cell death with therapeutic potential for ischemic brain injury" Nat Chem Biol. 1(2):112-9 (Jul. 2005).
Degterev et al., "Identification of RIP1 kinase as a specific cellular target of necrostatins" Nat Chem Biol. 4(5):313-21 (May 2008).
Feoktistova et al., "cIAPs block Ripoptosome formation, a RIP1/caspase-8 containing intracellular cell death complex differentially regulated by cFLIP isoforms" Mol Cell. 43(3):449-63 (Aug. 2011).

(Continued)

*Primary Examiner* — Brenda L Coleman
(74) *Attorney, Agent, or Firm* — Andre T. Krammer

(57) ABSTRACT

The invention provides novel compounds having RIP1 kinase inhibitory activity, pharmaceutical compositions including the compounds and methods of using the compounds.

3 Claims, No Drawings

(56) References Cited

OTHER PUBLICATIONS

Harris et al., "Discovery of Small Molecule RIP1 Kinase Inhibitors for the Treatment of Pathologies Associated with Necroptosis" ACS Medicinal Chemistry Letters 4(12):1238-1243 ( 2013).
He et al., "Receptor interacting protein kinase-3 determines cellular necrotic response to TNF-alpha" Cell 137(6):1100-11 (Jun. 2009).
ISR for PCT/EP2017/082851, 2018.
Kaiser et al., "Toll-like receptor 3-mediated necrosis via TRIF, RIP3, and MLKL" J Biol Chem. 288(43):31268-79 (Oct. 2013).
Linkermann et al., "Necroptosis" N Engl J Med. (Send to), 370(5):455-65 (Jan. 2014).
Najjar et al., "Structure Guided Design of Potent and Selective Ponatinib-Based Hybrid Inhibitors for RIPKI" Cell Rep. 10(11):1850-60 (Mar. 24, 2015).
Newton et al., "Activity of protein kinase RIPK3 determines whether cells die by necroptosis or apoptosis" Science 343(6177):1357-60 (Mar. 2014).
Newton, "RIPK1 and RIPK3: critical regulators of inflammation and cell death" Trends Cell Biol. 25(6):347-5 (Jun. 2015).
O'Donnell et al., "Ubiquitination of RIP1 regulates an NF-kappaB-independent cell-death switch in TNF signaling" Curr Biol. 17(5):418-24 (Mar. 2007).
Sun et al., "Mixed lineage kinase domain-like protein mediates necrosis signaling downstream of RIP3 kinase" Cell 148(1-2):213-27 (Jan. 2012).
Takahashi et al., "Necrostatin-1 analogues: critical issues on the specificity, activity and in vivo use in experimental disease models" Cell Death Dis, (Send to), 3:e43 (Nov. 2012).
Vanden et al., "Regulated necrosis: the expanding network of non-apoptotic cell death pathways" Nature Reviews Molecular Cell Biology 15:135-147, 2014.
Wang et al., "TNF-alpha induces two distinct caspase-8 activation pathways" Cell 133(4):693-703 (May 2008).
Zhao et al., "Mixed lineage kinase domain-like is a key receptor interacting protein 3 downstream component of TNF-induced necrosis" Proc Natl Acad Sci U S A. 109(14):5322-27 (Apr. 2012).
Harris et al., "Discovery of a First-in-Class Receptor Interacting Protein 1 (RIP1) Kinase Specific Clinical Candidate (GSK2982772) for the Treatment of Inflammatory Diseases" Journal of Medicinal Chemistry 60(4):1247-1261 ( 2017).
Written Opinion of the International Searching Authority for PCT/EP2017/082851, dated Jun. 21, 2018.
Hamilton et al., "Potent and selective inhibitors of receptor-interacting protein kinase l that lack an aromatic back pocket group" Bioorganic & Medicinal Chemistry Letters 29(12):1497-1501 ( 2019).
International Search Report and Written Opinion for PCT/EP2017/076385 dated Dec. 7, 2017.
International Search Report and Written Opinion for PCT/US2016/040659 dated Sep. 20 , 2016.
International Search Report and Written Opinion for PCT/US2019/028011 dated Jul. 9 , 2019.
USPTO Non-Final Office Action U.S. Appl. No. 15/200,058, dated Jan. 28, 2020, 6 pages.
USPTO Final Office Action, U.S. Appl. No. 15/200,058, dated Aug. 3, 2018, 12 pages.
Wikipedia, Spiro compound, https://en.wikipedia.org/wiki/Spiro_compound, Jul. 30, 2018, 8 pages.

\* cited by examiner

INHIBITORS OF RIP1 KINASE AND METHODS OF USE THEREOF

CROSS-REFERENCE TO RELATED APPLICATIONS

This application claims priority to U.S. Provisional Patent Application No. 62/435,567, filed Dec. 16, 2016, the entire contents of which are hereby incorporated by reference.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:

1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.

2) Newton, K. (2015) RIPK1 and RIPK3: critical regulators of inflammation and cell death. Trends in cell biology. 25, 347-353.

3) de Almagro, M. C. and Vucic, D. (2015) Necroptosis: Pathway diversity and characteristics. Semin Cell Dev Biol. 39, 56-62.

4) Chen, Z. J. (2012) Ubiquitination in signaling to and activation of IKK. Immunological reviews. 246, 95-106.

5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling Curr Biol. 17, 418-424.

6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.

7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.

8) Wang, L., Du, F. and Wang, X. (2008) TNF-alpha induces two distinct caspase-8 activation pathways. Cell. 133, 693-703.

9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.

10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.

11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.

12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.

13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.

14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.

15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.

16) Linkermann, A. and Green, D. R. (2014) Necroptosis. The New England journal of medicine. 370, 455-465.

17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.

18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.

19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.

20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.

21) International Patent Publication No. WO 2014/125444.

SUMMARY OF THE INVENTION

Provided herein are compounds selected from the group consisting of:
(5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
(4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide;
rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
rac-(5R,7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
(5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
1-(2,2-difluoropropyl)-N-[(3S)-5-methyl-4-oxo-2,3-dihydro-1,5-benzoxazepin-3-yl]pyrazolo[3,4-d]pyrimidine-6-carboxamide;
1-cyclopropyl-N-[(3S)-5-methyl-4-oxo-2,3-dihydro-1,5-benzoxazepin-3-yl]pyrazolo[3,4-d]pyrimidine-6-carboxamide;
(5R)-5-phenyl-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;
(5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;
5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
(5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;
(5S)-5-(2-fluorophenyl)-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;
(5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide;
(4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide;
4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide;
1-(2,2-difluoropropyl)-N-[(3S)-5-methyl-4-oxo-2,3-dihydro-1,5-benzoxazepin-3-yl]pyrazolo[4,3-c]pyridine-6-carboxamide;
1-cyclopropyl-N-[(3S)-5-methyl-4-oxo-2,3-dihydro-1,5-benzoxazepin-3-yl]pyrazolo[4,3-c]pyridine-6-carboxamide;
(7S)-7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
(7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
(5S)-5-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
(5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
(5R,7S)-7-fluoro-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide;
7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide;
7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide;

7-fluoro-5-phenyl-N-[rac-(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide;

7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide;

1-benzyl-N-[(6S)-2,4-dimethyl-5-oxo-7,8-dihydro-6H-pyrazolo[4,3-b]azepin-6-yl]-1,2,4-triazole-3-carboxamide;

1-[(2-fluorophenyl)methyl]-N-[(6S)-1,4-dimethyl-5-oxo-7,8-dihydro-6H-pyrazolo[4,3-b]azepin-6-yl]-1,2,4-triazole-3-carboxamide;

1-benzyl-N-[(6S)-1,4-dimethyl-5-oxo-7,8-dihydro-6H-pyrazolo[4,3-b]azepin-6-yl]-1,2,4-triazole-3-carboxamide;

1-benzyl-N-[rac-(6S)-4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide;

rac-(5S,7S)-7-fluoro-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

rac-(5S,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

rac-(5S,7S)-7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide;

rac-(5R)-7,7-difluoro-5-phenyl-N-[rac-(6S)-2,4-dimethyl-5-oxo-7,8-dihydro-6H-pyrazolo[1,5-a][1,3]diazepin-6-yl]-5,6-dihydropyrrolo[1,2-b][1,2,4]triazole-2-carboxamide;

rac-(5R)-7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide;

rac-(5R)-7,7-difluoro-5-phenyl-N-[rac-(6S)-4-methyl-5-oxo-7,8-dihydro-6H-pyrazolo[1,5-a][1,3]diazepin-6-yl]-5,6-dihydropyrrolo[1,2-b][1,2,4]triazole-2-carboxamide; and 5-(1,1-difluoropropyl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;

or an enantiomer thereof, or a pharmaceutically acceptable salt thereof.

Also provided herein are pharmaceutical compositions comprising a compound provided herein, or a pharmaceutically acceptable salt thereof, and one or more pharmaceutically acceptable carriers or excipients. Specific embodiments include pharmaceutical compositions suitable for intravenous or oral delivery.

Also provided herein are oral formulations of a compound provided herein, or a pharmaceutically acceptable salt thereof, and one or more pharmaceutically acceptable carriers or excipients suitable for oral delivery.

Also provided herein are parenteral formulations of a compound provided herein, or a pharmaceutically acceptable salt thereof, and one or more pharmaceutically acceptable carriers or excipients suitable for parenenteral delivery.

In some embodiments, provided herein are uses of a compound provided herein, or a pharmaceutically acceptable salt thereof, for the treatment of diseases and disorders. In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa and retinal de generation.

In some embodiments, provided herein are methods for the treatment or prevention of a disease or disorder with a therapeutically effective amount of a compound provided herein, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound provided herein or a pharmaceutically acceptable salt thereof.

DETAILED DESCRIPTION OF THE INVENTION

The present invention provides novel compounds selected from the group consisting of:
- (5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- (4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide;
- rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
- rac-(5R,7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- (5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- 1-(2,2-difluoropropyl)-N-[(3S)-5-methyl-4-oxo-2,3-dihydro-1,5-benzoxazepin-3-yl]pyrazolo[3,4-d]pyrimidine-6-carboxamide;
- 1-cyclopropyl-N-[(3S)-5-methyl-4-oxo-2,3-dihydro-1,5-benzoxazepin-3-yl]pyrazolo[3,4-d]pyrimidine-6-carboxamide;
- (5R)-5-phenyl-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;
- (5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;
- 5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
- rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
- (5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;
- (5S)-5-(2-fluorophenyl)-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;
- (5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
- 4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide;
- (4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide;
- 4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide;
- 1-(2,2-difluoropropyl)-N-[(3S)-5-methyl-4-oxo-2,3-dihydro-1,5-benzoxazepin-3-yl]pyrazolo[4,3-c]pyridine-6-carboxamide;
- 1-cyclopropyl-N-[(3S)-5-methyl-4-oxo-2,3-dihydro-1,5-benzoxazepin-3-yl]pyrazolo[4,3-c]pyridine-6-carboxamide;
- (7S)-7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
- (7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
- (5S)-5-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;
- (5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- (5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
- (5R,7S)-7-fluoro-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
- (5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
- 4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide;
- 7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide;
- 7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide;
- 7-fluoro-5-phenyl-N-[rac-(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;
- 7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide;
- 7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
- (7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide;

1-benzyl-N-[(6S)-2,4-dimethyl-5-oxo-7,8-dihydro-6H-pyrazolo[4,3-b]azepin-6-yl]-1,2,4-triazole-3-carboxamide;

1-[(2-fluorophenyl)methyl]-N-[(6S)-1,4-dimethyl-5-oxo-7,8-dihydro-6H-pyrazolo[4,3-b]azepin-6-yl]-1,2,4-triazole-3-carboxamide;

1-benzyl-N-[(6S)-1,4-dimethyl-5-oxo-7,8-dihydro-6H-pyrazolo[4,3-b]azepin-6-yl]-1,2,4-triazole-3-carboxamide;

1-benzyl-N-[rac-(6S)-4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide;

rac-(5S,7S)-7-fluoro-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

rac-(5S,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

rac-(5S,7S)-7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide;

rac-(5R)-7,7-difluoro-5-phenyl-N-[rac-(6S)-2,4-dimethyl-5-oxo-7,8-dihydro-6H-pyrazolo[1,5-a][1,3]diazepin-6-yl]-5,6-dihydropyrrolo[1,2-b][1,2,4]triazole-2-carboxamide;

rac-(5R)-7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide;

rac-(5R)-7,7-difluoro-5-phenyl-N-[rac-(6S)-4-methyl-5-oxo-7,8-dihydro-6H-pyrazolo[1,5-a][1,3]diazepin-6-yl]-5,6-dihydropyrrolo[1,2-b][1,2,4]triazole-2-carboxamide; and 5-(1,1-difluoropropyl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;

or an enantiomer thereof, or a pharmaceutically acceptable salt thereof.

In another embodiment, provided herein is a compound selected from the compounds of Table 1 below.

Also provided herein is a method for the treatment or prophylaxis of a disease or disorder in a human, the method comprising administration to the human of an effective amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

Also provided herein is a method for the treatment of a disease or disorder in a human, the method comprising administration to the human of an effective treatment amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "$\sim$" that intersects a bond in a chemical structure indicates the point of attachment of the bond that the wavy bond intersects in the chemical structure to the remainder of a molecule.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process.

The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds provided herein may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound provided herein is formulated in an acetate buffer, at pH 5. In another embodiment, the compounds provided herein are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound provided herein is administered orally. In other specific embodiments, the compound provided herein is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound provided herein) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention (e.g., compound provided herein) can be prepared. Suitable examples of sustained-release preparations include semipermeable matrices of solid hydrophobic polymers containing a compound provided herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds provided herein may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound provided herein is formulated in an acetate buffer, at pH 5. In another embodiment, the compounds provided herein are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound provided herein) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound provided herein, or pharmaceutically acceptable salt thereof. In a further embodiment includes a pharmaceutical composition comprising a compound provided herein, or a pharmaceutically acceptable salt thereof, together with a pharmaceutically acceptable carrier or excipient.

When the binding target is located in the brain, certain embodiments of the invention provide for a compound provided herein to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound provided herein can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound provided herein across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound provided herein across the blood-brain barrier include, but are not limited to, encapsulating the a compound provided herein in liposomes that are coupled to antibody binding fragments that bind to receptors on the vascular endothelium of the blood-brain barrier (see, e.g., U.S. Patent Publication No. 2002/0025313), and coating a compound provided herein in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound provided herein across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound provided herein with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death. Compounds of the invention are therefore useful for the treatment or prevention of a disease or disorder selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD).

In another embodiment, compounds of the invention are useful for the treatment of one or more symptoms of the above diseases and disorders. In some embodiments, the disease or disorder is an irritable bowel disorder. In some embodiments, the disease or disorder is irritable bowel syndrome (IBS), Crohn's disease, or ulcerative colitis. In some embodiments, the disease or disorder is an ischemia-reperfusion injury of kidneys, liver and lungs. In some embodiments, the disease or disorder is a chronic kidney disease. In some embodiments, the disease or disorder is acute respiratory distress syndrome (ARDS). In some embodiments, the disease or disorder is chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, antiphospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound provided herein, or a pharmaceutically acceptable salt thereof.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound provided herein, or a pharmaceutically acceptable salt thereof.

Also provided herein is a method of treating a disease or disorder in a mammal in need of such treatment, said disease or disorder being selected from the group consisting of irritable bowel disorders (IBD), irritable bowel syndrome (IBS), Crohn's disease, and ulcerative colitis, wherein the method comprises orally administering to said mammal a therapeutically effective amount of a compound provided herein, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound provided herein of the present disclosure.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet), br (broadened), dd (doublet of doublets), dt (doublet of triplets). Coupling constants, when given, are reported in Hz (Hertz).

In the examples below, LCMS methods were performed for 10 or 30 minutes according to the following conditions:

Agilent 10 min LCMS Method: Experiments performed on an Agilent 1290 UHPLC coupled with Agilent MSD (6140) mass spectrometer using ESI as ionization source. The LC separation was using a Phenomenex XB-C18, 1.7 mm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Agilent 30 min LCMS Method: Experiments performed on an Agilent 1100 HPLC coupled with Agilent MSD mass spectrometer using ESI as ionization source. The LC separation was using an Agilent Eclipse XDB-C18, 3.5 mm, 100×3.0 mm column with a 0.7 ml/minute flow rate. Solvent A is water with 0.1% FA and solvent B is acetonitrile with 0.1% FA. The gradient consisted with 2-98% solvent B over 25.5 min and hold 98% B for 2.5 min following equilibration for 1.5 min. UV absorbance were collected at 220 nm and 254 nm and mass spec full scan was applied to all experiment.

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

Abbreviations
ACN Acetonitrile
Boc tert-Butoxycarbonyl
DMF N,N-Dimethylformamide
DMSO Dimethyl sulfoxide
HPLC High Pressure Liquid Chromatography
LCMS Liquid Chromatography Mass Spectrometry
RP Reverse phase
RT or R$_T$ Retention time
SEM 2-(Trimethylsilyl)ethoxymethyl
THF Tetrahydrofuran Example #1

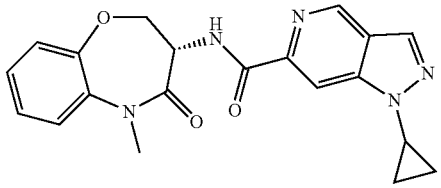 [SMILES: CN1C(=O)[C@@H](NC(=O)c2cc3c(cn2)cnn3C2CC2)COc2ccccc21]

1-cyclopropyl-N-[(3S)-5-methyl-4-oxo-2,3-dihydro-1,5-benzoxazepin-3-yl]pyrazolo[4,3-c]pyridine-6-carboxamide

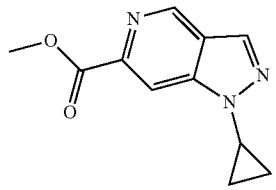 [SMILES: COC(=O)c1cc2c(cn1)cnn2C1CC1]

Step 1: methyl 1-cyclopropyl-1H-pyrazolo[4,3-c]pyridine-6-carboxylate

A mixture of methyl 1H-pyrazolo[4,3-c]pyridine-6-carboxylate (50 mg, 0.28 mmol), 2,2'-bipyridine (44 mg, 0.28 mmol), sodium carbonate (60 mg, 0.56 mmol), cyclopropylboronic acid (48 mg, 0.56 mmol) and copper diacetate (51 mg, 0.28 mmol) in 1,2-dichloroethane (10 mL) was stirred at 70° C. for 4 h. The mixture was poured into water (10 mL) and extracted with dichloromethane (3×20 mL). The combined organic layers were washed with water (20 mL), brine (20 mL), dried over anhydrous sodium sulfate and concentrated under reduced pressure. The residue was purified by preparative TLC (50% ethyl acetate in petroleum ether) to afford methyl 1-cyclopropyl-1H-pyrazolo[4,3-c]pyridine-6-carboxylate (50 mg, 82%) as a yellow oil, used as is in the next step.

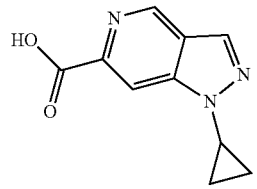 [SMILES: O=C(O)c1cc2c(cn1)cnn2C1CC1]

Step 2: 1-cyclopropyl-1H-pyrazolo[4,3-c]pyridine-6-carboxylic acid

To a solution of methyl 1-cyclopropyl-1H-pyrazolo[4,3-c]pyridine-6-carboxylate (110 mg, 0.5 mmol) in tetrahydrofuran (5 mL) and water (1 mL) was added lithium hydroxide monohydrate (212 mg, 5.1 mmol). The reaction mixture was stirred at 25° C. for 3 h and then concentrated under reduced pressure. The residue was adjusted to pH=5 by additional of hydrochloric acid (2 N). The resulting mixture was extracted with ethyl acetate (3×20 mL). The combined organic layers were washed with water (20 mL), brine (20 mL), dried over anhydrous sodium sulfate and concentrated under reduced pressure to afford crude 1-cyclopropyl-1H-pyrazolo[4,3-c]pyridine-6-carboxylic acid (25 mg, 24%) as a yellow solid, used as is in the next step.

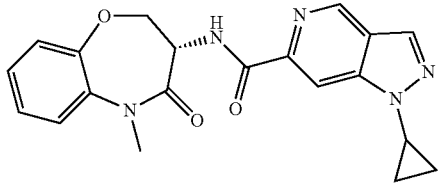 [SMILES: CN1C(=O)[C@@H](NC(=O)c2cc3c(cn2)cnn3C2CC2)COc2ccccc21]

Step 3: 1-cyclopropyl-N-[(3S)-5-methyl-4-oxo-2,3-dihydro-1,5-benzoxazepin-3-yl]pyrazolo[4,3-c]pyridine-6-carboxamide A mixture of 1-cyclopropyl-1H-pyrazolo[4,3-c]pyridine-6-carboxylic acid (25 mg, 0.12 mmol), 1-(3-dimethylaminopropyl)-3-ethylcarbodiimidehydrochloride (28 mg, 0.15 mmol), 1-hydroxybenzotriazole (20 mg, 0.15 mmol) and (S)-3-amino-5-methyl-2,3-dihydrobenzo[b][1,4]oxazepin-4 (5H)-one (28 mg, 0.15 mmol) in N,N-dimethylformamide (4 mL) was stirred at 25° C. for 16 h and then concentrated under reduced pressure. The residue was purified by RP-HPLC (acetonitrile 30-60%/0.05% ammonium hydroxide in water) to afford 1-cyclopropyl-N-[(3S)-5-methyl-4-oxo-2,3-dihydro-1,5-benzoxazepin-3-yl]pyrazolo[4,3-c]pyridine-6-carboxamide (8.7 mg, 19%) as a white solid. $^1$H NMR (400 MHz, CD$_3$OD) δ 9.10 (s, 1H), 8.34 (s, 1H), 8.26 (s, 1H), 7.49-7.42 (m, 1H), 7.38-7.30 (m, 2H), 7.28-7.23 (m, 1H), 5.10-5.05 (m, 1H), 4.74-4.67 (m, 1H), 4.45-4.42 (m, 1H), 3.79-3.76 (m, 1H), 3.44 (s, 3H), 1.24-1.21 (m, 4H). LCMS R$_T$=0.822 min, m/z=378.0 [M+H]$^+$.

LCMS (5 to 95% acetonitrile in water+0.03% trifluoacetic acid over 1.5 mins) retention time: 0.822 min, ESI+ found [M+H]=378.0.

Example #2

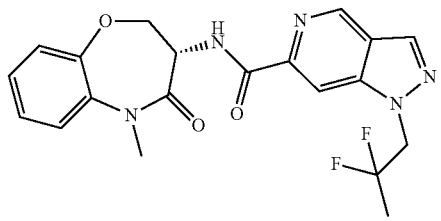 [SMILES: CN1C(=O)[C@@H](NC(=O)c2cc3c(cn2)cnn3CC(C)(F)F)COc2ccccc21]

1-(2,2-difluoropropyl)-N-[(3S)-5-methyl-4-oxo-2,3-dihydro-1,5-benzoxazepin-3-yl]pyrazolo[4,3-c]pyridine-6-carboxamide

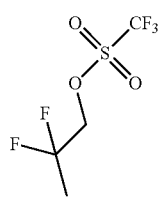

Step 1: 2,2-difluoropropyl trifluoromethanesulfonate

To a solution of 2,2-difluoropropanol (500 mg, 5.2 mmol) and triethylamine (632 mg, 6.2 mmol) in dichloromethane (5 mL) was added trifluoromethanesulfonic anhydride (1.76 g, 6.2 mmol) at −50° C. The reaction mixture was stirred at −50° C. for 2 h and then diluted with dichloromethane (20 mL). The organic layer was washed with water (10 mL), 1 M citric acid (10 mL), saturated aqueous sodium bicarbonate (10 mL), dried over anhydrous sodium sulfate and concentrated under reduced pressure (water bath temperature 0° C.) to give the crude 2,2-difluoropropyl trifluoromethanesulfonate (600 mg, 51%) as a pink oil, used in the next step without further purification.

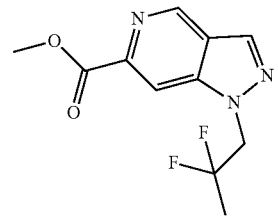 [SMILES: COC(=O)c1cc2c(cn1)cnn2CC(C)(F)F]

Step 2: methyl 1-(2,2-difluoropropyl)pyrazolo[4,3-c]pyridine-6-carboxylate

To a stirred solution of methyl 1H-pyrazolo[4,3-c]pyridine-6-carboxylate (50 mg, 0.28 mmol) in N,N-dimethylformamide (1 mL) was added cesium carbonate (138 mg, 0.42 mmol) and 2,2-difluoropropyl trifluoromethanesulfonate (129 mg, 0.56 mmol) at room temperature. The mixture was stirred at 100° C. for 2 h and then concentrated under reduced pressure. The residue was partitioned between ethyl acetate (10 mL) and water (10 mL). The separated organic layer was dried over sodium sulfate and concentrated under reduced pressure to afford crude methyl 1-(2,2-difluoropropyl)pyrazolo[4,3-c]pyridine-6-carboxylate (22 mg, 31%) as a yellow oil. $^1$H NMR (400 MHz, CD$_3$OD) δ 9.15 (s, 1H), 8.47 (s, 1H), 8.43 (d, J=14.8 Hz, 1H), 5.01 (t, J=13.2 Hz, 2H), 4.02 (s, 3H), 1.74-1.63 (m, 3H).

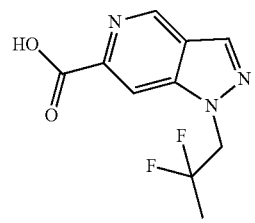 [SMILES: CC(F)(F)Cn1ncc2cnc(C(=O)O)cc21]

Step 3: 1-(2,2-difluoropropyl)pyrazolo[4,3-c]pyridine-6-carboxylic acid

To a solution of methyl 1-(2,2-difluoropropyl)pyrazolo[4,3-c]pyridine-6-carboxylate (192 mg, 0.75 mmol) in tetrahydrofuran (10 mL) and water (4 mL) was added lithium hydroxide (180 mg, 7.52 mmol). The reaction mixture was stirred at 25° C. for 3 h and then concentrated under reduced pressure. The residue was adjusted to pH=5 by additional of hydrochloric acid (2 N). The resulting mixture was extracted 1-(2,2-difluoropropyl)-N-[(3S)-5-methyl-4-oxo-2,3-dihydro-1,5-benzoxazepin-3-yl]pyrazolo[3,4-d]pyrimidine-6-carboxamide with dichloromethane (3×20 mL). The combined organic layers were washed with water (20 mL), brine (20 mL), dried over anhydrous sodium sulfate and concentrated under reduced pressure to afford 1-(2,2-difluoropropyl)pyrazolo[4,3-c]pyridine-6-carboxylic acid (75 mg, 41%) as a white solid, used as is in the next step.

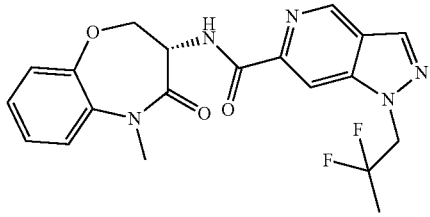 [SMILES: CN1C(=O)[C@@H](NC(=O)c2cc3c(cn2)cnn3CC(C)(F)F)COc2ccccc21]

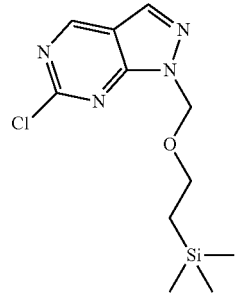

Step 4: 1-(2,2-difluoropropyl)-N-[(3S)-5-methyl-4-oxo-2,3-dihydro-1,5-benzoxazepin-3-yl]pyrazolo[4,3-c]pyridine-6-carboxamide A mixture of (3S)-3-amino-5-methyl-2,3-dihydro-1,5-benzoxazepin-4-one (14 mg, 0.07 mmol), 1-(2,2-difluoropropyl)pyrazolo[4,3-c]pyridine-6-carboxylic acid (17 mg, 0.07 mmol), 1-(3-dimethylaminopropyl)-3-ethylcarbodiimide hydrochloride (16 mg, 0.08 mmol) and 1-hydroxybenzotriazole (11 mg, 0.08 mmol) in N,N-dimethylformamide (2 mL) was stirred at 30° C. for 12 h. The mixture was concentrated under reduced pressure. The residue was purified by RP-HPLC (acetonitrile 40-70%/0.05% ammonia hydroxide in water) to afford 1-(2,2-difluoropropyl)-N-[(3S)-5-methyl-4-oxo-2,3-dihydro-1,5-benzoxazepin-3-yl]pyrazolo[4,3-c]pyridine-6-carboxamide (15.0 mg, 51%) as a white solid. $^1$H NMR (400 MHz, CD$_3$OD) δ 9.13 (s, 1H), 8.38 (s, 1H), 8.28 (s, 1H), 7.47-7.41 (m, 1H), 7.35-7.29 (m, 2H), 7.27-7.20 (m, 1H), 5.07-5.05 (m, 1H), 4.94 (t, J=13.2 Hz, 2H), 4.70-4.66 (m, 1H), 4.42-4.39 (m, 1H), 3.44 (s, 3H), 1.65 (t, J=18.8 Hz, 3H). LCMS R$_T$=1.858 min, m/z=416.1 [M+H]$^+$.

LCMS (10 to 80% acetonitrile in water+0.05% ammonium hydroxide over 3 mins) retention time 1.858 min, ESI+ found [M+H]=416.1.

Example #3

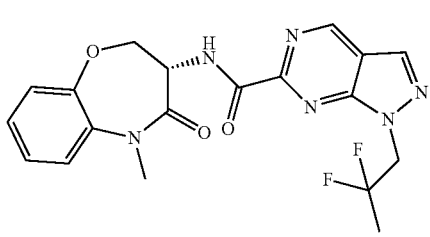

Step 1: 6-chloro-1-((2-(trimethylsilyl)ethoxy)methyl)-1H-pyrazolo[3,4-d]pyrimidine To a mixture of 6-chloro-1H-pyrazolo[3,4-d]pyrimidine (2.0 g, 12.9 mmol), potassium carbonate (3.6 g, 25.9 mmol) in N,N-dimethylformamide (20 mL) was added 2-(trimethylsilyl)ethoxymethyl chloride (2.6 g, 15.5 mmol). The reaction mixture was stirred at 25° C. for 2 h and poured into water (100 mL). The resulting mixture was extracted with ethyl acetate (3×100 mL). The combined organic layers were washed with water (100 mL), brine (100 mL), dried over anhydrous sodium sulfate and concentrated under reduced pressure. The residue was purified by column chromatography (silica gel, 100-200 mesh, 0 to 20% ethyl acetate in petroleum ether) to afford 6-chloro-1-((2-(trimethylsilyl)ethoxy)methyl)-1H-pyrazolo[3,4-d]pyrimidine (2.8 g, 76%) as a yellow oil. LCMS R$_T$=2.112 min, m/z=285.2 [M+H]$^+$.

LCMS (0 to 60% acetonitrile in water+0.03% trifluoroacetic acid over 2 mins) retention time 2.112 min, ESI+ found [M+H]=285.2.

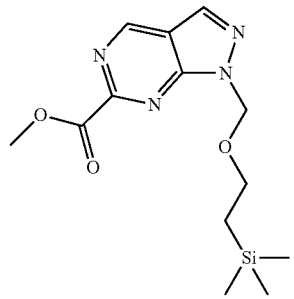

Step 2: methyl 1-((2-(trimethylsilyl)ethoxy)methyl)-1H-pyrazolo[3,4-d]pyrimidine-6-carboxylate A mixture of 6-chloro-1((2-(trimethylsilyl)ethoxy)methyl)-1H-pyrazolo[3,4-d]pyrimidine (2.80 g, 9.83 mmol), palladium(II) acetate (0.44 g, 1.97 mmol), 1,3-bis(diphenylphosphino)propane (0.81 g, 1.97 mmol), triethylamine (13.63 mL, 98.31 mmol) in 1-butanol (20 mL) and methanol (10 mL) was stirred at 120° C. for 24 h under CO (3.5 MPa). After cooled, the reaction mixture was filtered and the filtrate was concentrated under reduced pressure. The residue was purified by column chromatography (silica gel, 100-200 mesh, 0 to 20% ethyl acetate in petroleum ether) to afford methyl 1-(2-trimethylsilylethoxymethyl)pyrazolo[3,4-d]pyrimidine-6-carboxylate (750 mg, 25%) as a yellow oil and butyl 1-(2-trimethylsilylethoxymethyl)pyrazolo[3,4-d]pyrimidine-6-carboxylate (1.10 g, 32%) as a yellow oil. LCMS R$_T$=0.861 min, m/z=308.9 [M+H]$^+$.

LCMS (5 to 95% acetonitrile in water+0.03% trifluoroacetic acid over 1.5 mins) retention time 0.861 min, ESI+ found [M+H]=308.9.

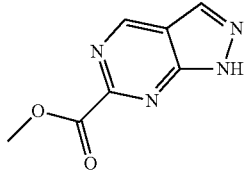

Step 3: methyl 1H-pyrazolo[3,4-d]pyrimidine-6-carboxylate

To a solution of methyl 1-(2-trimethylsilylethoxymethyl)pyrazolo[3,4-d]pyrimidine-6-carboxylate (800 mg, 2.59 mmol) in dichloromethane (15 mL) was added 2,2,2-trifluoroacetic acid (3.0 mL) at 0° C. The mixture was stirred at 0° C. for 2 h and the solvent was removed under reduced pressure. The residue was dissolved in ethyl acetate (50 mL), washed with saturated aqueous potassium carbonate (15 mL), dried over anhydrous sodium sulfate and concentrated under reduced pressure to give crude methyl 1H-pyrazolo[3,4-d]pyrimidine-6-carboxylate as light yellow solid (300 mg, 65%), used as is in the next step.

LCMS R$_T$=0.772 min, m/z=179.1 [M+H]$^+$.

LCMS (0 to 30% acetonitrile in water+0.03% trifluoroacetic acid over 2 mins) retention time 0.772 min, ESI+ found [M+H]=179.1.

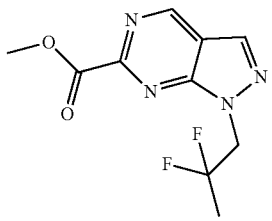 [SMILES: COC(=O)c1ncc2cnn(CC(C)(F)F)c2n1]

Step 4: methyl 1-(2,2-difluoropropyl)-1H-pyrazolo[3,4-d]pyrimidine-6-carboxylate To a stirred solution of methyl 1H-pyrazolo[3,4-d]pyrimidine-6-carboxylate (200 mg, 1.12 mmol) in N,N-dimethylformamide (5 mL) was added cesium carbonate (1.10 g, 3.37 mmol) and 2,2-difluoropropyl trifluoromethanesulfonate (1.28 g, 5.61 mmol). The reaction mixture was stirred at 80° C. for 3 h and poured into water (20 mL). The resulting mixture was extracted with ethyl acetate (3×30 mL). The combined organic layers was washed with brine (30 mL), dried over sodium sulfate and concentrated under reduce pressure. The residue was purified by column chromatography (silica gel, 100-200 mesh, 0 to 30% ethyl acetate in petroleum ether) to afford methyl 1-(2,2-difluoropropyl)pyrazolo[3,4-d]pyrimidine-6-carboxylate (120 mg, 42%) as a light yellow solid.

LCMS R$_T$=0.538 min, m/z=256.9 [M+H]$^+$.

LCMS (5 to 95% acetonitrile in water+0.05% ammonium hydroxide over 1.5 mins) retention time 0.538 min, ESI+ found [M+H]=256.9.

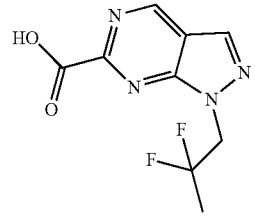 [SMILES: CC(F)(F)Cn1ncc2cnc(C(=O)O)nc21]

Step 5: 1-(2,2-difluoropropyl)-1H-pyrazolo[3,4-d]pyrimidine-6-carboxylic acid A mixture of methyl 1-(2,2-difluoropropyl)pyrazolo[3,4-d]pyrimidine-6-carboxylate (115 mg, 0.45 mmol) and lithium hydroxide monohydrate (28 mg, 0.67 mmol) in tetrahydrofuran (6 mL) and water (3 mL) was stirred at 25° C. for 3 h. The mixture was concentrated under reduced pressure. The residue was adjusted to pH=5 by additional of hydrochloric acid (2 N). The resulting mixture was extracted with ethyl acetate (3×20 mL). The combined organic layers were washed with water (20 mL), brine (20 mL), dried over anhydrous sodium sulfate and concentrated under reduced pressure to afford crude 1-(2,2-difluoropropyl)pyrazolo[3,4-d]pyrimidine-6-carboxylic acid (70 mg, 64%) as light yellow solid, used as is in the next step. LCMS R$_T$=0.804 min, m/z=243.2 [M+H]$^+$.

LCMS (0 to 60% acetonitrile in water+0.03% trifluoroacetic acid over 2 mins) retention time 0.804 min, ESI+ found [M+H]=243.2.

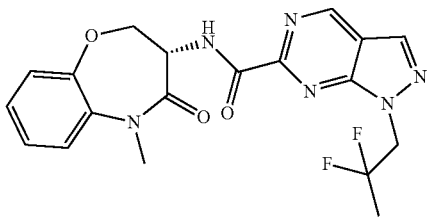 [SMILES: CN1C(=O)[C@@H](NC(=O)c2ncc3cnn(CC(C)(F)F)c3n2)COc2ccccc21]

Step 6: 1-(2,2-difluoropropyl)-N-[(3S)-5-methyl-4-oxo-2,3-dihydro-1,5-benzoxazepin-3-yl]pyrazolo[3,4-d]pyrimidine-6-carboxamide A mixture of 1-(2,2-difluoropropyl)pyrazolo[3,4-d]pyrimidine-6-carboxylic acid (30 mg, 0.12 mmol), 1-(3-dimethylaminopropyl)-3-ethylcarbodiimide hydrochloride (36 mg, 0.19 mmol), 1-hydroxybenzotriazole (25 mg, 0.19 mmol) and (3S)-3-amino-5-methyl-2,3-dihydro-1,5-benzoxazepin-4-one (24 mg, 0.12 mmol) in N,N-dimethylformamide (1.5 mL) was stirred at 25° C. for 4 h and then evaporated under reduced pressure. The residue was purified by RP-HPLC (acetonitrile 25-55%/0.05% ammonia hydroxide in water) to afford 1-(2,2-difluoropropyl)-N-[(3S)-5-methyl-4-oxo-2,3-dihydro-1,5-benzoxazepin-3-yl]pyrazolo

[3,4-d]pyrimidine-6-carboxamide (13.0 mg, 25%) as white solid. $^1$H NMR (400 MHz, CD$_3$OD) δ 9.43 (s, 1H), 8.47 (s, 1H), 7.48-7.28 (m, 4H), 5.10-5.01 (m, 3H), 4.74-4.69 (m, 1H), 4.51-4.45 (m, 1H), 3.46 (s, 3H), 1.71 (t, J=18.8 Hz, 3H).

LCMS R$_T$=1.625 min, m/z=417.1 [M+H]$^+$.

LCMS (10 to 80% acetonitrile in water+0.05% ammonium hydroxide over 3 minutes) retention time 1.625 min, ESI+ found [M+H]=417.1.

Example #4

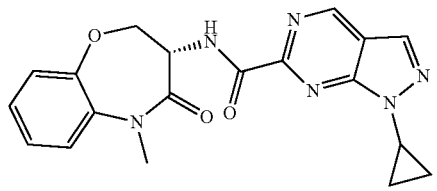 [SMILES: CN1C(=O)[C@@H](NC(=O)c2ncc3cnn(C4CC4)c3n2)COc2ccccc21]

1-cyclopropyl-N-[(3S)-5-methyl-4-oxo-2,3-dihydro-1,5-benzoxazepin-3-yl]pyrazolo[3,4-d]pyrimidine-6-carboxamide

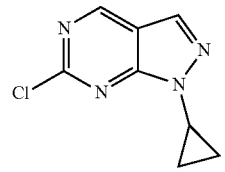 [SMILES: Clc1ncc2cnn(C3CC3)c2n1]

Step 1: 6-chloro-1-cyclopropyl-pyrazolo[3,4-d]pyrimidine

A mixture of 6-chloro-1H-pyrazolo[3,4-d]pyrimidine (300 mg, 1.94 mmol), cyclopropylboronic acid (333 mg, 3.88 mmol), copper(II) acetate (353 mg, 1.94 mmol), 2,2'-bipyridine (303 mg, 1.94 mmol) and sodium carbonate (411 mg, 3.88 mmol) in 1,2-dichloroethane (20 mL) was stirred at 70° C. for 4 h. The reaction mixture was diluted with water (10 mL) and extracted with dichloromethane (3×20 mL). The combined organic layers were washed with water (20 mL), brine (20 mL), dried over sodium sulfate and concentrated under reduced pressure. The residue was purified by column chromatography (silica gel, 100-200 mesh, 0 to 20% ethyl acetate in petroleum ether) to afford 6-chloro-1-cyclopropyl-pyrazolo[3,4-d]pyrimidine (70 mg, 19%) as a white solid. LCMS R$_T$=0.631 min, m/z=194.9 [M+H]+.

LCMS (5 to 95% acetonitrile in water+0.05% ammonium hydroxide over 3 minutes) retention time 0.631 min, ESI+ found [M+H]=194.9.

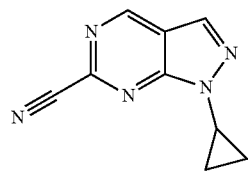 [SMILES: N#Cc1ncc2cnn(C3CC3)c2n1]

Step 2: 1-cyclopropylpyrazolo[3,4-d]pyrimidine-6-carbonitrile

To a stirred solution of 6-chloro-1-cyclopropyl-pyrazolo[3,4-d]pyrimidine (70 mg, 0.36 mmol) in dimethyl sulfoxide (3 mL) was added 1,4-diazabicyclo[2.2.2]octane (40 mg, 0.36 mmol) and sodium cyanide (35 mg, 0.72 mmol). The mixture reaction was stirred at 25° C. for 3 h and diluted with water (10 mL). The resulting mixture was extracted with ethyl acetate (3×20 mL). The combined organic layers were washed with water (20 mL), brine (20 mL), dried over sodium sulfate and concentrated under pressure to give crude 1-cyclopropylpyrazolo[3,4-d]pyrimidine-6-carbonitrile (60 mg, 90%) as a yellow oil. LCMS R$_T$=0.674 min, m/z=185.9 [M+H]+.

LCMS (5 to 95% acetonitrile in water+0.05% ammonium hydroxide over 3 minutes) retention time 0.674 min, ESI+ found [M+H]=185.9.

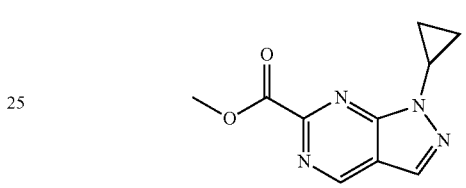

Step 3: methyl 1-cyclopropylpyrazolo[3,4-d]pyrimidine-6-carboxylate

To a stirred solution of 1-cyclopropylpyrazolo[3,4-d]pyrimidine-6-carbonitrile (50 mg, 0.27 mmol) in methanol (2 mL) was added hydrochloric acid (4 N in methanol, 2.5 mL, 10.0 mmol). The mixture was stirred at 70° C. for 4 h and concentrated under reduced pressure to give crude methyl 1-cyclopropylpyrazolo[3,4-d]pyrimidine-6-carboxylate (50 mg, 85%) as a white oil. LCMS R$_T$=0.574 min, m/z=219.1 [M+H]+.

LCMS (5 to 95% acetonitrile in water+0.05% ammonium hydroxide over 3 minutes) retention time 0.574 min, ESI+ found [M+H]=219.1.

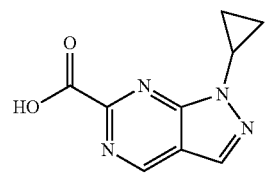 [SMILES: O=C(O)c1ncc2cnn(C3CC3)c2n1]

Step 4: 1-cyclopropylpyrazolo[3,4-d]pyrimidine-6-carboxylic acid

To a stirred solution of methyl 1-cyclopropylpyrazolo[3,4-d]pyrimidine-6-carboxylate (50 mg, 0.23 mmol) in tetrahydrofuran (5 mL) and water (1 mL) was added lithium hydroxide monohydrate (48 mg, 1.15 mmol). The mixture was stirred at 25° C. for 2 h and concentrated under reduced pressure to afford crude 1-cyclopropylpyrazolo[3,4-d]pyrimidine-6-carboxylic acid (50 mg, 99%) as a yellow solid.

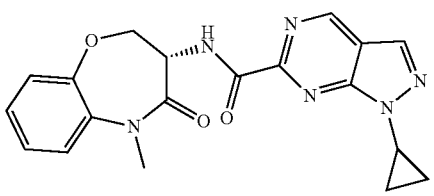 [SMILES: CN1C(=O)[C@@H](NC(=O)c2ncc3cnn(C4CC4)c3n2)COc2ccccc21]

Step 5: 1-cyclopropyl-N-[(3S)-5-methyl-4-oxo-2,3-dihydro-1,5-benzoxazepin-3-yl]pyrazolo[3,4-d]pyrimidine-6-carboxamide A mixture of 1-cyclopropylpyrazolo[3,4-d]pyrimidine-6-carboxylic acid (30 mg, 0.15 mmol), (3S)-3-amino-5-methyl-2,3-dihydro-1,5-benzoxazepin-4-one (31 mg, 0.16 mmol), 1-hydroxybenzotriazole (22 mg, 0.16 mmol) and 1-(3-dimethylaminopropyl)-3-ethylcarbodiimidehydrochloride (31 mg, 0.16 mmol) in N,N-dimethylformamide (5 mL) was stirred at 25° C. for 15 h and concentrated under reduced pressure. The residue was purified by RP-HPLC (acetonitrile 25-55%/0.05% ammonia hydroxide in water) to afford 1-cyclopropyl-N-[(3S)-5-methyl-4-oxo-2,3-dihydro-1,5-benzoxazepin-3-yl]pyrazolo[3,4-d]pyrimidine-6-carboxamide (10 mg, 17%) as a white solid. $^1$H NMR (400 MHz, CD$_3$OD) δ 9.34 (s, 1H), 8.31 (s, 1H), 7.49-7.43 (m, 1H), 7.37-7.30 (m, 2H), 7.30-7.24 (m, 1H), 5.08-5.06 (m, 1H), 4.74-4.70 (m, 1H), 4.49-4.43 (m, 1H), 4.15-4.10 (m, 1H), 3.45 (s, 3H), 1.40-1.31 (m, 2H), 1.26-1.18 (m, 2H). LCMS R$_T$=0.785 min, m/z=379.0 [M+H]$^+$.

LCMS (5 to 95% acetonitrile in water+0.05% ammonium hydroxide over 3 minutes) retention time 0.785 min, ESI+ found [M+H]=379.0.

Example #5

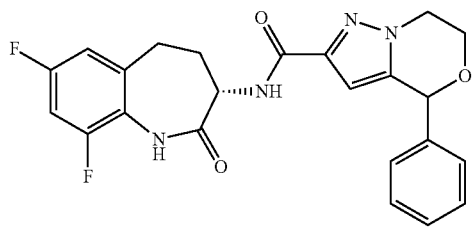 [SMILES: O=C(N[C@H]1CCc2cc(F)cc(F)c2NC1=O)c1cc2n(n1)CCOC2c1ccccc1]

4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide

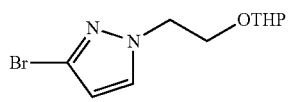

Step 1: 3-bromo-1-(2-((tetrahydro-2H-pyran-2-yl)oxy)ethyl)-1H-pyrazole

To a solution of 3-bromo-1H-pyrazole (5.0 g, 34.0 mmol) in acetonitrile (100 mL) was added cesium carbonate (16.6 g, 51.0 mmol) and 2-(2-bromoethoxy)tetrahydro-2h-pyran (7.5 g, 35.7 mmol). The mixture was stirred at 30° C. for 2 h and quenched by the addition of water (80 mL). The resulting mixture was extracted with ethyl acetate (3×100 mL). The combined organic layers were washed with water (20 mL), brine (20 mL), dried over anhydrous sodium sulfate and concentrated under reduced pressure. The residue was purified by column chromatography (silica gel, 100-200 mesh, 0 to 20% ethyl acetate in petroleum ether) to afford 3-bromo-1-(2-tetrahydropyran-2-yloxyethyl)pyrazole (5.5 g, 59%) as a yellow oil. $^1$HNMR (400 MHz, CDCl$_3$) δ 7.40 (d, J=2.4 Hz, 1H), 6.24 (d, J=1.2 Hz, 1H), 4.55-4.29 (m, 1H), 4.30-4.22 (m, 2H), 4.06-4.02 (m, 1H), 3.75-3.68 (m, 1H), 3.65-3.60 (m, 1H), 3.46-3.45 (m, 1H), 1.76-1.49 (m, 6H).

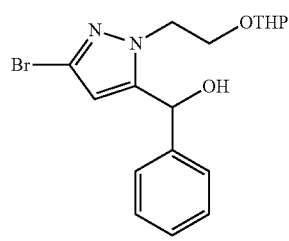

Step 2: (3-bromo-1-(2-((tetrahydro-2H-pyran-2-yl)oxy)ethyl)-1H-pyrazol-5-yl)(phenyl)methanol To a solution of lithium diisopropylamide (10.9 mL, 21.8 mmol) in tetrahydrofuran (100 mL) was added 3-bromo-1-(2-tetrahydropyran-2-yloxyethyl)pyrazole (4.0 g, 14.5 mmol) in tetrahydrofuran (2 mL) at −78° C. The resulting mixture was stirred at −78° C. for 30 min and benzaldehyde (1.8 g, 17.5 mmol) in tetrahydrofuran (2 mL) was added. The reaction mixture was allowed to warm to room temperature over 18 h and quenched by the addition of saturated aqueous ammonium chloride (20 mL). The mixture was extracted with ethyl acetate (3×100 mL). The combined organic layers were washed with water (50 mL), brine (50 mL), dried over anhydrous sodium sulfate and concentrated under reduced pressure. The residue was purified by column chromatography (silica gel, 100-200 mesh, 10 to 80% ethyl acetate in petroleum ether) to give [5-bromo-2-(2-tetrahydropyran-2-yloxyethyl)pyrazol-3-yl]-phenyl-methanol (3.5 g, 63%) as a colorless oil, used as is in the next step.

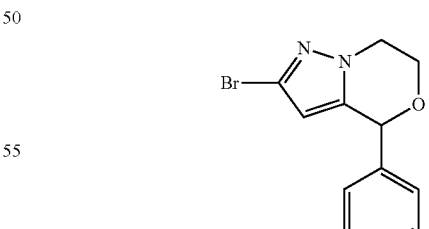

Step 3: 2-bromo-4-phenyl-6,7-dihydro-4H-pyrazolo[5,1-c][1,4]oxazine

To a solution of [5-bromo-2-(2-tetrahydropyran-2-yloxyethyl)pyrazol-3-yl]-phenyl-methanol (3.5 g, 9.18 mmol) was added p-toluenesulfonic acid (870 mg, 5.05 mmol). The reaction mixture was heated at reflux for 5 min and concentrated under reduced pressure. The residue was purified by column chromatography (silica gel, 100-200 mesh, 0 to 30% ethyl acetate in petroleum ether) to afford 2-bromo-4-phenyl-6,7-dihydro-4H-pyrazolo[5,1-c][1,4]oxazine (1.1 g, 43%) as a colorless oil. ¹H NMR (400 MHz, CDCl₃) δ 7.43-7.34 (m, 5H), 5.83 (d, J=1.0 Hz, 1H), 5.71 (s, 1H), 4.36-4.28 (m, 2H), 4.24-4.17 (m, 1H), 4.15-4.08 (m, 1H).

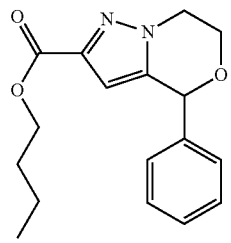 [SMILES: CCCCOC(=O)c1cc2n(n1)CCOC2c1ccccc1]

Step 4: butyl 4-phenyl-6,7-dihydro-4H-pyrazolo[5,1-c][1,4]oxazine-2-carboxylate

A mixture of 2-bromo-4-phenyl-6,7-dihydro-4H-pyrazolo[5,1-c][1,4]oxazine (110 mg, 0.39 mmol), palladium(II) acetate (9 mg, 0.04 mmol), 1,3-bis(diphenylphosphino)propane (16 mg, 0.04 mmol) and triethylamine (0.55 mL, 3.94 mmol) in 1-butanol (5 mL) was stirred at 100° C. for 48 h under carbon monoxide (3.2 Mpa). The mixture was filtered and the filtrate was concentrated under reduced pressure. The residue was purified by preparative TLC (petroleum ether:ethyl acetate=3:1, R$_f$=0.3) to give butyl 4-phenyl-6,7-dihydro-4H-pyrazolo[5,1-c][1,4]oxazine-2-carboxylate (50 mg, 42%), used as is in the next step.

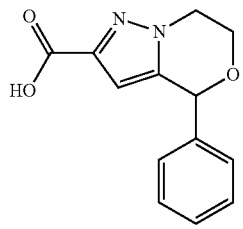 [SMILES: O=C(O)c1cc2n(n1)CCOC2c1ccccc1]

Step 5: 4-phenyl-6,7-dihydro-4H-pyrazolo[5,1-c][1,4]oxazine-2-carboxylic acid

To a solution of butyl 4-phenyl-6,7-dihydro-4H-pyrazolo[5,1-c][1,4]oxazine-2-carboxylate (50 mg, 0.17 mmol) in tetrahydrofuran (4 mL)/water (2 mL) was added lithium hydroxide monohydrate (50 mg, 1.2 mmol). The reaction mixture was stirred at 30° C. for 12 h and subsequently concentrated under reduced pressure. The aqueous residue was diluted with water (10 mL) and adjusted to pH=5 by addition of hydrochloric acid (1 N). The resulting mixture was extracted with dichloromethane (3×10 mL). The combined organic layers were concentrated under reduced pressure to afford crude 4-phenyl-6,7-dihydro-4H-pyrazolo[5,1-c][1,4]oxazine-2-carboxylic acid (25 mg, 62%) as a white solid, used in the next step without further purification. LCMS R$_T$=0.867 min, m/z=245.1 [M+H]⁺.

LCMS (10 to 80% acetonitrile in water+0.03% trifluoroacetic acid over 2.0 mins) retention time 0.867 min, ESI+ found [M+H]=245.1.

Step 6: 4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide A mixture of (3S)-3-amino-7,9-difluoro-1,3,4,5-tetrahydro-1-benzazepin-2-one (10 mg, 0.05 mmol), 1-(3-dimethylaminopropyl)-3-ethylcarbodiimide hydrochloride (11 mg, 0.06 mmol), 1-hydroxybenzotriazole (8 mg, 0.06 mmol) and 4-phenyl-6,7-dihydro-4H-pyrazolo[5,1-c][1,4]oxazine-2-carboxylic acid (12 mg, 0.05 mmol) in N,N-dimethylformamide (2 mL) was stirred at 30° C. for 15 h. The mixture was concentrated under reduced pressure and the residue was purified by RP-HPLC (acetonitrile 38-48%/0.05% ammonia hydroxide in water) to afford 4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide (6 mg, 29%) as a white solid. ¹H NMR (400 MHz, CD₃OD) δ 7.37 (s, 5H), 7.02-6.96 (m, 2H), 6.18 (s, 1H), 5.80 (s, 1H), 4.53 (dd, J=8.0, 11.6 Hz, 1H), 4.40-4.27 (m, 3H), 4.21-4.14 (m, 1H), 2.98-2.94 (m, 1H), 2.83-2.78 (m, 1H), 2.62-2.59 (m, 1H), 2.23-2.15 (m, 1H). LCMS R$_T$=1.838 min, m/z=439.1 [M+H]⁺.

LCMS (10 to 80% acetonitrile in water+0.05% ammonium hydroxide over 3 minutes) retention time 1.838 min, ESI+ found [M+H]=439.1.

Example #6

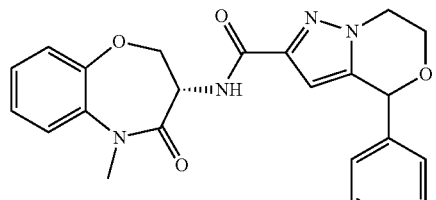

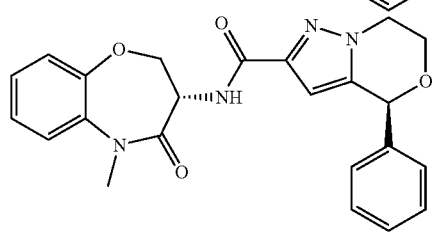

4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide and (4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide

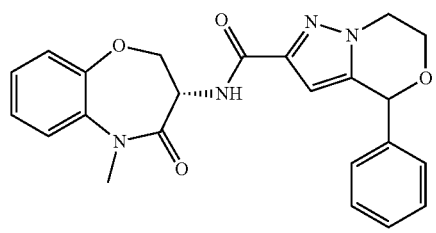 [SMILES: CN1C(=O)[C@@H](NC(=O)c2cc3n(n2)CCOC3c2ccccc2)COc2ccccc21]

Step 1 4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide A mixture of (3S)-3-amino-5-methyl-2,3-dihydro-1,5-benzoxazepin-4-one (24 mg, 0.13 mmol), 1-hydroxybenzotriazole (17 mg, 0.13 mmol), 1-(3-dimethylaminopropyl)-3-ethylcarbodiimide hydrochloride (24 mg, 0.13 mmol) and 4-phenyl-6,7-dihydro-4H-pyrazolo[5,1-c][1,4]oxazine-2-carboxylic acid (31 mg, 0.13 mmol) in N,N-dimethylformamide (3 mL) was stirred at 25° C. for 3 h. The mixture was concentrated under reduced pressure. The residue was purified by RP-HPLC (acetonitrile 35-65%/0.05% ammonia hydroxide in water) to afford 4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide (18.1 mg, 32%) as a white solid. $^1$H NMR (400 MHz, CD$_3$OD) δ 7.40-7.37 (m, 1H), 7.34 (s, 5H), 7.29-7.25 (m, 2H), 7.20-7.17 (m, 1H), 6.15 (s, 1H), 5.77 (s, 1H), 4.54-4.50 (m, 1H), 4.37-4.33 (m, 2H), 4.31-4.21 (m, 2H), 4.21-4.08 (m, 2H), 3.37 (s, 3H). LCMS R$_T$=1.889 min, m/z=419.1 [M+H]+.

LCMS (10 to 80% acetonitrile in water+0.05% ammonium hydroxide over 3 mins) retention time 1.889 min. ESI+ found [M+H]=419.1.

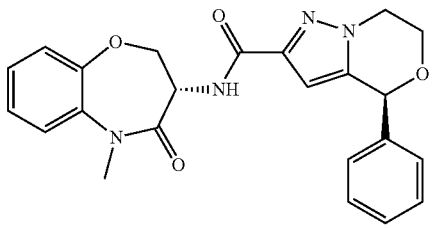 [SMILES: CN1C(=O)[C@@H](NC(=O)c2cc3n(n2)CCO[C@H]3c2ccccc2)COc2ccccc21]

Step 2 (4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide Racemic N-[(3S)-5-methyl-4-oxo-2,3-dihydro-1,5-benzoxazepin-3-yl]-4-phenyl-6,7-dihydro-4H-pyrazolo[5,1-c][1,4]oxazine-2-carboxamide (60 mg, 0.14 mmol) was separated by chiral SFC to afford arbitrarily assigned:

(4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide (Peak 1, retention time=3.856 min) (17.4 mg, 29%) as a brown solid. $^1$H NMR (400 MHz, CD$_3$OD) δ 7.43-7.40 (m, 1H), 7.37 (s, 5H), 7.33-7.26 (m, 2H), 7.23-7.19 (m, 1H), 6.18 (s, 1H), 5.80 (s, 1H), 4.97-4.94 (m, 1H), 4.57-4.53 (m, 1H), 4.41-4.34 (m, 3H), 4.32-4.26 (m, 1H), 4.21-4.14 (m, 1H), 3.40 (s, 3H). LCMS R$_T$=1.899 min, m/z=419.2 [M+H]$^-$ LCMS (10 to 80% acetonitrile in water+0.05% ammonium hydroxide over 3 mins) retention time 1.899 min, ESI+ found [M+H]=419.1.

SFC conditions: Column: Chiralcel OJ-3 100×4.6 mm I.D., 3 um; Mobile phase: A: CO$_2$ B: ethanol (0.05% DEA); Gradient: from 5% to 40% of B in 4.5 min and hold 40% for 2.5 min, then 5% of B for 1 min; Flow rate: 2.8 mL/min; Column temperature: 40° C.

Example #7

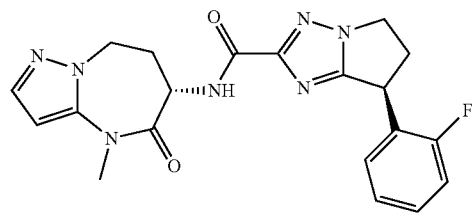 [SMILES: CN1C(=O)[C@@H](NC(=O)c2nc3n(n2)CC[C@H]3c2ccccc2F)CCn2nccc21]

(7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide

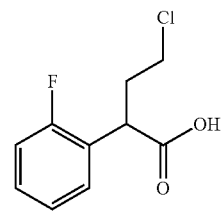 [SMILES: O=C(O)C(CCCl)c1ccccc1F]

Step 1: 4-chloro-2-(2-fluorophenyl)butanoic acid

To a stirred solution of 2-(2-fluorophenyl)acetic acid (10.0 g, 64.9 mmol) in tetrahydrofuran (300 mL) was added n-butyllithium (2.5 M in hexanes, 51.9 mL, 129.8 mmol) dropwise at −78° C. The resulting mixture was stirred for 20 min at −78° C. and 1 h at 0° C., and subsequently 1-bromo-2-chloroethane (5.59 mL, 64.9 mmol) was added. The reaction mixture was allowed to warm to 25° C. over 15 h and quenched by addition of hydrochloric acid (1 N, 100 mL). The mixture was extracted with ethyl acetate (3×150 mL). The combined organic layers were washed with brine (200 mL) and concentrated under reduced pressure. The residue was purified by column chromatography (silica gel, 100-200 mesh, dichloromethane) to afford 4-chloro-2-(2-fluorophenyl)butanoic acid (9.5 g, 68%) as a yellow oil. $^1$HNMR (400 MHz, CD$_3$OD) δ 7.41-7.24 (m, 2H), 7.21-6.98 (m, 2H), 4.18-4.08 (m, 1H), 3.63-3.55 (m, 1H), 3.46-3.38 (m, 1H), 2.58-2.47 (m, 1H), 2.25-2.10 (m, 1H).

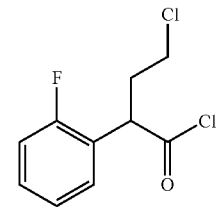 [SMILES: O=C(Cl)C(CCCl)c1ccccc1F]

Step 2: 4-chloro-2-(2-fluorophenyl)butanoyl chloride

To a mixture of 4-chloro-2-(2-fluorophenyl)butanoic acid (1.0 g, 4.62 mmol) in dichloromethane (6 mL), one drop N,N-dimethylformamide and oxalyl chloride (1.97 mL, 23 2 mmol) was added dropwise. The mixture was stirred at 25° C. for 1.5 h and concentrated under reduced pressure (below 30° C.) to afford crude 4-chloro-2-(2-fluorophenyl)butanoyl chloride (1.08 g, 99%) as a yellow oil, use in the next step without further purification.

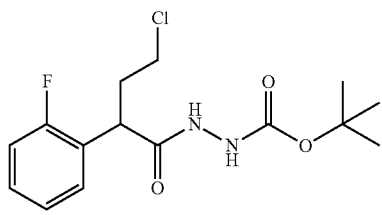 [SMILES: CC(C)(C)OC(=O)NNC(=O)C(CCCl)c1ccccc1F]

Step 3: tert-butyl 2-(4-chloro-2-(2-fluorophenyl) butanoyl)hydrazinecarboxylate

To a solution of triethylamine (0.81 mL, 13.78 mmol) and tert-butyl hydrazinecarboxylate (1.21 g, 9.19 mmol) in tetrahydrofuran (30 mL) was added 4-chloro-2-(2-fluorophenyl)butanoyl chloride (1.08 g, 4.59 mmol) in tetrahydrofuran (3 mL) at 0° C. The resulting mixture was stirred at 0° C. for 2 h and subsequently diluted with water (150 mL) and ethyl acetate (200 mL). The separated organic layer was washed with 1 N hydrochloric acid (2×30 mL) and brine (30 mL), dried over anhydrous sodium sulfate and concentrated under reduced pressure. The residue was purified by column chromatography (silica gel, 100-200 mesh, 0 to 4% methanol in dichloromethane) to afford tert-butyl 2-(4-chloro-2-(2-fluorophenyl)butanoyl)hydrazinecarboxylate (1.07 g, 70%) as a yellow oil.

LCMS RT=0.741 min, m/z=230.8 [M−100+H]$^+$.

LCMS (5 to 95% acetonitrile in water+0.03% trifluoroacetic acid over 1.5 mins) retention time 0.741 min, ESI+ found [M−100+H]=230.8.

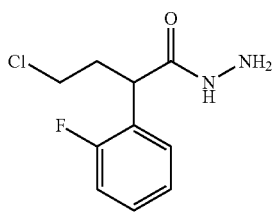 [SMILES: NNC(=O)C(CCCl)c1ccccc1F]

Step 4: 4-chloro-2-(2-fluorophenyl)butanehydrazide

To s solution of tert-butyl N-[[4-chloro-2-(2-fluorophenyl)butanoyl]amino]carbamate (1.07 g, 3.2 mmol) in ethyl acetate (2.0 mL) was added hydrochloric acid (4.0 N in ethyl acetate, 10.0 mL, 40.0 mmol). The mixture was stirred for 1.5 h and concentrated under reduced pressure. The residue was diluted with ethyl acetate (60 mL), washed with saturated aqueous sodium bicarbonate (20 mL), brine (20 mL), dried over sodium sulfate and concentrated under reduced pressure to afford crude 4-chloro-2-(2-fluorophenyl)butanehydrazide (740 mg, 100%) as a yellow oil. LCMS RT=0.591 min, m/z=230.8 [M+H]$^+$.

LCMS (5 to 95% acetonitrile in water+0.03% trifluoroacetic acid over 1.5 mins) retention time 0.591 min, ESI+ found [M+H]=230.8.

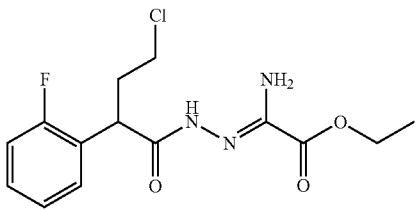 [SMILES: CCOC(=O)/C(N)=N/NC(=O)C(CCCl)c1ccccc1F]

Step 5: (Z)-ethyl 2-amino-2-(2-(4-chloro-2-(2-fluorophenyl)butanoyl)hydrazono)acetate To a solution of 4-chloro-2-(2-fluorophenyl)butanehydrazide (746 mg, 3.23 mmol) in ethanol (10 mL) was added ethyl 2-ethoxy-2-imino-acetate (469 mg, 3.23 mmol). The mixture was stirred at 25° C. for 2 h and then filtered. The solid was dried in vacuo to afford crude (Z)-ethyl 2-amino-2-(2-(4-chloro-2-(2-fluorophenyl)butanoyl)hydrazono)acetate (650 mg, 61%) as a white solid, used in the next step without any further purification. LCMS RT=0.786 min, m/z=329.9 [M+H]$^+$.

LCMS (5 to 95% acetonitrile in water+0.03% trifluoroacetic acid over 1.5 mins) retention time 0.786 min, ESI+ found [M+H]=329.9.

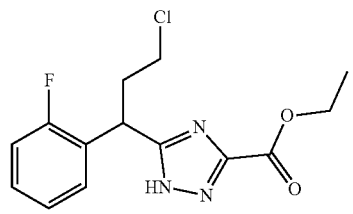 [SMILES: CCOC(=O)c1n[nH]c(C(CCCl)c2ccccc2F)n1]

Step 6: ethyl 5-(3-chloro-1-(2-fluorophenyl)propyl)-1H-1,2,4-triazole-3-carboxylate A mixture of ethyl (2E)-2-amino-2-[[4-chloro-2-(2-fluorophenyl)butanoyl]hydrazono]acetate (650 mg, 1.97 mmol) and phosphorus oxychloride (8.0 mL, 85.57 mmol) was stirred at 120° C. for 1.5 h and subsequently quenched by addition of water (50 mL). The resulting mixture was extracted with ethyl acetate (2×50 mL). The combined organic layers were dried over sodium sulfate and concentrated under reduced pressure to afford crude ethyl 5-[3-chloro-1-(2-fluorophenyl)propyl]-1H-1,2,4-triazole-3-carboxylate (614 mg, 100%) as a colorless oil, used in the next step without further purification. LCMS R$_T$=0.716 min, m/z=311.9 [M+H]$^−$.

LCMS (5 to 95% acetonitrile in water+0.03% trifluoroacetic acid over 1.5 mins) retention time 0.716 min, ESI+ found [M+H]=311.9.

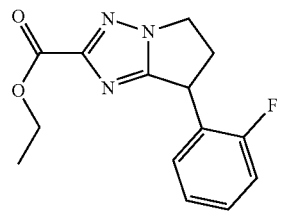 [SMILES: CCOC(=O)c1nc2n(n1)CCC2c1ccccc1F]

Step 7: ethyl 7-(2-fluorophenyl)-6,7-dihydro-5H-pyrrolo[1,2-b][1,2,4]triazole-2-carboxylate To a solution of ethyl 5-[3-chloro-1-(2-fluorophenyl)propyl]-1H-1,2,4-triazole-3-carboxylate (614 mg, 1.97 mmol) in N,N-dimethylformamide (4 mL) was added potassium carbonate (272 mg, 1.97 mmol). The reaction mixture was stirred at 25° C. for 15 h and filtered. The filtrate was concentrated under reduced pressure and the residue was purified by column chromatography (silica gel, 100-200 mesh, 0 to 3% methanol in dichloromethane) to afford ethyl 7-(2-fluorophenyl)-6,7-dihydro-5H-pyrrolo[1,2-b][1,2,4]triazole-2-carboxylate (450 mg, 83%) as a yellow oil. $^1$H NMR (400 MHz, CD$_3$OD) δ 7.41-7.25 (m, 2H), 7.22-7.08 (m, 2H), 4.76-4.72 (m, 1H), 4.49-4.28 (m, 4H), 3.38-3.33 (m, 1H), 2.84-2.66 (m, 1H), 1.38 (t, J=7.2 Hz, 3H).

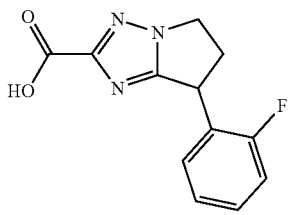 [SMILES: O=C(O)c1nc2n(n1)CCC2c1ccccc1F]

Step 8: 7-(2-fluorophenyl)-6,7-dihydro-5H-pyrrolo[1,2-b][1,2,4]triazole-2-carboxylic acid A mixture of ethyl 7-(2-fluorophenyl)-6,7-dihydro-5H-pyrrolo[1,2-b][1,2,4]triazole-2-carboxylate (450 mg, 1.63 mmol) and lithium hydroxide monohydrate (141 mg, 3.37 mmol) in tetrahydrofuran (30 mL)/water (7 mL) was stirred at 25° C. for 2 h and concentrated under reduced pressure. The aqueous residue was diluted with water (10 mL) and adjusted to pH=5 by addition of 1N HCl. The resulting mixture was extracted with dichloromethane (4×50 mL). The combined organic layers were dried over sodium sulfate and concentrated under reduced pressure to afford crude 7-(2-fluorophenyl)-6,7-dihydro-5H-pyrrolo[1,2-b][1,2,4]triazole-2-carboxylic acid (200 mg, 50%), used in the next step without further purification. LCMS R$_T$=0.658 min, m/z=247.9 [M+H]$^+$.

LCMS (5 to 95% acetonitrile in water+0.03% trifluoroacetic acid over 1.5 mins) retention time 0.658 min, ESI+ found [M+H]=247.9

Step 9: (7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide A mixture of 1-hydroxybenzotriazole (11 mg, 0.08 mmol), (6S)-6-amino-4-methyl-7,8-dihydro-6H-pyrazolo[1,5-a][1,3]diazepin-5-one (73 mg, 0.40 mmol), 1-(3-dimethylaminopropyl)-3-ethylcarbodiimide hydrochloride (116 mg, 0.61 mmol) and 7-(2-fluorophenyl)-6,7-dihydro-5H-pyrrolo[1,2-b][1,2,4]triazole-2-carboxylic acid (100 mg, 0.40 mmol) in N,N-dimethylformamide (3 mL) was stirred at 20° C. for 15 h. The mixture was concentrated under reduced pressure and the residue was purified by preparative TLC (dichloromethane:methanol=20:1) to give 7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (50 mg, 30%).

The above racemic material was further separated by chiral SFC to afford arbitrarily assigned:

(7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 1, retention time=3.582 min) (10.5 mg, 20%). $^1$H NMR (400 MHz, CD$_3$OD) δ 7.51 (s, 1H), 7.35-7.27 (m, 2H), 7.19-7.15 (m, 2H), 6.29 (d, J=2.0 Hz, 1H), 4.75-4.72 (m, 1H), 4.52-4.47 (m, 1H), 4.43-4.30 (m, 2H), 4.28-4.20 (m, 2H), 3.31 (s, 3H), 2.88-2.74 (m, 2H), 2.70-2.65 (m, 1H), 2.28-2.24 (m, 1H). LCMS R$_T$=0.758 min, m/z=410.0 [M+H]$^+$.

LCMS (5 to 95% acetonitrile in water+0.03% trifluoroacetic acid over 2 mins) retention time 0.758 min, ESI+ found [M+H]=410.0.

SFC conditions: Column: Column: Chiralcel OJ 250×30 mm I.D., 5 um, Mobile phase: A: CO$_2$ B: ethanol (0.1% NH$_3$H$_2$O). Gradient: from 25% to 75% of B in 4.5 min and hold 75% for 2.5 min, then 5% of B for 1 min. Flow rate: 2.8 mL/min Column temp: 38° C.

Example #8

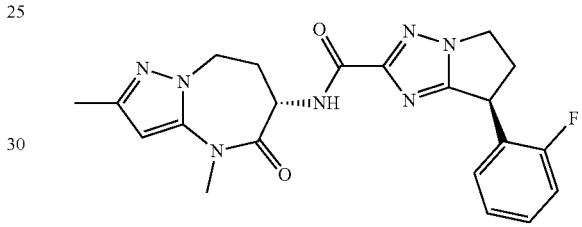

(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide A mixture of (6S)-6-amino-2,4-dimethyl-7,8-dihydro-6H-pyrazolo[1,5-a][1,3]diazepin-5-one (78 mg, 0.4 mmol), 1-hydroxybenzotriazole (11 mg, 0.08 mmol), 1-(3-dimethylaminopropyl)-3-ethylcarbodiimide hydrochloride (116 mg, 0.61 mmol) and 7-(2-fluorophenyl)-6,7-dihydro-5H-pyrrolo[1,2-b][1,2,4]triazole-2-carboxylic acid (100 mg, 0.40 mmol) in N,N-dimethylformamide (3 mL) was stirred at 25° C. for 15 h. The mixture was concentrated under reduced pressure and the residue was purified by RP-HPLC (acetonitrile 20-50/0.05% ammonia hydroxide in water) to afford N-[(6S)-2,4-dimethyl-5-oxo-7,8-dihydro-6H-pyrazolo[1,5-a][1,3]diazepin-6-yl]-7-(2-fluorophenyl)-6,7-dihydro-5H-pyrrolo[1,2-b][1,2,4]triazole-2-carboxamide (70 mg, 41%) as a yellow oil. LCMS R$_T$=0.659 min, m/z=424.1 [M+H]$^+$.

LCMS (5 to 95% acetonitrile in water+0.03% trifluoroacetic acid over 1.5 mins) retention time 0.659 min, ESI+ found [M+H]=424.1.

The above racemic material was further separated by chiral SFC to afford arbitrarily assigned:

(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 1, retention time=3.582 min) (19.5 mg, 28%). $^1$H NMR (400 MHz, CD$_3$OD) δ7.39-7.26 (m, 2H), 7.20-7.10 (m, 2H), 6.11 (s, 1H), 4.77-4.69 (m, 1H), 4.56-4.49 (m, 1H), 4.46-4.37 (m, 1H), 4.35-4.26 (m, 2H), 4.25-4.15 (m, 1H), 3.32 (s, 3H), 2.91-2.64 (m, 3H), 2.30-2.19 (m, 4H). LCMS $R_T$=0.764 min, m/z=424.1 [M+H]⁻.

LCMS (5 to 95% acetonitrile in water+0.03% trifluoroacetic acid over 1.5 mins) retention time 0.764 min, ESI+ found [M+H]=424.1.

SFC conditions: Column: Column: Chiralpak AD-3 100× 4.6 mm I.D., 3 um Mobile phase: A: CO₂ B: ethanol (0.05% DEA). Gradient: from 5% to 40% of B in 4.5 min and hold 40% for 2.5 min, then 5% of B for 1 min. Flow rate: 2.8 mL/min Column temp: 40° C.

Example #9

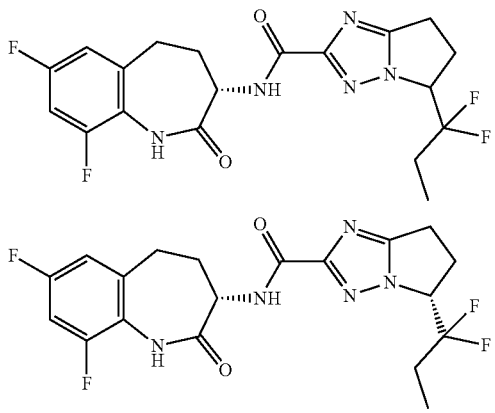

[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide and (5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide

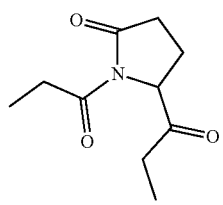

Step 1: 1,5-di(propanoyl)pyrrolidin-2-one

A mixture of D-glutamic acid (17.0 g, 115.5 mmol) and 4-dimethylaminopyridine (847 mg, 6.9 mmol) and propionic anhydride (51.2 g, 392.9 mmol) in triethylamine (51.0 mL, 366.3 mmol) was stirred at 60° C. for 15 h and subsequently concentrated under reduced pressure. The residue was purified by column chromatography (silica gel, 100-200 mesh, 0 to 40% ethyl acetate in petroleum ether) to afford 1,5-di(propanoyl)pyrrolidin-2-one (6.0 g, 26%) as a yellow oil, used in the next step as is.

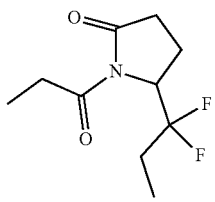

Step 2: 5-(1,1-difluoropropyl)-1-propanoyl-pyrrolidin-2-one

A solution of 1,5-di(propanoyl)pyrrolidin-2-one (1.0 g, 5.1 mmol) in diethylaminosulfur trifluoride (1.2 g, 7.6 mmol) was stirred at 50° C. for 16 h and subsequently quenched by addition of saturated aqueous sodium bicarbonate (20 mL). The reaction mixture was extracted with dichloromethane (3×20 mL). The combined organic layers were washed with brine (20 mL), dried over anhydrous sodium sulfate and concentrated under reduced pressure. The residue was purified by preparative TLC (10% ethyl acetate in petroleum ether, $R_f$=0.4) to afford 5-(1,1-difluoropropyl)-1-propanoyl-pyrrolidin-2-one (200 mg, 18%) as a yellow oil, used as is in the next step.

Step 3: 5-(1,1-difluoropropyl)pyrrolidin-2-one

To a solution of 5-(1,1-difluoropropyl)-1-propanoyl-pyrrolidin-2-one (200 mg, 0.91 mmol) in methanol (10 mL) was added sodium hydride (60%, 9 mg, 0.23 mmol). The reaction mixture was stirred at 25° C. for 12 h and concentrated under reduced pressure to afford crude 5-(1,1-difluoropropyl)pyrrolidin-2-one (200 mg, 81%, 60% purity) as a yellow oil, used as is in the next step.

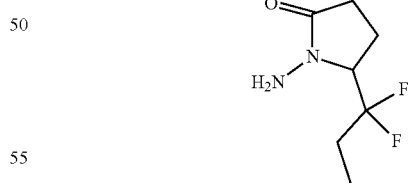

Step 4: 1-amino-5-(1,1-difluoropropyl)pyrrolidin-2-one

To a solution of 5-(1,1-difluoropropyl)pyrrolidin-2-one (200 mg, 0.74 mmol, 60% purity) in N,N-dimethylformamide (5 mL) was added sodium hydride (60%, 44 mg, 1.10 mmol) at 0° C. The mixture was stirred at 0° C. for 30 min and o-(diphenylphosphoryl) hydroxylamine (257 mg, 1.10 mmol) was added. After addition, the reaction mixture was stirred at 0° C. for 16 h and subsequently filtered. The filtrate was concentrated under reduced pressure to afford crude 1-amino-5-(1,1-difluoropropyl)pyrrolidin-2-one (120 mg, 92%) as a yellow oil. LCMS $R_T$=1.146 min, m/z=179.1 [M+H]⁻.

LCMS (0 to 60% acetonitrile in water+0.03% trifluoacetic acid over 3.0 mins) retention time 1.146 min, ESI+ found [M+H]=179.1.

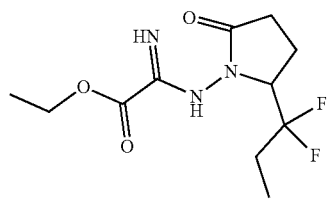 [SMILES: CCOC(=O)C(=N)NN1C(=O)CCC1C(F)(F)CC]

Step 5: ethyl 2-[[2-(1,1-difluoropropyl)-5-oxo-pyrrolidin-1-yl]amino]-2-imino-acetate To a solution of 1-amino-5-(1,1-difluoropropyl)pyrrolidin-2-one (120 mg, 0.67 mmol) in ethanol (5 mL) was added ethyl 2-ethoxy-2-imino-acetate (489 mg, 3.37 mmol). The reaction mixture was stirred at 60° C. for 16 h and subsequently concentrated under reduced pressure to afford ethyl 2-[[2-(1,1-difluoropropyl)-5-oxo-pyrrolidin-1-yl]amino]-2-imino-acetate (600 mg, 80%, 40% purity) as a yellow oil, used as is in the next step.

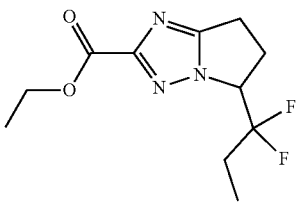 [SMILES: CCOC(=O)c1nc2n(n1)C(C(F)(F)CC)CC2]

Step 6: ethyl 5-(1,1-difluoropropyl)-6,7-dihydro-5H-pyrrolo[1,2-b][1,2,4]triazole-2-carboxylate A solution of ethyl 2-[[2-(1,1-difluoropropyl)-5-oxo-pyrrolidin-1-yl]amino]-2-imino-acetate (600 mg, 0.43 mmol, 40% purity) in phosphorus oxychloride (2.5 mL, 4.33 mmol) was stirred at 120° C. for 1 h. After cooled, the mixture was quenched by addition of water (20 mL) and extracted with dichloromethane (3×20 mL). The combined organic layers were washed with saturated aqueous sodium bicarbonate (20 mL), brine (20 mL), dried over anhydrous sodium sulfate and concentrated under reduced pressure. The residue was purified by RP-HPLC (acetonitrile 32-62/0.05% hydrochloric acid in water) to afford ethyl 5-(1,1-difluoropropyl)-6,7-dihydro-5H-pyrrolo[1,2-b][1,2,4]triazole-2-carboxylate (35 mg, 31%) as a light yellow oil. LCMS $R_T$=1.090 min, m/z=260.2 [M+H]⁺.

LCMS (5 to 95% acetonitrile in water+0.03% trifluoacetic acid over 1.5 mins) retention time 1.090 min, ESI+ found [M+H]=260.2.

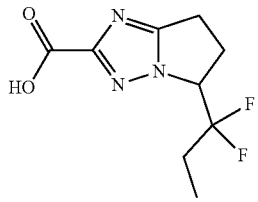 [SMILES: CCC(F)(F)C1CCc2nc(C(=O)O)nn21]

Step 7: 5-(1,1-difluoropropyl)-6,7-dihydro-5H-pyrrolo[1,2-b][1,2,4]triazole-2-carboxylic acid To a solution of ethyl 5-(1,1-difluoropropyl)-6,7-dihydro-5H-pyrrolo[1,2-b][1,2,4]triazole-2-carboxylate (25 mg, 0.1 mmol) in tetrahydrofuran (1.0 mL) and water (0.5 mL) was added lithium hydroxide monohydrate (20 mg, 0.5 mmol). The mixture was stirred at 25° C. for 12 h and concentrated under reduced pressure. The residue was adjusted to pH=4 by addition of hydrochloric acid (1 N). The resulting mixture was concentrated under reduced pressure to give crude 5-(1,1-difluoropropyl)-6,7-dihydro-5H-pyrrolo[1,2-b][1,2,4]triazole-2-carboxylic acid (20 mg, 90%) as a yellow solid. LCMS $R_T$=1.322 min, m/z=232.1 [M+H]⁻.

LCMS (0 to 60% acetonitrile in water+0.03% trifluoacetic acid over 3.0 mins) retention time 1.322 min, ESI+ found [M+H]=232.1.

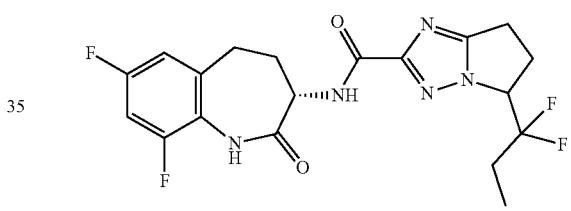

Step 8: 5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide A mixture of 5-(1,1-difluoropropyl)-6,7-dihydro-5H-pyrrolo[1,2-b][1,2,4]triazole-2-carboxylic acid (20 mg, 0.09 mmol), 1-(3-dimethylaminopropyl)-3-ethylcarbodiimide hydrochloride (25 mg, 0.13 mmol), (3S)-3-amino-7,9-difluoro-1,3,4,5-tetrahydro-1-benzazepin-2-one (18 mg, 0.09 mmol) and 1-hydroxybenzotriazole (17 mg, 0.13 mmol) in N,N-dimethylformamide (5 mL) was stirred at 25° C. for 4 h. The reaction mixture was concentrated under reduced pressure. The residue was purified by RP-HPLC (acetonitrile 24-54%/0.05% ammonium hydroxide in water) to afford 5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (13.1 mg, 35%) as a white solid. ¹HNMR (400 MHz, CD₃OD) δ 7.02-6.99 (m, 2H), 4.86-4.82 (m, 1H), 4.65-4.54 (m, 1H), 3.10-2.79 (m, 6H), 2.77-2.63 (m, 1H), 2.31-2.03 (m, 3H), 1.12 (t, J=7.2 Hz, 3H). LCMS $R_T$=0.989 min, m/z=426.2 [M+H]⁺.

LCMS (10 to 80% acetonitrile in water+0.03% trifluoacetic acid over 2.0 mins) retention time 0.989 min, ESI+ found [M+H]=426.2.

47

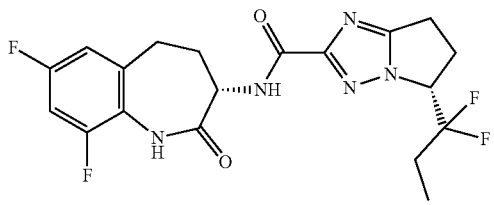

Step 9: (5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Racemic 5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (50 mg, 0.12 mmol) was separated by chiral SFC to afford arbitrarily assigned:

(5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (Peak 2, $R_T$=3.630 min) (25 mg, 49%) as a white solid. $^1$H NMR (400 MHz, METHANOL-d4) δ 7.04-6.98 (m, 2H), 4.60-4.55 (m, 2H), 3.01-2.95 (m, 3H), 2.89-2.79 (m, 2H), 2.71-2.64 (m, 1H), 2.29-2.18 (m, 2H), 2.18-2.02 (m, 2H), 1.10 (t, J=7.2 Hz, 3H). LCMS $R_T$=1.747 min, m/z=426.3 [M+H]$^+$.

LCMS (0 to 60% acetonitrile in water+0.03% trifluoacetic acid over 3.0 mins) retention time 1.747 min, ESI+ found [M+H]=426.3.

SFC conditions: Column: Chiralcel OD-3 100×4.6 mm I.D., 3 um Mobile phase: A: CO2 B: ethanol (0.05% dethyl acetate), Gradient: from 5% to 40% of B in 4.5 min and hold 40% for 2.5 min, then 5% of B in 1 min. Flow rate: 2.8 mL/min Column temperature: 40° C.

Example #10

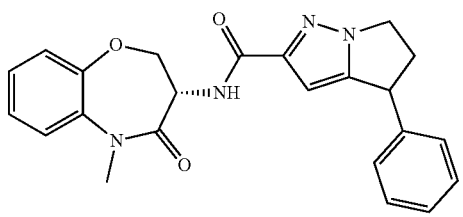

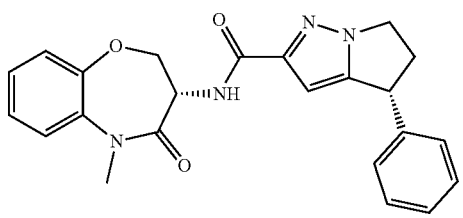

48

4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide and (4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide

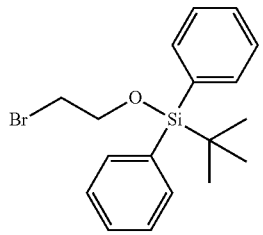 [SMILES: CC(C)(C)[Si](OCCBr)(c1ccccc1)c1ccccc1]

Step 1: (2-bromoethoxy)(tert-butyl)diphenylsilane

To a solution of 2-bromoethanol (2.0 g, 16.0 mmol) and imidazole (3.27 g, 48.0 mmol) in dichloromethane (20 mL) was added tert-butyldiphenylchlorosilane (4.4 g, 16.01 mmol) at 0° C. After addition, the reaction mixture was stirred at 25° C. for 16 h and subsequently concentrated under reduced pressure. The residue was purified by column chromatography (silica gel, 100-200 mesh, petroleum ether) to afford 2-bromoethoxy-tert-butyl-diphenyl-silane (3.1 g, 53%) as colorless oil. $^1$H NMR (400 MHz, CDCl$_3$) δ 7.68 (m, 4H), 7.47-7.37 (m, 6H), 3.93 (t, J=6.4 Hz, 2H), 3.43 (t, J=6.5 Hz, 2H), 1.08 (s, 9H).

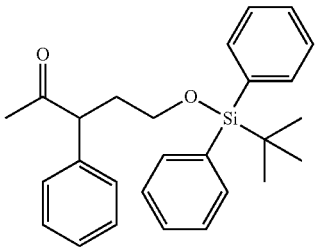 [SMILES: CC(=O)C(CCO[Si](c1ccccc1)(c1ccccc1)C(C)(C)C)c1ccccc1]

Step 2: 5-((tert-butyldiphenylsilyl)oxy)-3-phenyl-pentan-2-one

To a solution of phenylacetone (10.0 g, 74.5 mmol) in N,N-dimethylformamide (20 mL) was added sodium hydride (60%, 4.5 g, 111.8 mmol) at 0° C. After addition, the mixture was stirred at 25° C. for 15 min and 2-bromoethoxy-tert-butyl-diphenyl-silane (32.5 g, 89.4 mmol) was added. The resulting mixture was stirred at 25° C. for 18 h and subsequently quenched by addition of water (100 mL). The mixture was extracted with ethyl acetate (3×100 mL). The combined organic layers were washed with water (20 mL), brine (20 mL), dried over anhydrous sodium sulfate and concentrated under reduced pressure. The residue was purified by column chromatography (silica gel, 100-200 mesh, 0 to 20% ethyl acetate in petroleum ether) to afford 5-[tert-butyl(diphenyl)silyl]oxy-3-phenyl-pentan-2-one as yellow oil (6.0 g, 19%). $^1$H NMR (400 MHz, CDCl$_3$) δ 7.65-7.55 (m, 4H), 7.44-7.26 (m, 9H), 7.22-7.15 (m, 2H), 3.99 (t, J=7.2

Hz, 1H), 3.65-3.58 (m, 1H), 3.65-3.75 (m, 1H), 2.40-2.28 (m, 1H), 2.05 (s, 3H), 1.90-1.80 (m, 1H), 1.05 (s, 9H).

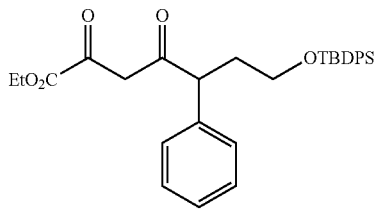

Step 3: ethyl 7-((tert-butyldiphenylsilyl)oxy)-2,4-dioxo-5-phenylheptanoate

To a solution of 5-[tert-butyl(diphenyl)silyl]oxy-3-phenyl-pentan-2-one (5.75 g, 13.8 mmol) in tetrahydrofuran (60 mL) was added potassium tert-butoxide (1.0 M in tetrahydrofuran, 20.7 mL, 20.7 mmol) at 0° C. After addition, the mixture was stirred at 25° C. for 30 min and diethyl oxalate (3.0 g, 20.7 mmol) was added. The resulting mixture was stirred at 25° C. for 2 h and concentrated under reduced pressure. The residue was purified by column chromatography (silica gel, 100-200 mesh, 0 to 50% ethyl acetate in petroleum ether) to afford ethyl 7-[tert-butyl(diphenyl)silyl]oxy-2,4-dioxo-5-phenyl-heptanoate as a brown oil (6.0 g, 84%), used as is in the next step.

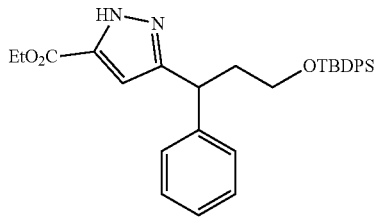

Step 4: ethyl 3-(3-((tert-butyldiphenylsilyl)oxy)-1-phenylpropyl)-1H-pyrazole-5-carboxylate A mixture of hydrazine monohydrate (684 mg, 11.6 mmol) and ethyl 7-[tert-butyl(diphenyl)silyl]oxy-2,4-dioxo-5-phenyl-heptanoate (6.0 g, 11.6 mmol) in ethanol (120 mL) was stirred at 25° C. for 5 h and concentrated under reduced pressure. The residue was purified by column chromatography (silica gel, 100-200 mesh, 0 to 50% ethyl acetate in petroleum ether) to afford ethyl 3-[3-[tert-butyl(diphenyl)silyl]oxy-1-phenyl-propyl]-1H-pyrazole-5-carboxylate (1.8 g, 30%) as a light yellow oil. LCMS $R_T$=1.036 min, m/z=513.1 [M+H]⁻.

LCMS (5 to 95% acetonitrile in water+0.03% trifluoroacetic acid over 1.5 mins) retention time 1.036 min, ESI+ found [M+H]=513.1.

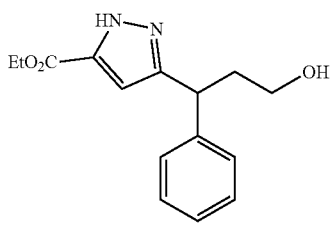 [SMILES: CCOC(=O)c1cc(C(CCO)c2ccccc2)n[nH]1]

Step 5: ethyl 3-(3-hydroxy-1-phenylpropyl)-1H-pyrazole-5-carboxylate

To a solution of ethyl 3-[3-[tert-butyl(diphenyl)silyl]oxy-1-phenyl-propyl]-1H-pyrazole-5-carboxylate (1.80 g, 3.5 mmol) in tetrahydrofuran (40 mL) was added tetrabutylammonium fluoride (1.0 N in tetrahydrofuran, 3.9 mL, 3.9 mmol). The mixture was stirred at 25° C. for 5 h and then concentrated under reduced pressure. The residue was purified by column chromatography (silica gel, 100-200 mesh, 0 to 50% ethyl acetate in petroleum ether) to afford ethyl 3-(3-hydroxy-1-phenyl-propyl)-1H-pyrazole-5-carboxylate as a light yellow oil (800 mg, 83%), used as is in the next step.

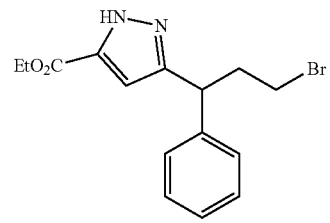 [SMILES: CCOC(=O)c1cc(C(CCBr)c2ccccc2)n[nH]1]

Step 6: ethyl 3-(3-bromo-1-phenylpropyl)-1H-pyrazole-5-carboxylate

A mixture of phosphorusoxybromide (815 mg, 2.84 mmol) and ethyl 5-(3-hydroxy-1-phenyl-propyl)-1H-pyrazole-3-carboxylate (650 mg, 2.37 mmol) in acetonitrile (20 mL) was heated at 50° C. for 15 h and subsequently concentrated under reduced pressure to afford crude ethyl 5-(3-bromo-1-phenyl-propyl)-1H-pyrazole-3-carboxylate as brown solid (790 mg, 98%). This crude was used in the next step without further purification.

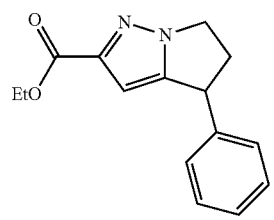 [SMILES: CCOC(=O)c1cc2n(n1)CCC2c1ccccc1]

Step 7: ethyl 4-phenyl-5,6-dihydro-4H-pyrrolo[1,2-b]pyrazole-2-carboxylate

A mixture of ethyl 5-(3-bromo-1-phenyl-propyl)-1H-pyrazole-3-carboxylate (790 mg, 2.34 mmol) and potassium carbonate (2.59 g, 18.74 mmol) in N,N-dimethylformamide (20 mL) was stirred at 25° C. for 5 h and filtered. The filtrate was concentrated under reduced pressure and the residue was purified by preparative TLC (50% ethyl acetate in petroleum ether, $R_f$=0.5) to afford ethyl 4-phenyl-5,6-dihydro-4H-pyrrolo[1,2-b]pyrazole-2-carboxylate (400 mg, 67%) as a brown oil. LCMS $R_T$=0.850 min, m/z=257.0 [M+H]⁺.

LCMS (5 to 95% acetonitrile in water+0.03% trifluoroacetic acid over 1.5 mins) retention time 0.850 min, ESI+ found [M+H]=257.0.

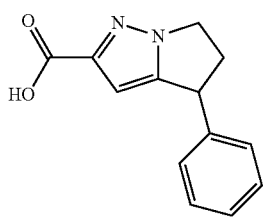 [SMILES: O=C(O)c1cc2n(n1)CCC2c1ccccc1]

Step 8: 4-phenyl-5,6-dihydro-4H-pyrrolo[1,2-b]pyrazole-2-carboxylic acid

A mixture of ethyl 4-phenyl-5,6-dihydro-4H-pyrrolo[1,2-b]pyrazole-2-carboxylate (400 mg, 1.56 mmol) and lithium hydroxide monohydrate (196 mg, 4.68 mmol) in tetrahydrofuran (8 mL)/water (2 mL) was stirred at 25° C. for 2 h and concentrated under reduced pressure. The residue was adjusted to pH=5 by addition of hydrochloric acid (2 N). The resulting mixture was extracted with ethyl acetate (3×10 mL). The combined organic layers were washed with water (20 mL), brine (20 mL), dried over anhydrous sodium sulfate and concentrated under reduced pressure to afford crude 4-phenyl-5,6-dihydro-4H-pyrrolo[1,2-b]pyrazole-2-carboxylic acid as a brown solid (340 mg, 95%), used in the next step without further purification.

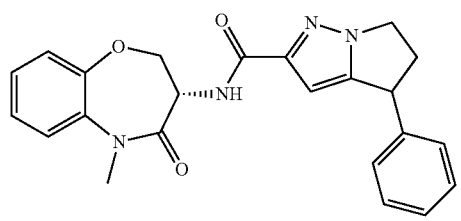 [SMILES: CN1C(=O)[C@@H](NC(=O)c2cc3n(n2)CCC3c2ccccc2)COc2ccccc21]

Step 9: 4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide A mixture of 4-phenyl-5,6-dihydro-4H-pyrrolo[1,2-b]pyrazole-2-carboxylic acid (25 mg, 0.11 mmol), 1-hydroxybenzotriazole (15 mg, 0.11 mmol), 1-(3-dimethylaminopropyl)-3-ethylcarbodiimidehydrochloride (21 mg, 0.11 mmol) and (3S)-3-amino-5-methyl-2,3-dihydro-1,5-benzoxazepin-4-one (21 mg, 0.11 mmol) in N,N-dimethylformamide (3 mL) was stirred at 25° C. for 15 h. The mixture was concentrated under reduced pressure. The residue was purified by RP-HPLC (acetonitrile 45-75/0.05% ammonia hydroxide in water) to afford 4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide (13 mg, 29%) as a white solid. $^1$H NMR (400 MHz, CD$_3$OD): δ 7.50-7.40 (m, 1H), 7.37-7.20 (m, 8H), 6.38 (s, 1H), 5.02-4.96 (m, 1H), 4.65-4.56 (m, 1H), 4.55-4.46 (m, 1H), 4.45-4.27 (m, 2H), 4.25-4.18 (m, 1H), 3.42 (s, 3H), 3.15-3.09 (m, 1H), 2.56-2.52 (m, 1H). LCMS R$_T$=0.875 min, m/z=403.1 [M+H]$^+$.

LCMS (5 to 95% acetonitrile in water+0.03% trifluoroacetic acid over 1.5 mins) retention time 0.875 min, ESI+ found [M+H]=403.1.

Step 10: (4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide

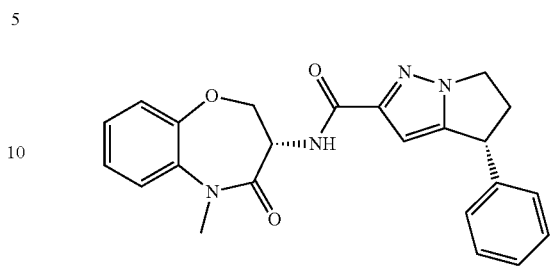

N-[(3S)-5-methyl-4-oxo-2,3-dihydro-1,5-benzoxazepin-3-yl]-4-phenyl-5,6-dihydro-4H-pyrrolo[1,2-b]pyrazole-2-carboxamide (120 mg, 0.3 mmol) was separated by chiral SFC to afford arbitrarily assigned: (4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide (peak 2, retention time=5.106 min) (32.3 mg, 26%) as a yellow solid. $^1$H NMR (400 MHz, CD$_3$OD) δ 7.45-7.42 (m, 1H), 7.35-7.29 (m, 4H), 7.25-7.20 (m, 4H), 6.37 (s, 1H), 4.99-4.96 (m, 1H), 4.59-4.56 (m, 1H), 4.52-4.48 (m, 1H), 4.42-4.34 (m, 2H), 4.25-4.20 (m, 1H), 3.42 (s, 3H), 3.15-3.10 (m 1H), 2.56-2.51 (m, 1H). LCMS R$_T$=1.960 min, m/z=403.2 [M+H]$^+$.

LCMS (10 to 80% acetonitrile in water+0.03% ammonium bicarbonate over 3.0 mins) retention time 1.960 min, ESI+ found [M+H]=403.2.

SFC condition: Column: Lux Cellulose-2 150×4.6 mm I.D., 3 μm, mobile phase: 40% of Methanol (0.05% DEA) in CO$_2$, Flow rate: 2.5 mL/min, Column temperature: 40° C.

Example #11

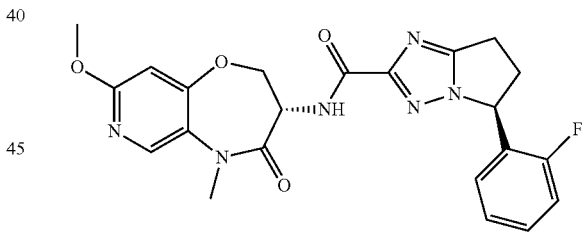

(5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide

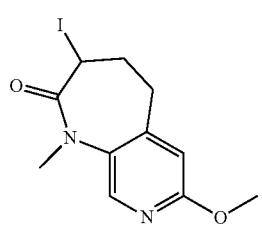 [SMILES: COc1cc2c(cn1)N(C)C(=O)C(I)CC2]

Step 1: 3-iodo-7-methoxy-1-methyl-4,5-dihydro-3H-pyrido[3,4-b]azepin-2-one

To a solution of 7-methoxy-1-methyl-4,5-dihydro-3H-pyrido[3,4-b]azepin-2-one (150 mg, 0.73 mmol) in dichloromethane (15 mL) was added $N^1,N^1,N^2,N^2$-tetramethylethane-1,2-diamine (845 mg, 7.27 mmol) at −15° C., then iodotrimethylsilane (1.49 g, 7.27 mmol) was added slowly. The mixture was stirred at −15° C. for 2 h and iodine (738 mg, 2.91 mmol) was added. The resulting mixture was stirred at 0° C. for 2 h and quenched by addition of aqueous sodium thiosulfate (10 mL). The mixture was extracted with dichloromethane (3×20 mL). The combined organic layers were washed with water (10 mL), brine (10 mL), dried over sodium sulfate and concentrated under reduced pressure. The residue was purified by column chromatography (silica gel, 100-200 mesh, 0 to 5% methanol in dichloromethane) to afford 3-iodo-7-methoxy-1-methyl-4,5-dihydro-3H-pyrido[3,4-b]azepin-2-one (220 mg, 91%) as a yellow oil. LCMS $R_T$=0.696 min, m/z=332.8 [M+H]$^+$.

LCMS (5 to 95% acetonitrile in water+0.03% trifluoroacetic acid over 1.5 mins) retention time 0.696 min, ESI+ found [M+H]=332.8.

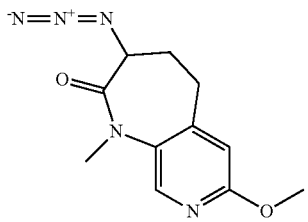

Step 2: 3-azido-7-methoxy-1-methyl-4,5-dihydro-3H-pyrido[3,4-b]azepin-2-one

To a solution of 3-iodo-7-methoxy-1-methyl-4,5-dihydro-3H-pyrido[3,4-b]azepin-2-one (220 mg, 0.66 mmol) in dichloromethane (15 mL) was added sodium azide (140 mg, 2.15 mmol). The reaction mixture was stirred at 25° C. for 2 h and diluted with water (20 mL). The mixture was extracted with ethyl acetate (3×20 mL). The combined organic layers were washed with water (20 mL), brine (20 mL), dried over anhydrous sodium sulfate and concentrated under reduced pressure to afford crude 3-azido-7-methoxy-1-methyl-4,5-dihydro-3H-pyrido[3,4-b]azepin-2-one (150 mg, 92%) as a yellow oil, used as is in the next step. LCMS $R_T$=0.667 min, m/z=248.0 [M+H]$^+$.

LCMS (5 to 95% acetonitrile in water+0.03% trifluoroacetic acid over 1.5 mins) retention time 0.667 min, ESI+ found [M+H]=248.0.

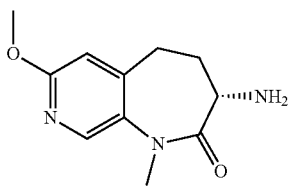

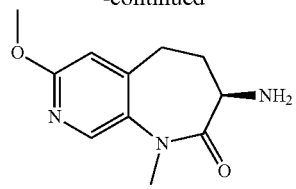

Step 3: (S)-3-amino-7-methoxy-1-methyl-4,5-dihydro-3H-pyrido[3,4-b]azepin-2-one and (R)-3-amino-7-methoxy-1-methyl-4,5-dihydro-3H-pyrido[3,4-b]azepin-2-one A mixture of 3-azido-7-methoxy-1-methyl-4,5-dihydro-3H-pyrido[3,4-b]azepin-2-one (150 mg, 0.61 mmol) and palladium (10% on carbon, 129 mg) in methanol (20 mL) was hydrogenated (15 psi) at 25° C. for 2 h and filtered. The filtrate was concentrated under reduced pressure to afford crude 3-amino-7-methoxy-1-methyl-4,5-dihydro-3H-pyrido[3,4-b]azepin-2-one (120 mg, 89%) as a colorless oil.

LCMS $R_T$=1.342 min, m/z=222.2 [M+H]$^+$.

LCMS (0 to 60% acetonitrile in water+0.05% ammonium hydroxide over 3 minutes) retention time 1.342 min, ESI+ found [M+H]=222.2

Racemic 3-amino-7-methoxy-1-methyl-4,5-dihydro-3H-pyrido[3,4-b]azepin-2-one was separated by chiral SFC to afford arbitrarily assigned:

(S)-3-amino-7-methoxy-1-methyl-4,5-dihydro-3H-pyrido[3,4-b]azepin-2-one (peak 1, retention time=5.1566.794 min) (45.0 mg, 38%) as a yellow oil.

(R)-3-amino-7-methoxy-1-methyl-4,5-dihydro-3H-pyrido[3,4-b]azepin-2-one (peak 2, retention time=6.794 min) (45.0 mg, 38%) as a yellow oil.

SFC conditions: Column: ChiralPak AD-3 150×4.6 mm I.D., 3 um; Mobile phase: A: $CO_2$ B: Methanol (0.05% DEA); Gradient: from 5% to 40% of B in 5.5 min and hold 40% for 3 min, then 5% of B for 1.5 min; Flow rate: 2.5 mL/min; Column temperature: 40° C.

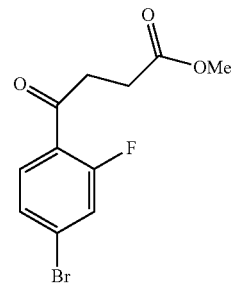 [SMILES: COC(=O)CCC(=O)c1ccc(Br)cc1F]

Step 4: methyl 4-(4-bromo-2-fluorophenyl)-4-oxobutanoate

To a solution of 1-bromo-3-fluorobenzene (5.0 g, 28.57 mmol) in 1,2-dichloroethane (100 mL) was added aluminumchloride (15.2 g, 114.29 mmol) and methyl 4-chloro-4-oxobutyrate (8.6 g, 57.14 mmol). The mixture was heated at 70° C. for 12 h and cooled. The reaction was slowly quenched by addition of water (20 mL) and extracted with dichloromethane (2×100 mL). The combined organic layers were concentrated under reduced pressure and the residue was purified by column chromatography (silica gel, 100-200 mesh, 0 to 20% ethyl acetate in petroleum ether) to afford methyl 4-(4-bromo-2-fluoro-phenyl)-4-oxo-butanoate (2.0 g, 24%) as a yellow solid. LCMS $R_T$=0.995 min, m/z=291.1 [M+H]⁺.

LCMS (10 to 80% acetonitrile in water+0.03% trifluoacetic acid over 2.0 mins) retention time 0.995 min, ESI+ found [M+H]=291.1

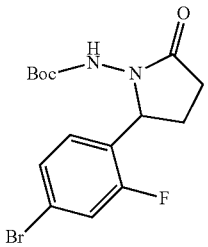 [SMILES: CC(C)(C)OC(=O)NN1C(=O)CCC1c1ccc(Br)cc1F]

Step 5: tert-butyl (2-(4-bromo-2-fluorophenyl)-5-oxopyrrolidin-1-yl)carbamate

To a solution of methyl 4-(4-bromo-2-fluoro-phenyl)-4-oxo-butanoate (2.0 g, 6.91 mmol) in tetrahydrofuran (10 mL) and acetic acid (5 mL) was added tert-butyl hydrazinecarboxylate (1.3 g, 10.38 mmol). The mixture was stirred at 40° C. for 12 h and then sodiumcyanoborohydride (652 mg, 10.38 mmol) was added. Stirring was continued for another 6 h and the mixture was concentrated under reduced pressure. The residue was diluted with ethyl acetate (50 mL), washed with water (2×20 mL), brine (20 mL), dried over sodium sulfate and concentrated under reduced pressure. The residue was purified by column chromatography (silica gel, 100-200 mesh, 0 to 100% ethyl acetate in petroleum ether) to afford tert-butyl N-[2-(2-fluorophenyl)-5-oxo-pyrrolidin-1-yl]carbamate (800 mg, 78%) as yellow oil. LCMS $R_T$=1.067 min, m/z=319.0 [M+H]⁺.

LCMS (10 to 80% acetonitrile in water+0.03% trifluoacetic acid over 2.0 mins) retention time 1.067 min, ESI+ found [M−55]=319.0

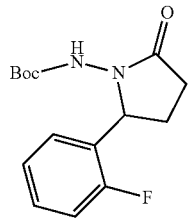 [SMILES: CC(C)(C)OC(=O)NN1C(=O)CCC1c1ccccc1F]

Step 6: tert-butyl (2-(2-fluorophenyl)-5-oxopyrrolidin-1-yl)carbamate

A mixture of tert-butyl N-[2-(4-bromo-2-fluoro-phenyl)-5-oxo-pyrrolidin-1-yl]carbamate (800 mg, 2.14 mmol) and Pd/C (10%, 228 mg, 0.21 mmol) in methanol (10 mL) was hydrogenated (15 psi) at 25° C. for 4 h and then filtered. The filtrate was concentrated under reduced pressure to afford crude tert-butyl N-[2-(2-fluorophenyl)-5-oxo-pyrrolidin-1-yl]carbamate (500 mg, 79%) as a white solid.
LCMS $R_T$=0.972 min, m/z=239.1 [M+H]⁺.

LCMS (10 to 80% acetonitrile in water+0.03% trifluoacetic acid over 2.0 mins) retention time 0.972 min, ESI+ found [M−55]=239.1

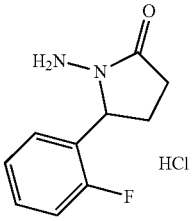 [SMILES: NN1C(=O)CCC1c1ccccc1F ; Cl]

Step 7: 1-amino-5-(2-fluorophenyl)pyrrolidin-2-one hydrochloride

A solution of tert-butyl (2-(2-fluorophenyl)-5-oxopyrrolidin-1-yl)carbamate (400 mg, 1.36 mmol) in ethyl acetate (5 mL) was added HCl (4N in ethyl acetate, 1.0 mL, 4.0 mmol). The mixture was stirred at 25° C. for 4 h and then concentrated under reduced pressure to afford crude 1-amino-5-(2-fluorophenyl)pyrrolidin-2-one hydrochloride (400 mg, 100%) as white solid, used as is in the next step.

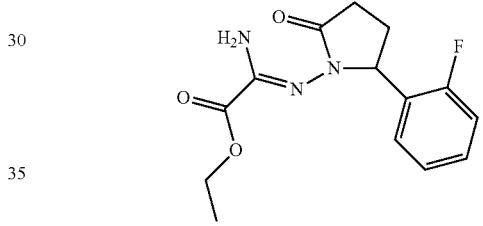

Step 8: (Z)-ethyl 2-amino-2-((2-(2-fluorophenyl)-5-oxopyrrolidin-1-yl)imino)acetate To a solution of 1-amino-5-(2-fluorophenyl)pyrrolidin-2-one hydrochloride (400 mg, 2.06 mmol) in ethanol (10 mL) was added ethyl 2-ethoxy-2-imino-acetate (1.8 g, 12.36 mmol). The mixture was stirred at 40° C. for 12 h and concentrated under reduced pressure to afford crude ethyl (2Z)-2-amino-2-[2-(2-fluorophenyl)-5-oxo-pyrrolidin-1-yl] imino-acetate (500 mg, 82%) as a yellow oil, used as is in the next step.

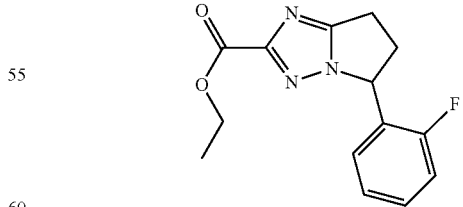

Step 9: methyl 7-methyl-5,6,7,8-tetrahydroimidazo [1,5-a]pyridine-1-carboxylate

A solution of ethyl (2Z)-2-amino-2-[2-(2-fluorophenyl)-5-oxo-pyrrolidin-1-yl]imino-acetate (500 mg, 1.7 mmol) in phosphorus oxychloride (5.0 mL, 135.9 mmol) was heated at 120° C. for 1 h. After cooled, the mixture was slowly quenched by addition of water (20 mL) and extracted with dichloromethane (3×20 mL). The combined organic layers were washed with 20% sodium bicarbonate (20 mL), brine (30 mL), dried over sodium sulfate and concentrated under reduced pressure. The residue was purified by column chromatography (silica gel, 100-200 mesh, 0 to 60% ethyl acetate in petroleum ether) to afford ethyl 5-(2-fluorophenyl)-6,7-dihydro-5H-pyrrolo[1,2-b][1,2,4]triazole-2-carboxylate (400 mg, 85%) as a light yellow oil. LCMS $R_T$=0.760 min, m/z=275.9 [M+H]$^+$.

LCMS (5 to 95% acetonitrile in water+0.03% trifluoacetic acid over 1.5 mins) retention time 0.760 min, ESI+ found [M+H]=275.9

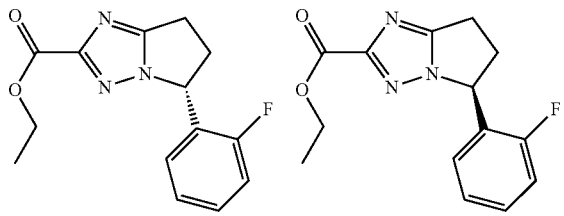

Step 10: (R)-ethyl 5-(2-fluorophenyl)-6,7-dihydro-5H-pyrrolo[1,2-b][1,2,4]triazole-2-carboxylate and (S)-ethyl 5-(2-fluorophenyl)-6,7-dihydro-5H-pyrrolo[1,2-b][1,2,4]triazole-2-carboxylate Racemic ethyl 5-(2-fluorophenyl)-6,7-dihydro-5H-pyrrolo[1,2-b][1,2,4]triazole-2-carboxylate (7.1 g, 25.79 mmol) was separated by chiral SFC to afford arbitrarily assigned:

(R)-ethyl 5-(2-fluorophenyl)-6,7-dihydro-5H-pyrrolo[1,2-b][1,2,4]triazole-2-carboxylate (Peak 1, Retention time=3.325 min) (3.0 g, 42%) as a yellow oil.

(S)-ethyl 5-(2-fluorophenyl)-6,7-dihydro-5H-pyrrolo[1,2-b][1,2,4]triazole-2-carboxylate (Peak 2, Retention time=3.560 min) (2.8 g, 39%) as a yellow oil.

SFC condition: Column: ChiralPak AD-3 150×4.6 mm I.D., 3 um Mobile phase: A: CO2 B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

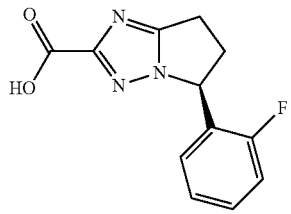 [SMILES: O=C(O)c1nc2n(n1)[C@H](c1ccccc1F)CC2]

Step 11: (S)-5-(2-fluorophenyl)-6,7-dihydro-5H-pyrrolo[1,2-b][1,2,4]triazole-2-carboxylic acid To a solution of ethyl (5S)-5-(2-fluorophenyl)-6,7-dihydro-5H-pyrrolo[1,2-b][1,2,4]triazole-2-carboxylate (2.0 g, 7.27 mmol) in tetrahydrofuran (50 mL)/water (10 mL) was added lithium hydroxide hydrate (870 mg, 36.33 mmol) portion-wise. The reaction mixture was stirred at 25° C. for 12 h and then concentrated under reduce pressure. The aqueous residue was diluted with ice water (20 mL) and adjusted to pH=3 by addition of hydrochloric acid (1 N). The solid product was collected by filtration and dried in vacuo to afford crude (5S)-5-(2-fluorophenyl)-6,7-dihydro-5H-pyrrolo[1,2-b][1,2,4]triazole-2-carboxylic acid (1.6 g, 89%) as a white solid used as is in the next step. $^1$H NMR (400 MHz, DMSO-d$_6$) δ 13.19 (br s, 1H), 7.48-7.40 (m, 1H), 7.31-7.20 (m, 3H), 5.80-5.76 (m, 1H), 3.25-3.17 (m, 1H), 3.11-2.97 (m, 2H), 2.64-2.58 (m, 1H). LCMS $R_T$=0.586 min, m/z=248.0 [M+H]$^+$.

LCMS (5 to 95% acetonitrile in water+0.03% trifluoroacetic acid over 1.5 mins) retention time 0.586 min, ESI+ found [M+H]=248.0.

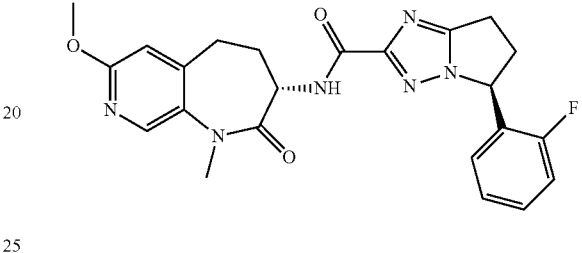

Step 12: (5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide A mixture of (S)-3-amino-7-methoxy-1-methyl-4,5-dihydro-3H-pyrido[3,4-b]azepin-2-one (15 mg, 0.07 mmol), 1-(3-dimethylaminopropyl)-3-ethylcarbodiimide hydrochloride (16 mg, 0.08 mmol), 1-hydroxybenzotriazole (11 mg, 0.08 mmol) and (5S)-5-(2-fluorophenyl)-6,7-dihydro-5H-pyrrolo[1,2-b][1,2,4]triazole-2-carboxylic acid (20 mg, 0.08 mmol) in N,N-dimethylformamide (3 mL) was stirred at 25° C. for 2 h. The reaction mixture was concentrated under reduced pressure. The residue was purified by RP-HPLC (acetonitrile 30-60%/0.05% ammonium hydroxide in water) to afford (5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide (9.2 mg, 30%) as a white solid. $^1$H NMR (400 MHz, CD$_3$OD) δ 8.14 (s, 1H), 7.43-7.36 (m, 1H), 7.22-7.13 (m, 3H), 6.78 (s, 1H), 5.79-5.74 (m, 1H), 4.56-4.50 (m, 1H), 3.93 (s, 3H), 3.40 (s, 3H), 3.34-3.29 (m, 1H), 3.13-3.08 (m, 2H), 2.85-2.81 (m, 1H), 2.76-2.70 (m, 2H), 2.54-2.48 (m, 1H), 2.18-2.13 (m, 1H). LCMS $R_T$=0.818 min, m/z=451.0 [M+H]+.

LCMS (5 to 95% acetonitrile in water+0.1% formic acid over 1.5 mins) retention time: 0.818 min, ESI+ found [M+H]=451.0.

Example #12

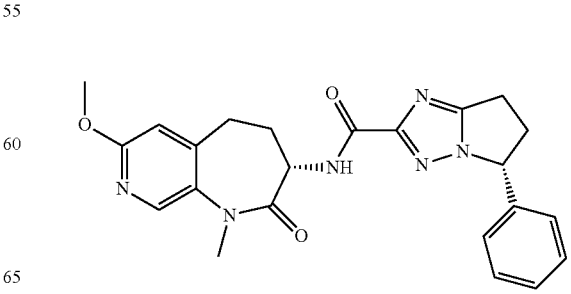

(5R)—N-[(3S)-7-methoxy-1-methyl-2-oxo-4,5-di-hydro-3H-pyrido[3,4-b]azepin-3-yl]-5-phenyl-6,7-dihydro-5H-pyrrolo[1,2-b][1,2,4]triazole-2-carboxamide

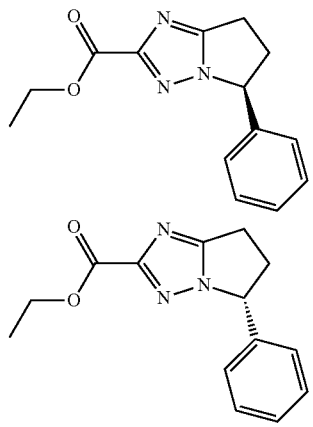

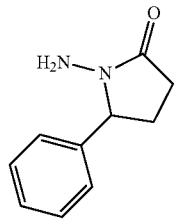 [SMILES: NN1C(=O)CCC1c1ccccc1]

Step 1: 1-amino-5-phenyl-pyrrolidin-2-one

To a solution of tert-butyl N-(2-oxo-5-phenyl-pyrrolidin-1-yl)carbamate (350 mg, 1.3 mmol) in ethyl acetate (3 mL) was added HCl (4N in ethyl acetate, 3.0 mL, 12.0 mmol). The mixture was stirred at 20° C. for 1 h and concentrated under reduced pressure. The residue was quenched by addition of saturated sodium bicarbonate (10 mL) and extracted with ethyl acetate (3×10 mL). The combined organic layers were washed with water (3×20 mL), brine (2×20 mL), dried over sodium sulfate and concentrated under reduced pressure to give crude 1-amino-5-phenyl-pyrrolidin-2-one (190 mg, 85%) as a white solid. $^1$H NMR (400 MHz, CDCl$_3$): δ7.42-7.32 (m, 3H), 7.24 (d, J=7.6 Hz, 2H), 4.66-4.62 (m, 1H), 3.95 (br. s., 2H), 2.63-2.45 (m, 3H), 1.91-1.88 (m, 1H).

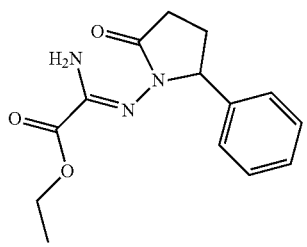 [SMILES: CCOC(=O)/C(N)=N/N1C(=O)CCC1c1ccccc1]

Step 2: ethyl (2Z)-2-amino-2-(2-oxo-5-phenyl-pyrrolidin-1-yl)imino-acetate

To a stirred solution of 1-amino-5-phenyl-pyrrolidin-2-one (270 mg, 1.53 mmol) in ethanol (8.0 mL) was added ethyl amino (thioxo)acetate (224 mg, 1.69 mmol). The mixture was stirred at 90° C. for 4 h and cooled to room temperature. The solution was diluted with ethyl acetate (15 mL), washed with water (2×5 mL), brine (10 mL), dried over sodium sulfate and concentrated under reduced pressure to give crude ethyl (2Z)-2-amino-2-(2-oxo-5-phenyl-pyrrolidin-1-yl)imino-acetate (400 mg, 95%) as a yellow oil. LCMS R$_T$=0.581 min, m/z=275.9 [M+H]$^+$.

LCMS (5 to 95% acetonitrile in water+0.03% trifluoacetic acid over 1.5 mins) retention time 0.581 min, ESI+ found [M+H]=275.9.

Step 3: (S)-ethyl 5-phenyl-6,7-dihydro-5H-pyrrolo[1,2-b][1,2,4]triazole-2-carboxylate and (R)-ethyl 5-phenyl-6,7-dihydro-5H-pyrrolo[1,2-b][1,2,4]triazole-2-carboxylate A solution of ethyl (2Z)-2-amino-2-(2-oxo-5-phenyl-pyrrolidin-1-yl)imino-acetate (400 mg, 1.45 mmol) in POCl$_3$ (2 mL) was stirred at 120° C. for 1 h. After cooled, the mixture was quenched by addition of saturated sodium bicarbonate (15 mL). The resulting solution was extracted with ethyl acetate (3×10 mL). The combined organic layers were washed with brine (15 mL), dried over sodium sulfate and concentrated under reduced pressure. The residue was purified by column chromatography (silica gel, 100-200 mesh, 0-70% ethyl acetate in petroleum) to afford ethyl 5-phenyl-6,7-dihydro-5H-pyrrolo[1,2-b][1,2,4]triazole-2-carboxylate (310 mg, 81%) as a yellow oil.

The racemic material was separated by chiral SFC to give:
(S)-ethyl 5-phenyl-6,7-dihydro-5H-pyrrolo[1,2-b][1,2,4]triazole-2-carboxylate (Peak 1, retention time=4.063 min) (130 mg, 42%) as a yellow oil. LCMS R$_T$=0.629 min, m/z=257.8 [M+H]$^+$.

LCMS (5 to 95% acetonitrile in water+0.03% trifluoacetic acid over 1.5 mins) retention time 0.629 min, ESI+ found [M+H]=257.8.

(R)-ethyl 5-phenyl-6,7-dihydro-5H-pyrrolo[1,2-b][1,2,4]triazole-2-carboxylate (Peak 1, retention time=5.844 min) (135 mg, 43%) as a yellow oil. LCMS R$_T$=0.631 min, m/z=257.8 [M+H]$^+$.

LCMS (5 to 95% acetonitrile in water+0.03% trifluoacetic acid over 1.5 mins) retention time 0.631 min, ESI+ found [M+H]=257.8.

SFC condition: column: Lux Cellulose-2 150×4.6 mm I.D., 3 μm mobile phase: A: CO2; B: MeOH (0.05% DEA) gradient: from 5 to 40 of B in 4.5 min and hold 40% for 2.5 min, then 5% of B for 1 min. Flow rate: 2.8 mL/min. Column temperature: 40° C.

Step 4: (5R)—N-[(3S)-7-methoxy-1-methyl-2-oxo-4,5-dihydro-3H-pyrido[3,4-b]azepin-3-yl]-5-phenyl-6,7-dihydro-5H-pyrrolo[1,2-b][1,2,4]triazole-2-carboxamide A mixture of (S)-3-amino-7-methoxy-1-methyl-4,5-dihydro-3H-pyrido[3,4-b]azepin-2-one (15 mg, 0.07 mmol), (5R)-5-phenyl-6,7-dihydro-5H-pyrrolo[1,2-b][1,2,4]triazole-2-carboxylic acid (19 mg, 0.08 mmol), 1-hydroxybenzotriazole (11 mg, 0.08 mmol) and 1-(3-dimethylaminopropyl)-3-ethylcarbodiimide hydrochloride (16 mg, 0.08 mmol) in N,N-dimethylformamide (3 mL) was stirred at 25° C. for 2 h and concentrated under reduced pressure. The residue was purified by RP-HPLC (acetonitrile 30-60%/0.05% ammonium hydroxide in water) to afford (5R)—N-[(3S)-7-methoxy-1-methyl-2-oxo-4,5-dihydro-3H-pyrido[3,4-b]azepin-3-yl]-5-phenyl-6,7-dihydro-5H-pyrrolo[1,2-b][1,2,4]triazole-2-carboxamide (20 mg, 68%) as a white solid. $^1$H NMR (400 MHz, CD$_3$OD) δ 8.13 (s, 1H), 7.40-7.34 (m, 3H), 7.21-7.20 (m, 2H), 6.77 (s, 1H), 5.55-5.51 (m, 1H), 4.54-4.49 (m, 1H), 3.92 (s, 3H), 3.39 (s, 3H), 3.30-3.24 (m, 1H), 3.06-3.04 (m, 2H), 2.81-2.70 (m, 3H), 2.50-2.48 (m, 1H), 2.15-2.13 (m, 1H). LC-MS R$_T$=0.731 min, m/z=433.0 [M+H]$^+$.

LCMS (5 to 95% acetonitrile in water+0.03% trifluoacetic acid over 1.5 mins) retention time 0.731 min, ESI+ found [M+H]=433.0.

Example #13

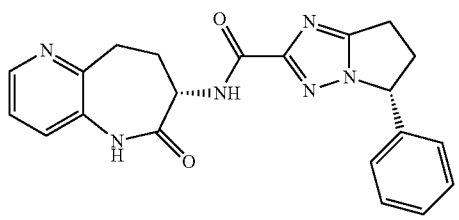 [SMILES: O=C(N[C@H]1CCc2ncccc2NC1=O)c1nc2n(n1)[C@@H](c1ccccc1)CC2]

(5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide

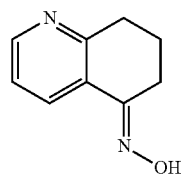 [SMILES: O/N=C1\CCCc2ncccc21]

Step 1: (E)-7,8-dihydroquinolin-5(6H)-one oxime

To a solution of 5,6,7,8-tetrahydroquinolinone-5 (5.0 g, 34.0 mmol) in methanol (30 mL) and water (9 mL) were added hydroxylamine hydrochloride (7.1 g, 101.9 mmol) and sodium acetate (8.4 g, 101.9 mmol). The mixture was stirred at 80° C. for 4 h and concentrated under reduced pressure. The aqueous residue was diluted with water (80 mL) and the formed solid was collected by filtration. The solid was triturated with hexanes (20 mL) and dried in vacuo to give crude 7,8-dihydro-6H-quinolin-5-one oxime (4.80 g, 87%) as a light green solid, used in the next step without further purification.

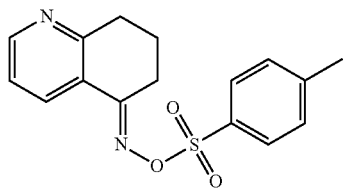 [SMILES: Cc1ccc(S(=O)(=O)O/N=C2\CCCc3ncccc32)cc1]

Step 2: (E)-7,8-dihydroquinolin-5(6H)-one O-tosyl oxime

To a solution of 7,8-dihydro-6H-quinolin-5-one oxime (4.8 g, 29.6 mmol) in acetone (220 mL) and water (90 mL) was added 4-methylbenzene-1-sulfonyl chloride (8.5 g, 44.4 mmol) and potassium hydroxide (1.7 g, 29.6 mmol). The mixture was heated at reflux for 1 h and concentrated under reduced pressure. The resulting solid was washed with water (50 mL) and dried in vacuo to afford crude (E)-7,8-dihydroquinolin-5(6H)-one O-tosyl oxime (8.4 g, 90%) as a light red solid, used in the next step without further purification. LCMS: R$_T$=0.661 min, m/z=317.0 [M+H]$^+$.

LCMS (5 to 95% acetonitrile in water+0.1% formic acid over 1.5 mins) retention time: 0.661 min, ESI+ found [M+H]=317.0.

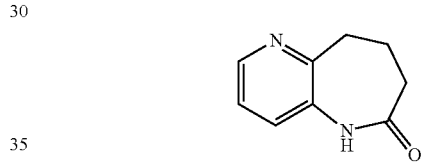

Step 3: 8,9-dihydro-5H-pyrido[3,2-b]azepin-6(7H)-one

A mixture of [(E)-7,8-dihydro-6H-quinolin-5-ylideneamino] 4-methyl benzenesulfonate (8.40 g, 26.6 mmol) and potassium acetate (7.82 g, 79.7 mmol) in ethanol (120 mL) and water (240 mL) was heated at reflux for 17 h and concentrated under reduced pressure. The remaining aqueous solution was adjusted to pH=10 by addition of aqueous sodium hydroxide (10 N) and then extracted with chloroform (3×150 mL). The combined organic layers were dried over sodium sulfate and concentrated under reduced pressure. The residue was purified by column chromatography (silica gel, 100-200 mesh, 0 to 100% ethyl acetate in petroleum ether) to afford 5,7,8,9-tetrahydropyrido[3,2-b]azepin-6-one (2.30 g, 53%) as a brown solid, used in the next step as is. $^1$H NMR (400 MHz, CD$_3$Cl) δ 8.38-8.35 (m, 1H), 8.27 (br. s, 1H), 7.32-7.29 (m, 1H), 7.22-7.20 (m, 1H), 3.23-3.04 (m, 2H), 2.44-2.36 (m, 4H).

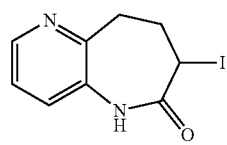 [SMILES: O=C1Nc2cccnc2CCC1I]

Step 4: 7-iodo-8,9-dihydro-5H-pyrido[3,2-b]azepin-6(7H)-one

To a solution of 5,7,8,9-tetrahydropyrido[3,2-b]azepin-6-one (2.25 g, 13.87 mmol) in dichloromethane (40 mL) was added tetramethylethylenediamine (6.24 mL, 41.62 mmol) and iodotrimethylsilane (5.92 mL, 41.62 mmol) under $N_2$ at 0° C. The mixture was stirred at 0° C. for 2 h, then iodine (5.28 g, 20.8 mmol) was added. The mixture was stirred for another 2 h at room temperature and then quenched by addition of saturated aqueous sodium sulfite (50 mL). The solution was extracted with dichloromethane (3×50 mL). The combined organic layers were dried over sodium sulfate and concentrated under reduced pressure to afford crude 7-iodo-5,7,8,9-tetrahydropyrido[3,2-b]azepin-6-one (3.50 g, 88%) as a yellow solid, used in the next step without further purification.

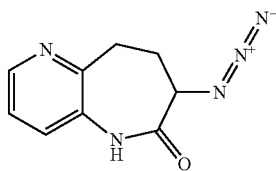 [SMILES: [N-]=[N+]=NC1CCc2ncccc2NC1=O]

Step 5: 7-azido-8,9-dihydro-5H-pyrido[3,2-b]azepin-6(7H)-one

To a solution of 7-iodo-5,7,8,9-tetrahydropyrido[3,2-b]azepin-6-one (3.50 g, 12.2 mmol) in N,N-dimethylformamide (100 mL) was added sodium azide (2.37 g, 36.5 mmol). The mixture was stirred at 25° C. for 1 h and poured into ice water (20 mL). The solution was extracted with ethyl acetate (4×20 mL). The combined organic layers were dried over sodium sulfate and concentrated under reduced pressure to afford crude 7-azido-5,7,8,9-tetrahydropyrido[3,2-b]azepin-6-one (2.20 g, 89%) as a yellow solid, used in the next step without further purification.

Step 6: (S)-7-amino-8,9-dihydro-5H-pyrido[3,2-b]azepin-6(7H)-one and (R)-7-amino-8,9-dihydro-5H-pyrido[3,2-b]azepin-6(7H)-one

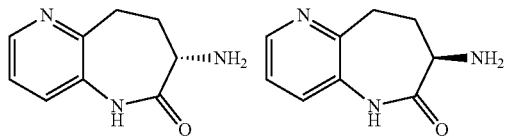

A mixture of 7-azido-5,7,8,9-tetrahydropyrido[3,2-b]azepin-6-one (2.20 g, 10.8 mmol) and palladium (10% on carbon, 114 mg) in ethanol (100 mL) was hydrogenated (15 psi) at 25° C. for 1 h and then filtered. The filtrate was concentrated under reduced pressure and the residue was purified by column chromatography (silica gel, 100-200 mesh, 0 to 20% methanol in ethyl acetate) to give 7-amino-5,7,8,9-tetrahydropyrido[3,2-b]azepin-6-one (1.70 g, 89%) as a brown solid. LCMS: $R_T$=0.763 min, m/z=178.2 $[M+H]^+$.

LCMS (0 to 30% acetonitrile in water+0.05% ammonium hydroxide over 3 minutes) retention time: 0.763 min, ESI+ found [M+H]=178.2.

Racemic 7-amino-5,7,8,9-tetrahydropyrido[3,2-b]azepin-6-one (950 mg, 5.36 mmol) was separated by chiral SFC to afford arbitrarily assigned:

(7S)-7-amino-5,7,8,9-tetrahydropyrido[3,2-b]azepin-6-one (Peak 1, retention time 2.832 min) (390 mg, 41%) as a yellow solid.

(7R)-7-amino-5,7,8,9-tetrahydropyrido[3,2-b]azepin-6-one (Peak 2 retention time: 3.628 min) (380 mg, 40%) as a yellow solid.

SFC conditions: Column: Chiralcel OJ-3 100×4.6 mm I.D., 3 um; Mobile phase: A: $CO_2$ B: ethanol (0.05% DEA); Gradient: from 5% to 40% of B in 4.5 min and hold 40%; for 2.5 min, then 5% of B for 1 min; Flow rate: 2.8 mL/min; Column temperature: 40° C.

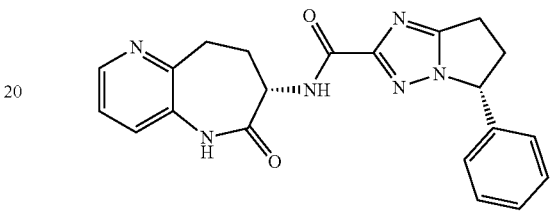

Step 7: (5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide A mixture of (7S)-7-amino-5,7,8,9-tetrahydropyrido[3,2-b]azepin-6-one (25 mg, 0.14 mmol), 1-(3-dimethylaminopropyl)-3-ethylcarbodiimidehydrochloride (41 mg, 0.21 mmol), (5R)-5-phenyl-6,7-dihydro-5H-pyrrolo[1,2-b][1,2,4]triazole-2-carboxylic acid (from Example #12, 32 mg, 0.14 mmol) and 1-hydroxybenzotriazole (6 mg, 0.04 mmol) in N,N-dimethylformamide (2 mL) was stirred at 25° C. for 3 h. The reaction mixture was concentrated under reduced pressure. The residue was purified by RP-HPLC (acetonitrile 15-45%/0.05% ammonia hydroxide in water) to afford (5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide (43 mg, 77%) as a white solid. $^1H$ NMR (400 MHz, $CDCl_3$) δ 8.43-8.35 (m, 1H), 8.17 (s, 1H), 7.95 (d, J=2.0 Hz, 1H), 7.40-7.29 (m, 4H), 7.23-7.17 (m, 1H), 7.13-7.06 (m, 2H), 5.50-5.40 (m, 1H), 4.82-4.73 (m, 1H), 3.27-3.08 (m, 3H), 3.06-2.90 (m, 3H), 2.72-2.61 (m, 1H), 2.22-2.09 (m, 1H). LCMS $R_T$=1.314 min, m/z=389.2 $[M+H]^+$.

LCMS (10 to 80% acetonitrile in water+0.05% ammonium hydroxide over 3 mins) retention time 1.314 min, ESI+ found [M+H]=389.2.

Example #14

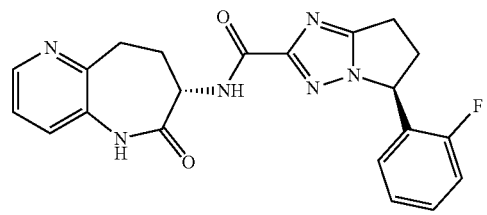 [SMILES: O=C(N[C@H]1CCc2ncccc2NC1=O)c1nc2n(n1)[C@H](c1ccccc1F)CC2]

(5S)-5-(2-fluorophenyl)-N-[(7S)-6-oxo-5,7,8,9-tetra-hydropyrido[3,2-b]azepin-7-yl]-6,7-dihydro-5H-pyrrolo[1,2-b][1,2,4]triazole-2-carboxamide Prepared in a similar fashion to Example #13. The crude was purified by RP-HPLC (acetonitrile 15-45%/0.05% ammonium hydroxide in water) to afford (5S)-5-(2-fluoro-phenyl)-N-[(7S)-6-oxo-5,7,8,9-tetrahydropyrido[3,2-b]aze-pin-7-yl]-6,7-dihydro-5H-pyrrolo[1,2-b][1,2,4]triazole-2-carboxamide (28.9 mg, 70%) as a white solid. $^1$H NMR (400 MHz, CD$_3$OD) δ 8.33 (d, J=4.8 Hz, 1H), 7.51 (dd, J=1.6, 8.0 Hz, 1H), 7.39-7.37 (m, 2H), 7.20-7.15 (m, 3H), 5.77 (dd, J=5.6, 8.8 Hz, 1H), 4.56 (dd, J=8.0, 11.8 Hz, 1H), 3.30-3.25 (m, 1H), 3.23-3.06 (m, 3H), 3.02-2.90 (m, 1H), 2.79-2.66 (m, 2H), 2.36-2.26 (m, 1H). LCMS R$_T$=1.384 min, m/z=407.2 [M+H]$^+$.

LCMS (0 to 60% acetonitrile in water+0.03% trifluoacetic acid over 3.0 mins) retention time 1.384 min, ESI+ found [M+H]=407.2.

Example #15

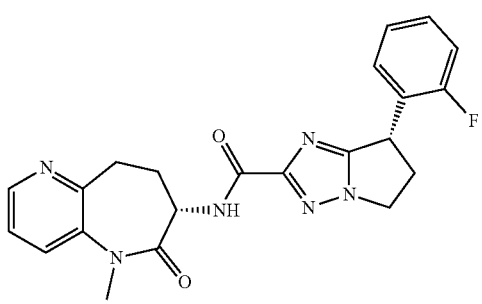 [SMILES: CN1C(=O)[C@@H](NC(=O)c2nc3n(n2)CC[C@H]3c2ccccc2F)CCc2ncccc21]

(7S)-7-(2-fluorophenyl)-N-[(7S)-5-methyl-6-oxo-8,9-dihydro-7H-pyrido[3,2-b]azepin-7-yl]-6,7-di-hydro-5H-pyrrolo[1,2-b][1,2,4]triazole-2-carboxam-ide

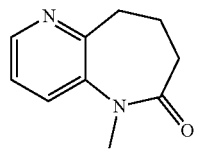

Step 1: 5-methyl-8,9-dihydro-5H-pyrido[3,2-b]aze-pin-6(7H)-one

To a stirring and cooled (−78° C.) solution of 5,7,8,9-tetrahydropyrido[3,2-b]azepin-6-one (1.60 g, 9.86 mmol) in tetrahydrofuran (50 mL) was added n-butyllithium (4.74 mL, 11.84 mmol) dropwise under N$_2$. After addition, the reaction mixture was stirred at 0° C. for 30 min and re-cooled to −78° C. Iodomethane (1.68 g, 11.84 mmol) was added via syringe and the mixture was stirred at 25° C. for 17 h. The mixture was quenched by addition of saturated ammonium chloride (100 mL) and extracted with ethyl acetate (3×100 mL). The combined organic layers were dried over sodium sulfate and concentrated under reduced pressure. The residue was purified by column chromatog-raphy (silica gel, 100-200 mesh, 0 to 100% ethyl acetate in petroleum ether) to give 5-methyl-8,9-dihydro-7H-pyrido[3,2-b]azepin-6-one (1.60 g, 92%) as a brown solid. $^1$H NMR (400 MHz, CDCl$_3$) δ 8.38-8.36 (m, 1H), 7.48-7.45 (m, 1H), 7.28-7.24 (m, 1H), 3.34 (s, 3H), 3.04-2.91 (m, 2H), 2.39-2.24 (m, 4H).

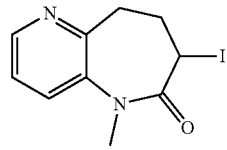

Step 2: 7-iodo-5-methyl-8,9-dihydro-5H-pyrido[3,2-b]azepin-6(7H)-one

To a solution of 5-methyl-8,9-dihydro-7H-pyrido[3,2-b]azepin-6-one (1.45 g, 8.23 mmol) in dichloromethane (40 mL) was added tetramethylethylenediamine (5.74 g, 49.37 mmol) at −15° C., then iodotrimethylsilane (9.88 g, 49.37 mmol) was added dropwise. The reaction mixture was stirred at −15° C. for 2 h, iodine (25.06 g, 98.74 mmol) was added. The mixture was stirred at −15° C. for another 2 h and quenched by the addition of saturated aqueous sodium sulfite (150 mL). The resulting mixture was extracted with dichloromethane (2×50 mL). The combined organic layers were dried over sodium sulfate and concentrated reduced pressure to afford crude 7-iodo-5-methyl-8,9-dihydro-7H-pyrido[3,2-b]azepin-6-one (2.40 g, 97%) as a brown solid, used as is in the next step.

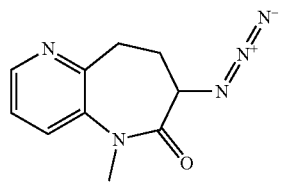

Step 3: 7-azido-5-methyl-8,9-dihydro-5H-pyrido[3,2-b]azepin-6(7H)-one

To a solution of 7-iodo-5-methyl-8,9-dihydro-7H-pyrido[3,2-b]azepin-6-one (2.40 g, 7.94 mmol) in N,N-dimethyl-formamide (40 mL) was added sodium azide (1.55 g, 23.83 mmol). The mixture was stirred at 25° C. for 1 h and poured into ice water (200 mL). The resulting solution was extracted with dichloromethane (4×200 mL). The combined organic layers were dried over sodium sulfate and concentrated under reduced pressure to afford crude 7-azido-5-methyl-8,9-dihydro-7H-pyrido[3,2-b]azepin-6-one (1.72 g, 99%) as a brown oil, used as is in the next step.

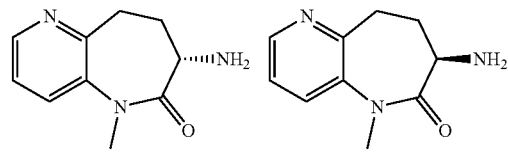

Step 4: (S)-7-amino-5-methyl-8,9-dihydro-5H-pyrido[3,2-b]azepin-6(7H)-one and (S)-7-amino-5-methyl-8,9-dihydro-5H-pyrido[3,2-b]azepin-6(7H)-one A mixture of 7-azido-5-methyl-8,9-dihydro-7H-pyrido[3,2-b]azepin-6-one (1.72 g, 7.92 mmol) and palladium (10% in carbon, 339 mg) in ethanol (200 mL) was hydrogenated (15 psi) at 25° C. for 1 h and then filtered. The filtrate was concentrated reduced pressure. The residue was purified by column chromatography (silica gel, 100-200 mesh, 0 to 20% methanol in ethyl acetate) to give 7-amino-5-methyl-8,9-dihydro-7H-pyrido[3,2-b]azepin-6-one (1.3 g, 86%) as a brown oil. $^1$H NMR (400 MHz, CDCl$_3$) δ 8.39-8.37 (m, 1H), 7.48-7.44 (m, 1H), 7.29-7.22 (m, 1H), 3.43-3.36 (m, 4H), 3.07-2.94 (m, 1H), 2.92-2.85 (m, 1H), 2.60-2.55 (m, 1H), 2.04-1.92 (m, 1H).

Racemic 7-amino-5-methyl-8,9-dihydro-7H-pyrido[3,2-b]azepin-6-one (900 mg, 4.71 mmol) was separated by chiral SFC to afford arbitrarily assigned:

(7S)-7-amino-5-methyl-8,9-dihydro-7H-pyrido[3,2-b]azepin-6-one (Peak 1, retention time=2.328 min) (400 mg, 44%) as light blue oil.

(7R)-7-amino-5-methyl-8,9-dihydro-7H-pyrido[3,2-b]azepin-6-one (Peak 2, retention time=2.767 min) (450 mg, 50%) as light blue oil.

SFC conditions: Column: AS (250 mm*30 mm, 5 um); Mobile phase: A: CO$_2$ B: 0.1% NH$_3$H$_2$O/EtOH; Gradient: from 20% to 20% of B; Flow rate: 60 mL/min.

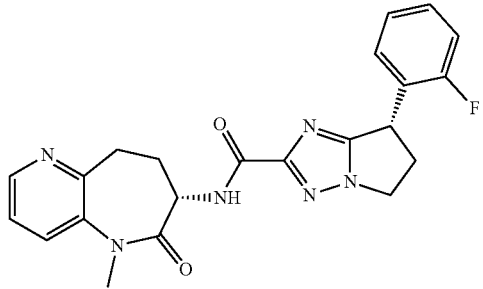 [SMILES: CN1C(=O)[C@@H](NC(=O)c2nc3n(n2)CC[C@H]3c2ccccc2F)CCc2ncccc21]

Step 5: (7S)-7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide A mixture of 7-(2-fluorophenyl)-6,7-dihydro-5H-pyrrolo[1,2-b][1,2,4]triazole-2-carboxylic acid (71 mg, 0.29 mmol), 1-hydroxybenzotriazole (42 mg, 0.31 mmol), 1-(3-dimethylaminopropyl)-3-ethylcarbodiimidehydrochloride (60 mg, 0.31 mmol) and (7S)-7-amino-5-methyl-8,9-dihydro-7H-pyrido[3,2-b]azepin-6-one (50 mg, 0.26 mmol) in N,N-dimethylformamide (3 mL) was stirred at 30° C. for 18 h. The mixture was concentrated reduced pressure. The residue was purified by RP-HPLC (acetonitrile 30-60%/0.05% ammonium hydroxide in water) to afford 7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (60 mg, 55%) as a white solid. LCMS R$_T$=1.451 min, m/z=421.2 [M+H]$^-$.

LCMS (10 to 80% acetonitrile in water+0.05% ammonium bicarbonate over 3 mins) retention time 1.451 min, ESI+ found [M+H]=421.2.

Racemic 7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (60 mg, 0.14 mmol) was separated by chiral SFC to afford arbitrarily assigned:

(7S)-7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (Peak 1, retention time=4.467 min) (16.5 mg, 27%) as a white solid. $^1$H NMR (400 MHz, CD$_3$OD) δ 8.39 (d, J=4.8 Hz, 1H), 7.85 (d, J=8.0 Hz, 1H), 7.48 (dd, J=4.8, 8.0 Hz, 1H), 7.39-7.25 (m, 2H), 7.22-7.08 (m, 2H), 4.77-4.69 (m, 1H), 4.55-4.49 (m, 1H), 4.45-4.35 (m, 1H), 4.34-4.24 (m, 1H), 3.41 (s, 3H), 3.20-3.09 (m, 1H), 2.95-2.88 (m, 1H), 2.78-2.57 (m, 2H), 2.33-2.24 (m, 1H). LCMS R$_T$=1.473 min, m/z=421.2 [M+H]$^+$.

LCMS (10 to 80% acetonitrile in water+0.05% ammonium bicarbonate over 3 mins) retention time 1.473 min, ESI+ found [M+H]=421.2.

SFC conditions: Column: AD (250 mm×30 mm, 5 um); Mobile phase: A: CO$_2$ B: IPA (0.1% NH$_3$H$_2$O); Gradient: from 40% to 40%; Flow rate: 60 mL/min.

Example #16

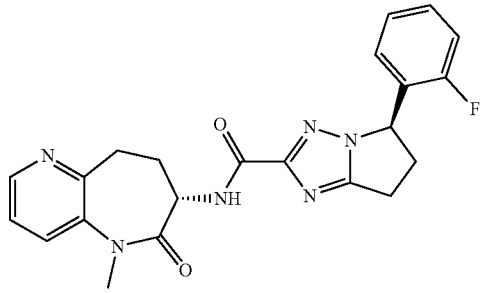 [SMILES: CN1C(=O)[C@@H](NC(=O)c2nc3n(n2)[C@@H](c2ccccc2F)CC3)CCc2ncccc21]

(5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide Prepared in a similar fashion to Example #15. The crude was purified by purified by RP-HPLC (acetonitrile 15-45%/0.05% ammonia hydroxide in water) to afford (5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (18 mg, 32%) as a white solid. $^1$H NMR (400 MHz, CD$_3$OD) δ 8.39 (d, J=5.2 Hz, 1H), 7.83 (d, J=8.0 Hz, 1H), 7.48-7.44 (m, 1H), 7.43-7.36 (m, 1H), 7.20-7.15 (m, 3H), 5.79-5.74 (m, 1H), 4.51 (dd, J=8.0, 11.6 Hz, 1H), 3.41 (s, 3H), 3.29-3.24 (m, 1H), 3.20-3.03 (m, 3H), 2.95-2.87 (m, 1H), 2.76-2.67 (m, 1H), 2.66-2.57 (m, 1H), 2.33-2.22 (m, 1H).

LCMS R$_T$=1.454 min, m/z=421.2 [M+H]$^+$.

LCMS (10 to 80% acetonitrile in water+0.05% ammonium hydroxide over 3 mins) retention time 1.454 min, ESI+ found [M+H]=421.2.

Example #17

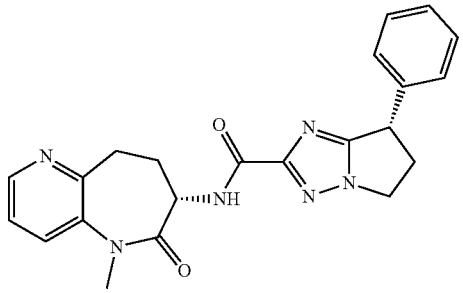 [SMILES: CN1C(=O)[C@@H](NC(=O)c2nc3n(n2)CC[C@H]3c2ccccc2)CCc2ncccc21]

(7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide

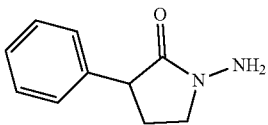 [SMILES: NN1CCC(c2ccccc2)C1=O]

Step 1: 1-amino-3-phenylpyrrolidin-2-one

To a solution of tert-butyl N-(2-oxo-3-phenyl-pyrrolidin-1-yl)carbamate (1.4 g, 5.1 mmol) in ethyl acetate (20 mL) was added HCl (4N in ethyl acetate, 12.0 mL, 48.0 mmol). The mixture was stirred at 20° C. for 3 h and concentrated under reduced pressure. The residue was slowly quenched by addition of saturated sodium bicarbonate (30 mL). The resulting solution was extracted with ethyl acetate (3×50 mL). The combined organic layers were dried over sodium sulfate and concentrated to give crude 1-amino-3-phenyl-pyrrolidin-2-one (590 mg, 66%) as a white solid, used as is in the next step.

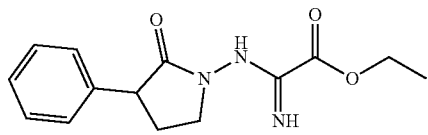 [SMILES: CCOC(=O)C(=N)NN1CCC(c2ccccc2)C1=O]

Step 2: ethyl 2-imino-2-((2-oxo-3-phenylpyrrolidin-1-yl)amino)acetate

To a solution of 1-amino-3-phenyl-pyrrolidin-2-one (590 mg, 3.35 mmol) in ethanol (10 mL) was added ethyl 2-ethoxy-2-imino-acetate (1458 mg, 10.04 mmol). The mixture was stirred at 40° C. for 12 h and concentrated under reduced pressure to obtain crude ethyl (2Z)-2-amino-2-(2-oxo-3-phenyl-pyrrolidin-1-yl)imino-acetate (1370 mg, 100%), used as is in the next step.

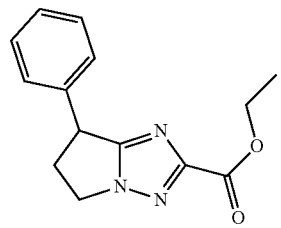 [SMILES: CCOC(=O)c1nc2n(n1)CCC2c1ccccc1]

Step 3: Ethyl 7-phenyl-6,7-dihydro-5H-pyrrolo[1,2-b][1,2,4]triazole-2-carboxylate A solution of ethyl (2Z)-2-amino-2-(2-oxo-3-phenyl-pyrrolidin-1-yl)imino-acetate (1370 mg, 4.98 mmol) in phosphorus oxychloride (5 mL) as stirred at 120° C. for 1 h. After cooled, the mixture was slowly quenched by addition of saturated sodium bicarbonate (20 mL) and extracted with dichloromethane (3×20 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford ethyl 7-phenyl-6,7-dihydro-5H-pyrrolo[1,2-b][1,2,4]triazole-2-carboxylate (390 mg, 31%) as a light yellow solid. $^1$H NMR (400 MHz, CDCl$_3$) δ7.40-7.14 (m, 5H), 4.45 (q, J=8.0 Hz, 4H), 4.40-4.36 (m, 1H), 4.26-4.23 (m, 1H), 3.29-3.22 (m, 1H), 2.78-2.70 (m, 1H), 1.40 (t, J=7.2 Hz, 3H). LCMS R$_T$=1.95 min, m/z=258.1 [M+H]$^+$.

LCMS (0 to 60% acetonitrile in water+0.05% ammonium hydroxide over 3 mins) retention time 1.95 min, ESI+ found [M+H]=258.1.

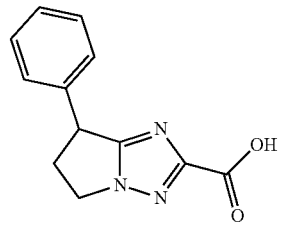 [SMILES: O=C(O)c1nc2n(n1)CCC2c1ccccc1]

Step 4: 7-phenyl-6,7-dihydro-5H-pyrrolo[1,2-b][1,2,4]triazole-2-carboxylic acid

A mixture of ethyl (7S)-7-phenyl-6,7-dihydro-5H-pyrrolo[1,2-b][1,2,4]triazole-2-carboxylate (340 mg, 1.32 mmol) and lithium hydroxide hydrate (555 mg, 13.22 mmol) in tetrahydrofuran (5 mL) and water (5 mL) was stirred at 20° C. for 12 h. The organic solvent was evaporated under reduced pressure and the aqueous residue was adjusted to pH=2-3 by addition of 20% HCl. The mixture was extracted with dichloromethane (5×30 mL). The combined organic layers were dried over sodium sulfate and concentrated under reduced pressure to afford the crude 7-phenyl-6,7-dihydro-5H-pyrrolo[1,2-b][1,2,4]triazole-2-carboxylic acid (260 mg, 85%) as a yellow solid, used as is in the next step.

Step 5: (7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide A mixture of (7S)-7-amino-5-methyl-8,9-dihydro-7H-pyrido[3,2-b]azepin-6-one (30 mg, 0.16 mmol), 1-hydroxybenzotriazole (7 mg, 0.05 mmol), 1-(3-dimethylaminopropyl)-3-ethylcarbodiimidehydrochloride (45 mg, 0.24 mmol) and 7-phenyl-6,7-dihydro-5H-pyrrolo[1,2-b][1,2,4]triazole-2-carboxylic acid (36 mg, 0.16 mmol) in N,N-dimethylformamide (3 mL) was stirred at 25° C. for 15 h. The mixture was concentrated under reduced pressure. The residue was purified by RP-HPLC (acetonitrile 15-45%/0.05% ammonia hydroxide in water) to afford a white racemic product, which was further separated by chiral SFC to afford arbitrarily assigned:

(7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (Peak 1, retention time=4.375 min) (12.6 mg, 19%) as a white solid. $^1$H NMR (400 MHz, CD$_3$OD) δ 8.39 (d, J=4.8 Hz, 1H), 7.84 (d, J=8.0 Hz, 1H), 7.47 (dd, J=4.0, 4.0 Hz, 1H), 7.39-7.32 (m, 2H), 7.31-7.25 (m, 3H), 4.56-4.48 (m, 2H), 4.43-4.36 (m, 1H), 4.30-4.22 (m, 1H), 3.40 (s, 3H), 3.29-3.22 (m, 1H), 3.18-3.08 (m, 1H), 2.95-2.87 (m, 1H), 2.67-2.58 (m, 2H), 2.33-2.21 (m, 1H). LCMS R$_T$=0.698 min, m/z=403.1 [M+H]$^+$.

LCMS (5 to 95% acetonitrile in water+0.03% trifluoroacetic acid over 1.5 mins) retention time 0.698 min, ESI+ found [M+H]=403.1.

SFC conditions: Column: Chiralpak AD-3 100×4.6 mm I.D., 3 um Mobile phase: A: CO$_2$ B: ethanol (0.05% DEA) Gradient: from 5% to 40% of B in 4.5 min and hold 40% for 2.5 min, then 5% of B for 1 min, Flow rate: 2.8 mL/min, Column temperature: 40° C.

Example #18

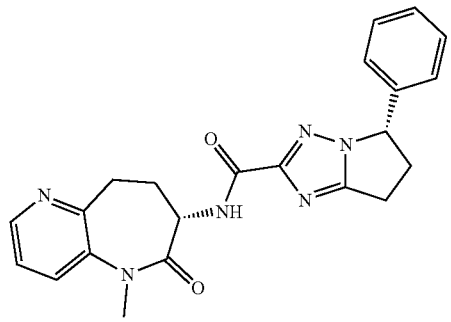 [SMILES: CN1C(=O)[C@@H](NC(=O)c2nc3n(n2)[C@H](c2ccccc2)CC3)CCc2ncccc21]

(5S)-5-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide Prepared in a similar fashion to Example #15. The residue was purified by RP-HPLC (acetonitrile 15-45%/0.05% ammonium hydroxide in water) to afford (5S)-5-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide (22 mg, 66%) as a white solid. $^1$H NMR (400 MHz, CD$_3$OD) δ 8.37 (d, J=4.0 Hz, 1H), 7.82 (d, J=7.6 Hz, 1H), 7.47-7.45 (m, 1H), 7.40-7.31 (m, 3H), 7.21-7.19 (m, 2H), 5.55-5.50 (m, 1H), 4.52-4.47 (m, 1H), 3.40 (s, 3H), 3.26-3.20 (m, 1H), 3.17-3.09 (m, 2H), 3.08-3.00 (m, 1H), 2.91-2.90 (m, 1H), 2.70-2.56 (m, 2H), 2.30-2.21 (m, 1H). LCMS R$_T$=1.417 min, m/z=403.1 [M+H]$^+$.

LCMS (10 to 80% acetonitrile in water+0.05% ammonium hydroxide over 3 mins) retention time 1.417 min, ESI+ found [M+H]=403.1.

Example #19

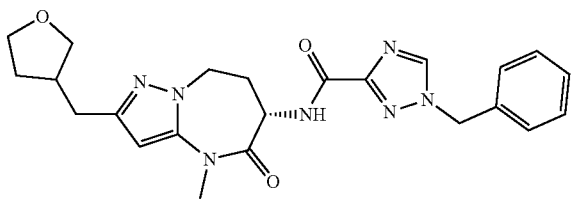 [SMILES: CN1C(=O)[C@@H](NC(=O)c2ncn(Cc3ccccc3)n2)CCn2nc(CC3CCOC3)cc21]

1-benzyl-N-[(6S)-4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide

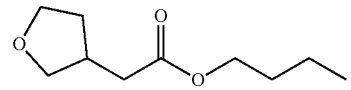

Step 1: butyl 2-(tetrahydrofuran-3-yl)acetate

To a solution of 1-iodobutane (12.4 g, 67.9 mmol) in acetonitrile (100 mL) was added 1,8-diazabicyclo[5.4.0]undec-7-ene (9.36 g, 61.1 mmol), followed by (tetrahydrofuran-3-yl)-acetic acid (8.0 g, 61.1 mmol) at 0° C. The resulting mixture was stirred at 25° C. for 12 h and poured into water (100 mL). The mixture was extracted with ethyl acetate (2×100 mL). The combined organic layers were washed with brine (50 mL), dried over anhydrous sodium sulfate and concentrated under reduced pressure to give crude butyl 2-tetrahydrofuran-3-ylacetate (11.0 g, 96%) as a yellow oil, used as is in the next step.

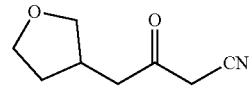 [SMILES: N#CCC(=O)CC1CCOC1]

Step 2: 3-oxo-4-(tetrahydrofuran-3-yl)butanenitrile

To a solution of acetonitrile (2.67 g, 65.0 mmol) in tetrahydrofuran (20 mL) was added n-butyllithium (26.0 mL, 65.0 mmol) at −78° C. The resulting mixture was stirred at the same temperature for 30 min, and butyl 2-tetrahydrofuran-3-ylacetate (11.0 g, 59.1 mmol) was added dropwise. After addition, the reaction mixture was stirred for another 2 h at 25° C. and then slowly quenched by addition of saturated aqueous ammonium chloride (20 mL). The mixture was extracted with ethyl acetate (2×100 mL). The combined organic layers were washed with brine (100 mL), dried over anhydrous sodium sulfate and concentrated under reduced pressure to give crude 3-oxo-4-tetrahydrofuran-3-yl-butanenitrile (7.8 g, 86%) as a yellow oil, used as is in the next step.

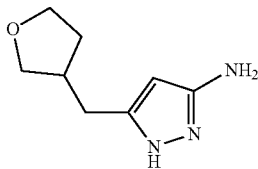 [SMILES: Nc1cc(CC2CCOC2)[nH]n1]

Step 3: 5-((tetrahydrofuran-3-yl)methyl)-1H-pyrazol-3-amine

A mixture of 3-oxo-4-tetrahydrofuran-3-yl-butanenitrile (7.8 g, 50.9 mmol) and hydrazine (10 mL) in 2-propanol (20 mL) was heated at 80° C. for 12 h and concentrated under reduce pressure. The residue was purified by column chromatography (silica gel, 100-200 mesh, 0 to 10% methanol in dichloromethane) to give 5-(tetrahydrofuran-3-ylmethyl)-1H-pyrazol-3-amine (2.8 g, 33%) as a yellow solid. LC-MS $R_T$=0.875 min, m/z=168.2 [M+H]$^+$.

LCMS (0 to 60% acetonitrile in water+0.03% ammonium bicarbonate over 3.0 mins) retention time 0.875 min, ESI+ found [M+H]=168.2.

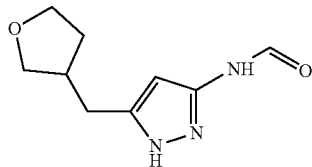 [SMILES: O=CNc1cc(CC2CCOC2)[nH]n1]

Step 4: N-(5-((tetrahydrofuran-3-yl)methyl)-1H-pyrazol-3-yl)formamide

A solution of 5-(tetrahydrofuran-3-ylmethyl)-1H-pyrazol-3-amine (2.8 g, 16.7 mmol) in formic acid (10 mL) was heated at 110° C. for 12 h and then concentrated removed under reduced pressure. The residue was purified by column chromatography (silica gel, 100-200 mesh, 0 to 5% dichloromethane in methanol) to give N-[5-(tetrahydrofuran-3-ylmethyl)-1H-pyrazol-3-yl]formamide (2.5 g, 77%) as a yellow solid. LC-MS $R_T$=1.083 min, m/z=196.1 [M+H]$^+$.

LCMS (0 to 60% acetonitrile in water+0.03% ammonium bicarbonate over 3.0 mins) retention time 1.083 min, ESI+ found [M+H]=196.1.

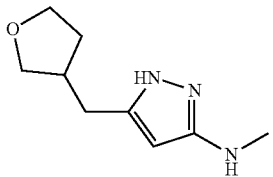

Step 5: N-methyl-5-((tetrahydrofuran-3-yl)methyl)-1H-pyrazol-3-amine

To a solution of N-[5-(tetrahydrofuran-3-ylmethyl)-1H-pyrazol-3-yl]formamide (2.0 g, 20.0 mmol) in tetrahydrofuran (40 mL) was added borane-dimethylsulfide complex (10 N, 4.0 mL, 40.0 mmol) at 0° C. The reaction mixture was stirred at 25° C. for 3 h and then slowly quenched by addition of methanol (20 mL) and hydrochloride acid (1N, 10 mL). The resulting mixture was stirred fir 30 min and then concentrated to dryness under reduced pressure. The residue was purified by column chromatography (silica gel, 100-200 mesh, 0 to 5% dichloromethane in methanol) to give N-methyl-5-(tetrahydrofuran-3-ylmethyl)-1H-pyrazol-3-amine (1.2 g, 65%) as a colorless oil. LC-MS $R_T$=1.229 min, m/z=182.2 [M+H]$^+$.

LCMS (0 to 60% acetonitrile in water+0.03% ammonium bicarbonate over 3.0 mins) retention time 1.229 min, ESI+ found [M+H]=182.2.

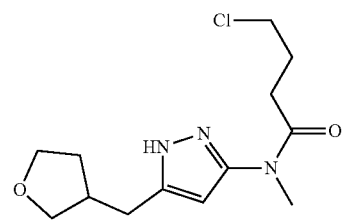 [SMILES: CN(C(=O)CCCCl)c1cc(CC2CCOC2)[nH]n1]

Step 6: 4-chloro-N-methyl-N-(5-((tetrahydrofuran-3-yl)methyl)-1H-pyrazol-3-yl)butanamide A mixture of 4-chlorobutanoyl chloride (18.7 g, 132.2 mmol) and N-methyl-5-(tetrahydrofuran-3-ylmethyl)-1H-pyrazol-3-amine (1.2 g, 6.6 mmol) was heated at 60° C. for 30 min. After cooled to room temperature, the mixture was slowly added methanol (10 mL) and stirred for another 30 min. The mixture was concentrated to dryness under reduce pressure. The residue was purified by column chromatography (silica gel, 100-200 mesh, 0 to 5% dichloromethane in methanol) to give 4-chloro-N-methyl-N-[5-(tetrahydrofuran-3-ylmethyl)-1H-pyrazol-3-yl]butanamide (1.3 g, 67%) as yellow oil.

LCMS $R_T$=0.797 min, m/z=285.8 [M+H]$^+$.

LCMS (5 to 95% acetonitrile in water+0.03% trifluoroacetic acid over 1.5 mins) retention time 0.797 min, ESI+ found [M+H]=285.8.

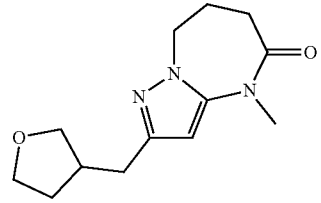 [SMILES: CN1C(=O)CCCn2nc(CC3CCOC3)cc21]

Step 7: 4-methyl-2-((tetrahydrofuran-3-yl)methyl)-7,8-dihydro-4H-pyrazolo[1,5-a][1,3]diazepin-5(6H)-one A mixture of 4-chloro-N-methyl-N-[5-(tetrahydrofuran-3-ylmethyl)-1H-pyrazol-3-yl]butanamide (1.3 g, 4.5 mmol) and cesium carbonate (3.0 g, 9.1 mmol) in N,N-dimethylformamide (10 mL) was stirred at 25° C. for 12 h and then filtered. The filtrate was concentrated under reduce pressure and the residue was purified by column chromatography (silica gel, 100-200 mesh, 0 to 5% dichloromethane in methanol) to give 4-methyl-2-((tetrahydrofuran-3-ylmethyl)-

7,8-dihydro-6H-pyrazolo[1,5-a][1,3]diazepin-5-one (850 mg, 75%) as yellow oil. LC-MS R$_T$=1.050 min, m/z=250.2 [M+H]$^+$.

LCMS (10 to 80% acetonitrile in water+0.03% ammonium bicarbonate over 3.0 mins) retention time 1.050 min, ESI+ found [M+H]=250.2.

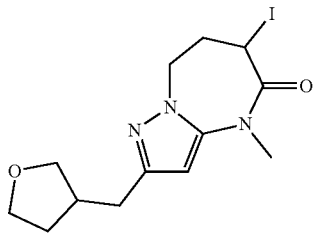

Step 8: 6-iodo-4-methyl-2-((tetrahydrofuran-3-yl)methyl)-7,8-dihydro-4H-pyrazolo[1,5-a][1,3]diazepin-5(6H)-one To a solution of 4-methyl-2-(tetrahydrofuran-3-ylmethyl)-7,8-dihydro-6H-pyrazolo[1,5-a][1,3]diazepin-5-one (420 mg, 1.68 mmol) in dichloromethane (15 mL) was added N$^1$,N$^1$,N$^2$,N$^2$-tetramethylethane-1,2-diamine (1.96 g, 16.8 mmol) at −15° C., followed by iodotrimethylsilane (3.37 g, 16.8 mmol). After addition, the mixture was stirred at −15° C. for another 1.5 h, and iodine (1.28 g, 5.05 mmol) was added. The reaction mixture was stirred for another 3 h and quenched by the addition of saturated aqueous sodium sulfite (10 mL). The resulting mixture was extracted with dichloromethane (3×20 mL). The combined organic layers were dried over sodium sulfate and concentrated under reduced pressure. The residue was purified by column chromatography (silica gel, 100-200 mesh, 0 to 5% dichloromethane in methanol) to give 6-iodo-4-methyl-2-(tetrahydrofuran-3-ylmethyl)-7,8-dihydro-6H-pyrazolo[1,5-a][1,3]diazepin-5-one (220 mg, 35%) as light yellow oil.

LCMS R$_T$=1.399 min, m/z=375.9 [M+H]$^+$.

LCMS (10 to 80% acetonitrile in water+0.03% ammonium bicarbonate over 3.0 mins) retention time 1.399 min, ESI+ found [M+H]=375.9.

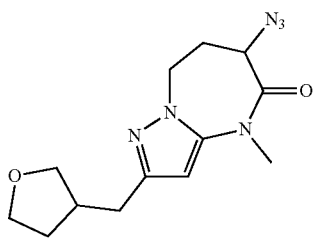 [SMILES: CN1C(=O)C(I)CCn2nc(CC3CCOC3)cc21]

Step 9: 6-azido-4-methyl-2-((tetrahydrofuran-3-yl)methyl)-7,8-dihydro-4H-pyrazolo[1,5-a][1,3]diazepin-5(6H)-one To a solution of 6-iodo-4-methyl-2-(tetrahydrofuran-3-ylmethyl)-7,8-dihydro-6H-pyrazolo[1,5-a][1,3]diazepin-5-one (220 mg, 0.59 mmol) in N,N-dimethylformamide (2 mL) was added sodium azide (720 mg, 11.0 mmol). The reaction mixture was stirred at 25° C. for 12 h and then extracted with ethyl acetate (2×30 mL). The combined organic layers were washed with brine (20 mL), dried over sodium sulfate and concentrated under reduced pressure to afford crude 6-azido-4-methyl-2-(tetrahydrofuran-3-ylmethyl)-7,8-dihydro-6H-pyrazolo[1,5-a][1,3]diazepin-5-one (160 mg, 94%) as a yellow oil, used as is in the next step. LC-MS R$_T$=1.348 min, m/z=291.1 [M+H]$^+$.

LCMS (10 to 80% acetonitrile in water+0.03% ammonium bicarbonate over 3.0 mins) retention time 1.348 min, ESI+ found [M+H]=291.1.

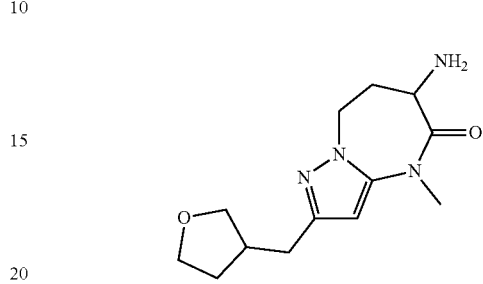

Step 10: 6-amino-4-methyl-2-((tetrahydrofuran-3-yl)methyl)-7,8-dihydro-4H-pyrazolo[1,5-a][1,3]diazepin-5(6H)-one A solution of 6-azido-4-methyl-2-(tetrahydrofuran-3-ylmethyl)-7,8-dihydro-6H-pyrazolo[1,5-a][1,3]diazepin-5-one (160 mg, 0.55 mmol) in tetrahydrofuran (2.5 mL) and water (0.5 mL) was added 80% polymer-bound triphenylphosphine (867 mg). The reaction mixture was stirred at 25° C. for 12 h and filtered. The filtrate was concentrated reduced pressure and the residue was purified by column chromatography (silica gel, 100-200 mesh, 0 to 5% dichloromethane in methanol) to give 6-amino-4-methyl-2-(tetrahydrofuran-3-ylmethyl)-7,8-dihydro-6H-pyrazolo[1,5-a][1,3]diazepin-5-one (100 mg, 69%) as light yellow oil. LC-MS R$_T$=1.283 min, m/z=265.2 [M+H]$^+$.

LCMS (0 to 60% acetonitrile in water+0.03% ammonium bicarbonate over 3.0 mins) retention time 1.283 min, ESI+ found [M+H]=265.2.

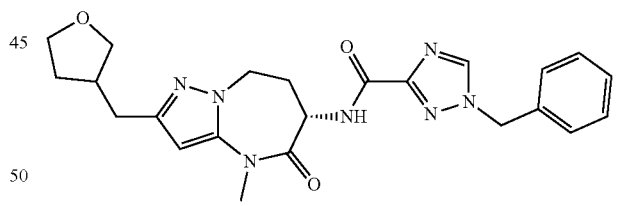

Step 11: 1-benzyl-N-((6S)-4-methyl-5-oxo-2-((tetrahydrofuran-3-yl)methyl)-5,6,7,8-tetrahydro-4H-pyrazolo[1,5-a][1,3]diazepin-6-yl)-1H-1,2,4-triazole-3-carboxamide A mixture of 1-(3-dimethylaminopropyl)-3-ethylcarbodiimidehydrochloride (35 mg, 0.18 mmol), 6-amino-4-methyl-2-(tetrahydrofuran-3-ylmethyl)-7,8-dihydro-6H-pyrazolo[1,5-a][1,3]diazepin-5-one (40 mg, 0.15 mmol), 1-hydroxybenzotriazole (25 mg, 0.18 mmol) and 1-benzyl-1,2,4-triazole-3-carboxylic acid (34 mg, 0.17 mmol) in N,N-dimethylformamide (3 mL) was stirred at 25° C. for 12 h. The reaction mixture was concentrated under reduced pressure. The residue was purified by RP-HPLC (methanol 40%-70%/0.05% ammonia hydroxide in water) to afford 1-benzyl-N-[4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide (30 mg, 43%) as a white solid.

Racemic benzyl-N-[4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide (30 mg, 0.07 mmol) was separated by chiral SFC to afford arbitrarily assigned:

1-benzyl-N-[(6S)-4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide (peak 1 & 2, retention time=1.698 & 1.732 min) (10 mg, 33%) as a white solid. $^1$H NMR (400 MHz, CD$_3$OD) δ 8.56 (s, 1H), 7.38-7.32 (m, 5H), 6.17 (s, 1H), 5.47 (s, 2H), 4.53-4.49 (m, 1H), 4.37-4.30 (m, 1H), 4.26-4.18 (m, 1H), 3.91-3.84 (m, 2H), 3.79-3.72 (m, 1H), 3.50-3.46 (m, 1H), 3.33 (s, 3H), 2.87-2.81 (m, 1H), 2.71-2.66 (m, 2H), 2.63-2.56 (m, 1H), 2.30-2.21 (m, 1H), 2.12-2.05 (m, 1H), 1.70-1.66 (m, 1H). LC-MS R$_T$=1.486 min, m/z=450.2 [M+H]$^+$.

LCMS (10 to 80% acetonitrile in water+0.05% ammonium hydroxide over 3 mins) retention time 1.486 min, ESI+ found [M+H]=450.2.

Example #20

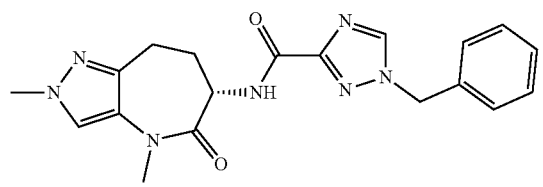 [SMILES: CN1C(=O)[C@@H](NC(=O)c2ncn(Cc3ccccc3)n2)CCc2nn(C)cc21]

1-benzyl-N-[(6S)-2,4-dimethyl-5-oxo-7,8-dihydro-6H-pyrazolo[4,3-b]azepin-6-yl]-1,2,4-triazole-3-carboxamide

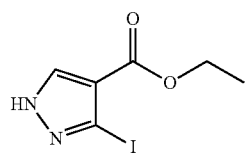

Step 1: ethyl 3-amino-1H-pyrazole-4-carboxylate

To a solution of ethyl 3-amino-1H-pyrazole-4-carboxylate (30.0 g, 193.4 mmol) in 50% sulfuric acid (300 mL) was added a solution of sodium nitrate (24.0 g, 348.1 mmol) in water (45 mL) at −10° C. The mixture was stirred for 1 h, and then a solution of potassium iodide (102.7 g, 618.8 mmol) in water (50 mL) was added. The reaction was stirred for 6 h at −10° C. and poured into water (200 mL). The resulting mixture was extracted with dichloromethane (3×100 mL). The combined organic layers were washed with saturated aqueous sodium bicarbonate (100 mL), saturated aqueous sodium thiosulphate (100 mL), dried over anhydrous sodium sulfate and concentrated under reduced pressure. The residue was purified by column chromatography (silica gel, 100-200 mesh, 0 to 20% ethyl acetate in petroleum ether) to give ethyl 3-iodo-1H-pyrazole-4-carboxylate (19.0 g, 37%) as a white solid, used as is in the next step.

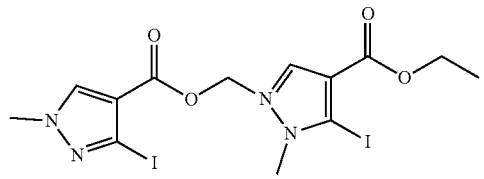

Step 2: ethyl 3-iodo-1-methyl-1H-pyrazole-4-carboxylate and ethyl 5-iodo-1-methyl-1H-pyrazole-4-carboxylate A mixture of ethyl 3-iodo-1H-pyrazole-4-carboxylate (17.0 g, 63.9 mmol), cesium carbonate (41.6 g, 127.8 mmol) and methyl iodide (6.0 mL, 95.9 mmol) in N,N-dimethylformamide (200 mL) was heated at 60° C. for 15 h and filtered. The filtrate was concentrated under reduced pressure. The residue was purified by column chromatography (silica gel, 100-200 mesh, 0 to 20% ethyl acetate in petroleum ether) to give ethyl 3-iodo-1-methyl-pyrazole-4-carboxylate (7.5 g, 42%) as a white solid and ethyl 5-iodo-1-methyl-pyrazole-4-carboxylate (7.5 g, 42%) as a white solid, used as is in the next step.

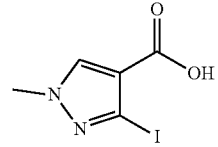

Step 3: 3-iodo-1-methyl-1H-pyrazole-4-carboxylic acid

A mixture of ethyl 3-iodo-1-methyl-pyrazole-4-carboxylate (5.0 g, 17.8 mmol) and lithium hydroxide (4.3 g, 178 mmol) in tetrahydrofuran (30 mL) and water (30 mL) was stirred at 25° C. for 15 h and concentrated under reduced pressure. The residue was adjusted to pH=5 by additional of hydrochloric acid (2 N). The formed solid was collected by filtration, washed with water (20 mL) and dried under reduced pressure to afford crude 3-iodo-1-methyl-pyrazole-4-carboxylic acid (3.0 g, 67%) as a white solid, used as is in the next step.

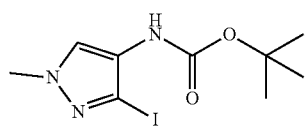

Step 4: tert-butyl (3-iodo-1-methyl-1H-pyrazol-4-yl)carbamate

To a stirred solution of 3-iodo-1-methyl-pyrazole-4-carboxylic acid (3.0 g, 11.9 mmol) in t-butanol (100 mL) was added triethylamine (1.8 g, 17.9 mmol), diphenylphosphoryl azide (3.6 g, 13.1 mmol). After addition, the mixture was stirred at 100° C. for 15 h. The reaction mixture was cooled and then diluted with ice water (200 mL). The resulting solution was extracted with dichloromethane (2×200 mL). The combined organic layers were dried over anhydrous sodium sulfate and concentrated under reduced pressure. The residue was purified by column chromatography (silica gel, 100-200 mesh, 0 to 30% ethyl acetate in petroleum ether) to give tert-butyl N-(3-iodo-1-methyl-pyrazol-4-yl) carbamate (1.8 g, 47%) as a white solid. $^1$H NMR (400 MHz, DMSO-d$_6$) δ 8.30 (s, 1H), 7.63 (br s, 1H), 3.79 (s, 3H), 1.43 (s, 9H).

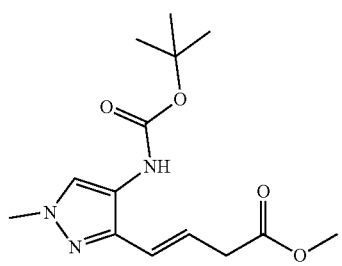

Step 5: methyl 4-(4-((tert-butoxycarbonyl)amino)-1-methyl-1H-pyrazol-3-yl)but-3-enoate A mixture of tert-butyl N-(5-iodo-1-methyl-pyrazol-4-yl) carbamate (1.50 g, 4.64 mmol), methyl 3-butenoate (1.39 g, 13.9 mmol), sodium bicarbonate (1.17 g, 13.9 mmol) and dichloropalladium; dicyclohexyl-[2-(2,4,6-triisopropyl-3-phenyl-phenyl) phenyl]phosphane (298 mg, 0.2 mmol) in N,N-dimethylformamide (30 mL) was heated at 120° C. for 24 h. After cooled, the mixture was poured into water (20 mL) and extracted with ethyl acetate (3×30 mL). The combined organic layers were dried over anhydrous sodium sulfate and concentrated under reduced pressure. The residue was purified by column chromatography (silica gel, 100-200 mesh, 0 to 20% ethyl acetate in petroleum ether) to afford methyl 4-[4-(tert-butoxycarbonylamino)-2-methyl-pyrazol-3-yl]but-3-enoate (700 mg, 51%) as a white solid. LCMS R$_T$=0.710 min, m/z=296.0 [M+H]$^+$.

LCMS (5 to 95% acetonitrile in water+0.03% trifluoroacetic acid over 1.5 mins) retention time 0.710 min, ESI+ found [M+H]=296.0.

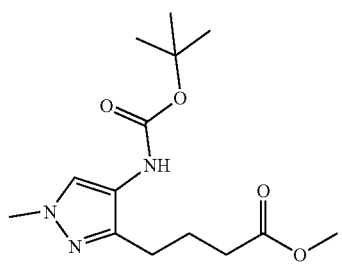

Step 6: methyl 4-(4-((tert-butoxycarbonyl)amino)-1-methyl-1H-pyrazol-3-yl)butanoate A mixture of methyl 4-[4-(tert-butoxycarbonylamino)-1-methyl-pyrazol-3-yl]but-3-enoate (700 mg, 2.38 mmol) and palladium (10% on carbon, 100 mg) in methyl alcohol (60 mL) was hydrogenated (15 psi) at 25° C. for 4 h and then filtered. The filtrate was concentrated under reduced pressure to afford crude methyl 4-[4-(tert-butoxycarbonylamino)-1-methyl-pyrazol-3-yl]butanoate (700 mg, 99%) as a yellow oil, used as is in the next step. LCMS R$_T$=0.719 min, m/z=298.1 [M+H]$^+$.

LCMS (5 to 95% acetonitrile in water+0.03% trifluoroacetic acid over 1.5 mins) retention time 0.719 min, ESI+ found [M+H]=298.1.

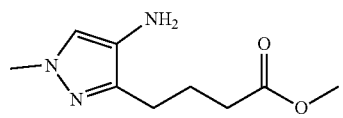

Step 7: methyl 4-(4-amino-1-methyl-1H-pyrazol-3-yl)butanoate

To a solution of methyl 4-[4-(tert-butoxycarbonylamino)-1-methyl-pyrazol-3-yl]butanoate (600 mg, 2.02 mmol) in 1,4-dioxane (5 mL) was added trifluoroacetic acid (230 mg). The reaction mixture was stirred at 25° C. for 15 h and concentrated under reduced pressure to afford crude methyl 4-(4-amino-1-methyl-pyrazol-3-yl)butanoate (300 mg, 75%) as a yellow oil, used as is in the next step.

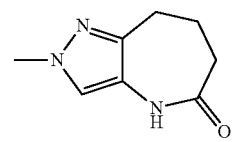

Step 8: 2-methyl-4,6,7,8-tetrahydropyrazolo[4,3-b]azepin-5(2H)-one

A mixture of methyl 4-(4-amino-1-methyl-pyrazol-3-yl) butanoate (300 mg, 1.52 mmol) and potassium carbonate (420 mg, 3.04 mmol) in N,N-dimethylformamide (5 mL) was stirred at 25° C. for 24 h and filtered. The filtrate was concentrated under reduced pressure. The residue was purified by column chromatography (silica gel, 100-200 mesh, 0 to 100% ethyl acetate in petroleum ether) to afford 2-methyl-4,6,7,8-tetrahydropyrazolo[4,3-b]azepin-5-one (229 mg, 80%) as a light yellow oil.

LC-MS R$_T$=1.102 min, m/z=204.1 [M+K]$^+$.

LCMS (0 to 60% acetonitrile in water+0.03% ammonium bicarbonate over 3.0 mins) retention time 1.102 min, ESI+ found [M+K]=204.1.

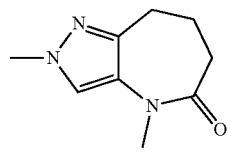

Step 9: 2,4-dimethyl-4,6,7,8-tetrahydropyrazolo[4,3-b]azepin-5(2H)-one

To a mixture of 2-methyl-4,6,7,8-tetrahydropyrazolo[4,3-b]azepin-5-one (229 mg, 1.39 mmol) and cesium carbonate (542 mg, 1.66 mmol) in N,N-dimethylformamide (20 mL) was added iodomethane (217 mg, 1.53 mmol). The mixture was stirred for 1 h at 25° C. and poured into water (20 mL). The mixture was extracted with dichloromethane/isopropanol (3:1, 2×20 mL). The combined organic layers were dried over anhydrous sodium sulfate and concentrated under reduced pressure to afford crude 2,4-dimethyl-7,8-dihydro-6H-pyrazolo[4,3-b]azepin-5-one (200 mg, 80%) as a brown solid, used as is in the next step. $^1$H NMR (400 MHz, CDCl$_3$) δ 7.19 (s, 1H), 3.84 (s, 4H), 3.23 (s, 3H), 2.85 (t, J=7.4 Hz, 2H), 2.55-2.47 (m, 2H), 2.22-2.12 (m, 2H).

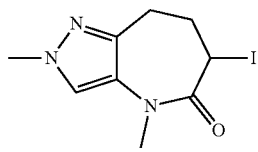

Step 10: 6-iodo-2,4-dimethyl-4,6,7,8-tetrahydropyrazolo[4,3-b]azepin-5(2H)-one

To a solution of 2,4-dimethyl-7,8-dihydro-6H-pyrazolo[4,3-b]azepin-5-one (200 mg, 1.10 mmol) in dichloromethane (40 mL) was added N$^1$,N$^1$,N$^2$,N$^2$-tetramethylethane-1,2-diamine (1.56 g, 13.39 mmol) and iodotrimethylsilane (1.34 g, 6.70 mmol) at −15° C. The mixture was stirred for 2 h at −15° C. and iodine (3.4 g, 13.40 mmol) was added. After addition, the mixture was stirred for 2 h and quenched by the addition of saturated sodium sulfite aqueous (50 mL). The resulting mixture was extracted with dichloromethane (3×50 mL). The combined organic layers were dried over sodium sulfate and concentrated under reduced pressure. The residue was purified by preparative TLC (100% ethyl acetate) to give 6-iodo-2,4-dimethyl-7,8-dihydro-6H-pyrazolo[4,3-b]azepin-5-one (200 mg, 59%) as a light yellow solid, used as is in the next step.

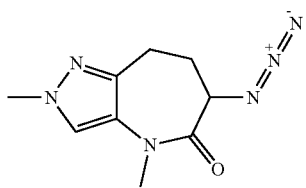

Step 11: 6-azido-2,4-dimethyl-4,6,7,8-tetrahydropyrazolo[4,3-b]azepin-5(2H)-one

To a solution of 6-iodo-2,4-dimethyl-7,8-dihydro-6H-pyrazolo[4,3-b]azepin-5-one (200 mg, 0.66 mmol) in N,N-dimethylformamide (15 mL) was added sodium azide (128 mg, 1.97 mmol). The reaction mixture was stirred at 25° C. for 2 h and diluted with ice water (5 mL). The resulting solution was extracted with ethyl acetate (3×10 mL). The combined organic layers were concentrated under reduced pressure. The residue was purified by preparative TLC (50% ethyl acetate in petroleum ether) to afford 6-azido-2,4-dimethyl-7,8-dihydro-6H-pyrazolo[4,3-b]azepin-5-one (140 mg, 97%) as a yellow oil. LCMS R$_T$=0.534 min, m/z=221.0 [M+H]$^+$.

LCMS (5 to 95% acetonitrile in water+0.03% trifluoroacetic acid over 1.5 mins) retention time 0.534 min, ESI+ found [M+H]=221.0.

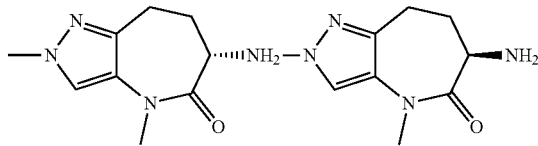 [SMILES: CN1C(=O)[C@H](N)CCc2nn(N[C@H]3CCc4nn(C)cc4N(C)C3=O)cc21]

Step 12: (S)-6-amino-2,4-dimethyl-4,6,7,8-tetrahydropyrazolo[4,3-b]azepin-5(2H)-one and (R)-6-amino-2,4-dimethyl-4,6,7,8-tetrahydropyrazolo[4,3-b]azepin-5(2H)-one A mixture of 6-azido-2,4-dimethyl-7,8-dihydro-6H-pyrazolo[4,3-b]azepin-5-one (140 mg, 0.64 mmol) and palladium (10% on carbon, 68 mg) in 1,4-dioxane (10 mL) was hydrogenated (15 psi) at 25° C. for 1 h and filtered. The filtrate was concentrated under reduced pressure to afford crude 6-amino-2,4-dimethyl-7,8-dihydro-6H-pyrazolo[4,3-b]azepin-5-one (100 mg, 81%) as a light yellow oil. LC-MS R$_T$=1.050 min, m/z=195.2 [M+H]$^+$.

LCMS (0 to 60% acetonitrile in water+0.03% ammonium bicarbonate over 3.0 mins) retention time 1.050 min, ESI+ found [M+H]=195.2.

Racemic 6-amino-2,4-dimethyl-7,8-dihydro-6H-pyrazolo[4,3-b]azepin-5-one (100 mg, 0.51 mmol) was separated by chiral SFC to afford arbitrarily assigned: (6S)-6-amino-2,4-dimethyl-7,8-dihydro-6H-pyrazolo[4,3-b]azepin-5-one (Peak 1, retention time=2.604 min) (35 mg, 35%) as a yellow oil.

(6R)-6-amino-2,4-dimethyl-7,8-dihydro-6H-pyrazolo[4,3-b]azepin-5-one (Peak 2, retention time=3.285 min) (35 mg, 35%) as yellow oil.

SFC conditions: Column: Chiralpak AS-3 150×4.6 mm I.D., 3 um, Mobile phase: A: CO$_2$ B: ethanol (0.05% DEA), Gradient: from 5% to 40% of B in 5 min and hold 40% for 2.5 min, then 5% of B for 2.5 min, Flow rate: 2.5 mL/min Column temp.: 35° C.

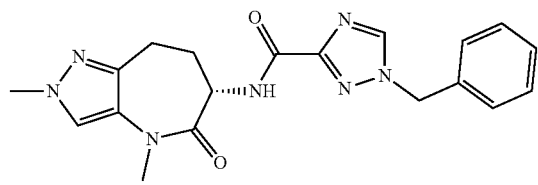 [SMILES: CN1C(=O)[C@@H](NC(=O)c2ncn(Cc3ccccc3)n2)CCc2nn(C)cc21]

Step 13: 1-benzyl-N-[(6S)-2,4-dimethyl-5-oxo-7,8-dihydro-6H-pyrazolo[4,3-b]azepin-6-yl]-1,2,4-triazole-3-carboxamide A mixture of 1-benzyl-1,2,4-triazole-3-carboxylic acid (16 mg, 0.08 mmol), (6S)-6-amino-2,4-dimethyl-7,8-dihydro-6H-pyrazolo[4,3-b]azepin-5-one (15 mg, 0.08 mmol), 1-(3-dimethylaminopropyl)-3-ethylcarbodiimidehydrochloride (15 mg, 0.08 mmol) and 1-hydroxybenzotriazole (10 mg, 0.08 mmol) in N,N-dimethylformamide (5 mL) was stirred at 30° C. for 2 h. The mixture was concentrated under reduce pressure. The residue was purified by RP-HPLC (acetonitrile 22-50%/0.05% hydrochloride acid in water) to afford 1-benzyl-N-[(6S)-2,4-dimethyl-5-oxo-7,8-dihydro-6H-pyrazolo[4,3-b]azepin-6-yl]-1,2,4-triazole-3-carboxamide (16.3 mg, 56%) as a white solid. ¹H NMR (400 MHz, CD₃OD) δ 8.81 (s, 1H), 7.84 (s, 1H), 7.38-7.33 (m, 5H), 5.51 (s, 2H), 4.73-4.68 (m, 1H), 3.93 (s, 3H), 3.31 (s, 3H), 3.00-2.90 (m, 2H), 2.50-2.45 (m, 1H), 2.27-2.22 (m, 1H). LCMS R_T=1.088 min, m/z=380.2 [M+H]⁺.

LCMS (5 to 95% acetonitrile in water+0.03% trifluoroacetic acid over 1.5 mins) retention time 1.088 min, ESI+ found [M+H]=380.2.

Example #21

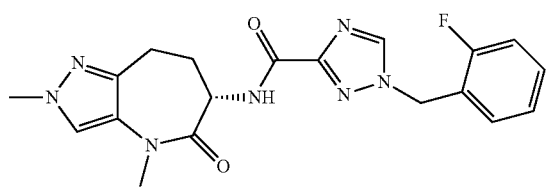 [SMILES: CN1C(=O)[C@@H](NC(=O)c2ncn(Cc3ccccc3F)n2)CCc2nn(C)cc21]

1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide Prepared in a similar fashion to Example #20. The crude was purified by RP-HPLC (acetonitrile 22-50%/0.05% hydrochloride acid in water) to afford 1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide (13.9 mg, 45%) as a white solid. ¹H NMR (400 MHz, CD₃OD) δ 8.84 (s, 1H), 7.88 (s, 1H), 7.42-7.40 (m, 2H), 7.23-7.16 (m, 2H), 5.59 (s, 2H), 4.72-4.68 (m, 1H), 3.93 (s, 3H), 3.32 (s, 3H), 3.06-2.89 (m, 2H), 2.53-2.43 (m, 1H), 2.32-2.21 (m, 1H). LCMS R_T=1.095 min, m/z=398.3 [M+H]⁺.

LCMS (5 to 95% acetonitrile in water+0.03% trifluoroacetic acid over 1.5 mins) retention time 1.095 min, ESI+ found [M+H]=398.3.

Example #22

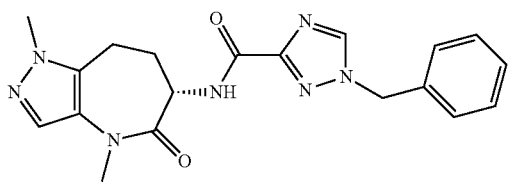 [SMILES: CN1C(=O)[C@@H](NC(=O)c2ncn(Cc3ccccc3)n2)CCc2c1cnn2C]

1-benzyl-N-[(6S)-1,4-dimethyl-5-oxo-7,8-dihydro-6H-pyrazolo[4,3-b]azepin-6-yl]-1,2,4-triazole-3-carboxamide

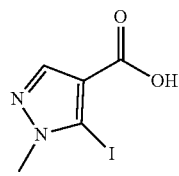

Step 1: 5-iodo-1-methyl-1H-pyrazole-4-carboxylic acid

A mixture of ethyl 5-iodo-1-methyl-pyrazole-4-carboxylate (7.5 g, 26.8 mmol) and lithium hydroxide (6.4 g, 268.0 mmol) in tetrahydrofuran (100 mL) and water (100 mL) was stirred at 25° C. for 15 h and concentrated under reduced pressure. The residue was adjusted to pH=5 by additional of hydrochloric acid (2 N). The formed solid was collected by filtration, washed with water (20 mL) and dried in vacuo to afford crude 5-iodo-1-methyl-1H-pyrazole-4-carboxylic acid (6.0 g, 89%) as a white solid, used as is in the next step.

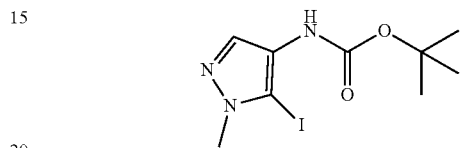

Step 2: tert-butyl (5-iodo-1-methyl-1H-pyrazol-4-yl)carbamate

To a stirred solution of 5-iodo-1-methyl-1H-pyrazole-4-carboxylic acid (3.0 g, 11.9 mmol) in t-butanol (120 mL) were added triethylamine (1.8 g, 17.9 mmol) and diphenylphosphoryl azide (3.6 g, 13.1 mmol). The reaction mixture was heated at 100° C. for 15 h and cooled. The mixture was diluted with ice water (200 mL) and extracted with dichloromethane (2×200 mL). The combined organic layers were dried over anhydrous sodium sulfate and concentrated under reduced pressure. The residue was purified by column chromatography (silica gel, 100-200 mesh, 0 to 30% ethyl acetate in petroleum ether) to give tert-butyl (5-iodo-1-methyl-1H-pyrazol-4-yl)carbamate (1.8 g, 47%) as a white solid. ¹H NMR (400 MHz, DMSO-d₆) δ 8.35 (s, 1H), 7.42 (br s, 1H), 3.79 (s, 3H), 1.43 (s, 9H).

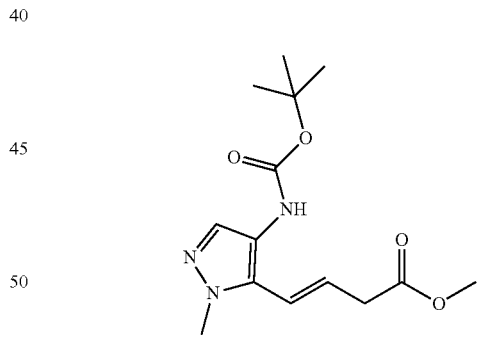

Step 3: (E)-methyl 4-(4-((tert-butoxycarbonyl)amino)-1-methyl-1H-pyrazol-5-yl)but-3-enoate A mixture of tert-butyl (5-iodo-1-methyl-1H-pyrazol-4-yl)carbamate (1.8 g, 5.57 mmol), methyl 3-butenoate (1.67 g, 16.7 mmol), sodium bicarbonate (1.4 g, 16.7 mmol) and dichloropalladium dicyclohexyl-[2-(2,4,6-triisopropyl-3-phenyl-phenyl) phenyl]phosphane (178 mg, 0.14 mmol) in N,N-dimethylformamide (33 mL) was heated at 110° C. for 40 min under microwave conditions. The mixture was poured into water (20 mL) and extracted with ethyl acetate (3×30 mL). The combined organic layers were dried over anhydrous sodium sulfate and concentrated under reduced pressure. The residue was purified by column chromatography (silica gel, 100-200 mesh, 0 to 70% ethyl acetate in petroleum ether) to afford (E)-methyl 4-(4-((tert-butoxycarbonyl)amino)-1-methyl-1H-pyrazol-5-yl)but-3-enoate (990 mg, 60%) as a white solid. $^1$H NMR (400 MHz, CD$_3$OD) δ 7.40 (br s, 1H), 3.77 (s, 3H), 3.65 (s, 3H), 2.70-2.65 (m, 2H), 2.38-2.34 (m, 2H), 1.89-1.81 (m, 2H), 1.49 (s, 9H).

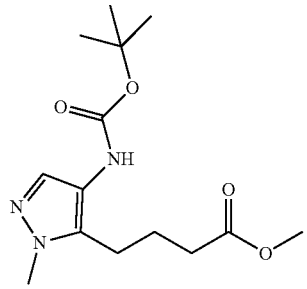 [SMILES: COC(=O)CCCc1c(NC(=O)OC(C)(C)C)cnn1C]

Step 4: methyl 4-(4-((tert-butoxycarbonyl)amino)-1-methyl-1H-pyrazol-5-yl)butanoate A mixture of (E)-methyl 4-(4-((tert-butoxycarbonyl)amino)-1-methyl-1H-pyrazol-5-yl) but-3-enoate (990 mg, 3.35 mmol) and palladium (10% on carbon, 100 mg) in methyl alcohol (50 mL) was hydrogenated (15 psi) at 25° C. for 4 h and filtered. The filtrate was concentrated under reduced pressure to give crude methyl 4-(4-((tert-butoxycarbonyl)amino)-1-methyl-1H-pyrazol-5-yl)butanoate (970 mg, 97%) as a yellow oil, used as is in the next step.

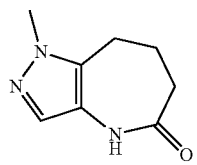

Step 5: 1-methyl-4,6,7,8-tetrahydropyrazolo[4,3-b]azepin-5(1H)-one

To a solution of methyl 4-(4-((tert-butoxycarbonyl)amino)-1-methyl-1H-pyrazol-5-yl) butanoate (970 mg, 3.26 mmol) in dichloromethane (5 mL) was added trifluoroacetic acid (1 mL). The reaction mixture was stirred at 25° C. for 15 min and concentrated under reduced pressure to afford crude methyl 4-(4-amino-1-methyl-1H-pyrazol-5-yl)butanoate as a yellow oil.

The above crude was dissolved in methanol (15 mL) and added potassium carbonate (4.5 g, 32.62 mmol). The mixture was stirred at 25° C. for 18 h and then filtered. The filtrate was concentrated under reduced pressure. The residue was purified by preparative TLC (10% methanol in dichloromethane, R$_f$=0.4) to afford 1-methyl-4,6,7,8-tetrahydropyrazolo[4,3-b]azepin-5-one (330 mg, 61%) as a white solid, used as is in the next step.

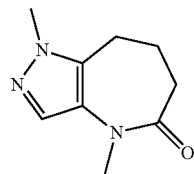

Step 6: 1,4-dimethyl-4,6,7,8-tetrahydropyrazolo[4,3-b]azepin-5(1H)-one

To a mixture of 1-methyl-4,6,7,8-tetrahydropyrazolo[4,3-b]azepin-5(1H)-one (290 mg, 1.76 mmol) and cesium carbonate (686 mg, 2.10 mmol) in N,N-dimethylformamide (10 mL) was added iodomethane (274 mg, 1.93 mmol). The mixture was stirred for 1 h at 25° C. and then poured into water (20 mL). The mixture was extracted with dichloromethane/isopropanol (3:1, 2×20 mL). The combined organic layers were dried over anhydrous sodium sulfate and concentrated under reduced pressure to afford crude 1,4-dimethyl-4,6,7,8-tetrahydropyrazolo[4,3-b]azepin-5(1H)-one (216 mg, 69%) as a brown solid, used as is in the next step. $^1$H NMR (400 MHz, CDCl$_3$) δ 7.31 (s, 1H), 3.75 (s, 3H), 3.28 (s, 3H), 2.82-2.80 (m, 2H), 2.61-2.54 (m, 2H), 2.18-2.10 (m, 2H).

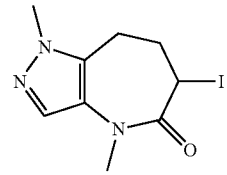

Step 7: 6-iodo-1,4-dimethyl-4,6,7,8-tetrahydropyrazolo[4,3-b]azepin-5(1H)-one

To a solution of 1,4-dimethyl-4,6,7,8-tetrahydropyrazolo[4,3-b]azepin-5(1H)-one (216 mg, 1.2 mmol) in dichloromethane (40 mL) was added N$^1$,N$^1$,N$^2$,N$^2$-tetramethylethane-1,2-diamine (840 mg, 7.2 mmol) and iodotrimethylsilane (1.44 g, 7.2 mmol) at −15° C. The mixture was stirred for 2 h at −15° C. and then iodine (3.7 g, 14.6 mmol) was added. The mixture was stirred at −15° C. for another 2 h and then quenched by the addition of saturated sodium sulfite aqueous (50 mL). The resulting mixture was extracted with dichloromethane (3×50 mL). The combined organic layers were dried over sodium sulfate and concentrated under reduced pressure. The residue was purified by preparative TLC (100% ethyl acetate) to give 6-iodo-1,4-dimethyl-4,6,7,8-tetrahydropyrazolo[4,3-b]azepin-5(1H)-one (250 mg, 68%) as a light yellow solid. $^1$H NMR (400 MHz, CDCl$_3$) δ 7.31 (s, 1H), 5.06-5.03 (m, 1H), 3.78 (s, 3H), 3.33 (s, 3H), 3.00-2.93 (m, 2H), 2.33-2.30 (m, 1H), 2.08-2.30 (m, 1H).

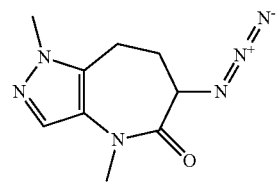 [SMILES: CN1C(=O)C(N=[N+]=[N-])CCc2c1cnn2C]

Step 8: 6-azido-1,4-dimethyl-4,6,7,8-tetrahydropyrazolo[4,3-b]azepin-5(1H)-one To a solution of 6-iodo-1,4-dimethyl-4,6,7,8-tetrahydropyrazolo[4,3-b]azepin-5(1H)-one (250 mg, 0.82 mmol) in N,N-dimethylformamide (5 mL) was added sodium azide (160 mg, 2.46 mmol). The reaction mixture was stirred at 25° C. for 2 h and diluted with ice water (5 mL). The mixture was extracted with ethyl acetate (3×10 mL). The combined organic layers were concentrated under reduced pressure. The residue was purified by preparative TLC (50% ethyl acetate in petroleum ether) to afford 6-azido-1,4-dimethyl-4,6,7,8-tetrahydropyrazolo[4,3-b]azepin-5(1H)-one (180 mg, 99%) as a yellow oil, used as is in the next step.

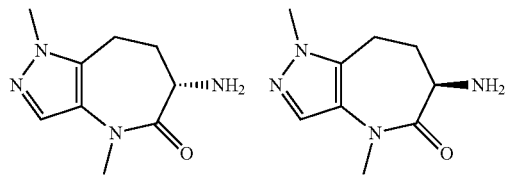

Step 9: (S)-6-amino-1,4-dimethyl-4,6,7,8-tetrahydropyrazolo[4,3-b]azepin-5(1H)-one and (R)-6-amino-1,4-dimethyl-4,6,7,8-tetrahydropyrazolo[4,3-b]azepin-5(1H)-one A mixture of 6-azido-1,4-dimethyl-4,6,7,8-tetrahydropyrazolo[4,3-b]azepin-5(1H)-one (180 mg, 0.82 mmol) and palladium (10% on carbon, 9 mg) in ethanol (10 mL) was hydrogenated (15 psi) at 25° C. for 1 h and then filtered. The filtrate was concentrated under reduced pressure to afford crude 6-amino-1,4-dimethyl-4,6,7,8-tetrahydropyrazolo[4,3-b]azepin-5(1H)-one.

The above crude was separated by chiral SFC to afford arbitrarily assigned: (S)-6-amino-1,4-dimethyl-4,6,7,8-tetrahydropyrazolo[4,3-b]azepin-5(1H)-one (Peak 1, retention time=3.123 min) (52 mg, 33%) as yellow oil.

(R)-6-amino-1,4-dimethyl-4,6,7,8-tetrahydropyrazolo[4,3-b]azepin-5(1H)-one (Peak 2, retention time=6.449 min) (53 mg, 33%) as yellow oil.

SFC conditions: Column: Lux Cellulose-2 150×4.6 mm I.D., 3 um, Mobile phase: A: $CO_2$ B: ethanol (0.05% DEA), Gradient: 40% of ethanol (0.05% DEA) in $CO_2$, Flow rate: 2.5 mL/min Column temp.: 35° C.

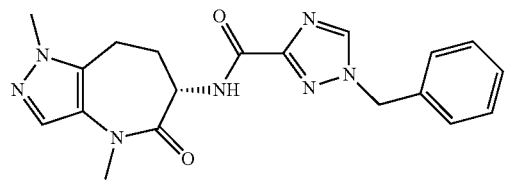 [SMILES: CN1C(=O)[C@@H](NC(=O)c2ncn(Cc3ccccc3)n2)CCc2c1cnn2C]

Step 10: 1-benzyl-N-[(6S)-1,4-dimethyl-5-oxo-7,8-dihydro-6H-pyrazolo[4,3-b]azepin-6-yl]-1,2,4-triazole-3-carboxamide A mixture of (6S)-6-amino-1,4-dimethyl-7,8-dihydro-6H-pyrazolo[4,3-b]azepin-5-one (15 mg, 0.08 mmol), 1-hydroxybenzotriazole (10 mg, 0.08 mmol), 1-(3-dimethylaminopropyl)-3-ethylcarbodiimidehydrochloride (22 mg, 0.12 mmol), and 1-[(2-fluorophenyl)methyl]-1,2,4-triazole-3-carboxylic acid (17 mg, 0.08 mmol) in N,N-dimethylformamide (1 mL) was s stirred at 30° C. for 2 h. The mixture was concentrated under reduce pressure. The residue was purified by RP-HPLC (acetonitrile 24-54%/0.05% ammonium hydroxide in water) to afford 1-benzyl-N-[(6S)-1,4-dimethyl-5-oxo-7,8-dihydro-6H-pyrazolo[4,3-b]azepin-6-yl]-1,2,4-triazole-3-carboxamide (8.32 mg, 27%) as a white solid. $^1$H NMR (400 MHz, $CD_3OD$) δ 8.56 (s, 1H), 7.48 (s, 1H), 7.35-7.31 (m, 5H), 5.46 (s, 2H), 4.59-4.55 (m, 1H), 3.77 (s, 3H), 3.28 (s, 3H), 3.13-3.10 (m, 1H), 2.95-2.92 (m, 1H), 2.41-2.40 (m, 1H), 2.19-2.16 (m, 1H). LCMS $R_T$=1.875 min, m/z=380.2 [M+H]$^+$.

LCMS (5 to 95% acetonitrile in water+0.03% trifluoroacetic acid over 1.5 mins) retention time 1.875 min, ESI+ found [M+H]=380.2.

Example #23

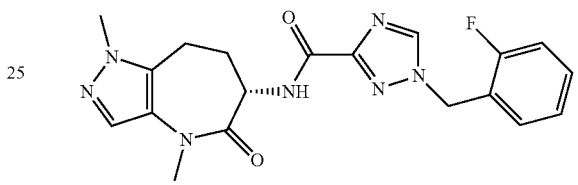

1-[(2-fluorophenyl)methyl]-N-[(6S)-1,4-dimethyl-5-oxo-7,8-dihydro-6H-pyrazolo[4,3-b]azepin-6-yl]-1,2,4-triazole-3-carboxamide Prepared in a similar fashion to Example #22. The crude was purified by purified by RP-HPLC (acetonitrile 24-54%/0.05% ammonium hydroxide in water) to afford 1-[(2-fluorophenyl)methyl]-N-[(6S)-1,4-dimethyl-5-oxo-7,8-dihydro-6H-pyrazolo[4,3-b]azepin-6-yl]-1,2,4-triazole-3-carboxamide (8.32 mg, 27%) as a white solid. $^1$H NMR (400 MHz, $CD_3OD$) δ 8.57 (s, 1H), 7.48 (s, 1H), 7.37 (t, J=6.8 Hz, 2H), 7.22-7.09 (m, 2H), 5.54 (s, 2H), 4.59-4.55 (m, 1H), 3.77 (s, 3H), 3.33 (s, 3H), 3.18-3.07 (m, 1H), 2.97-2.86 (m, 1H), 2.47-2.36 (m, 1H), 2.23-2.10 (m, 1H). LCMS $R_T$=1.433 min, m/z=398.1 [M+H]$^+$.

LCMS (5 to 95% acetonitrile in water+0.03% trifluoroacetic acid over 1.5 mins) retention time 1.433 min, ESI+ found [M+H]=398.1.

Example #24

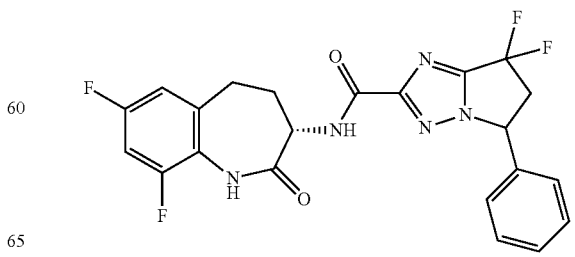

Step 1: (E)-benzaldehyde oxime

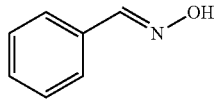

To a solution of benzaldehyde (45.0 g, 424.1 mmol) in ethanol (100 mL) was added sodium carbonate (112.3 g, 1060.1 mmol) and hydroxylamine hydrochloride (35.3 g, 508.9 mmol). The reaction mixture was stirred at 25° C. for 3 h and filtered. The filtrate was concentrated under reduced pressure and the residue was diluted with water (50 mL). The resulting mixture was extracted with ethyl acetate (3×150 mL). The combined organic layers were washed with brine (60 mL), dried over anhydrous sodium sulfate and concentrated under reduced pressure to afford crude (E)-benzaldehyde oxime as colorless oil (51.0 g, 99%), used in the next step without further purification.

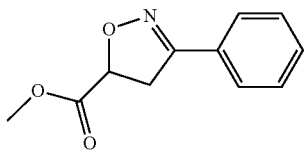

Step 2: methyl 3-phenyl-4,5-dihydroisoxazole-5-carboxylate

To a solution of (E)-benzaldehyde oxime (20.0 g, 165.1 mmol) in 1,4-dioxane (500 mL) was added methyl acrylate (14.2 g, 165.1 mmol), sodium iodide (24.7 g, 165.1 mmol), 2,6-lutidine (17.6 g, 165.1 mmol) and hypochlorous acid tert-butyl ester (17.9 g, 165.1 mmol). The reaction mixture was stirred at 25° C. for 24 h and subsequently concentrated under reduced pressure. The residue was purified by column chromatography (silica gel, 100-200 mesh, 0 to 20% ethyl acetate in petroleum ether) to afford methyl 3-phenyl-4,5-dihydroisoxazole-5-carboxylate as a yellow solid (25.0 g, 74%). LCMS $R_T$=0.871 min, m/z=206.2 [M+H]$^+$.

LCMS (10 to 80% acetonitrile in water+0.03% trifluoacetic acid over 2.0 mins) retention time 0.871 min, ESI+ found [M+H]=206.2.

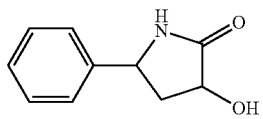 [SMILES: O=C1NC(c2ccccc2)CC1O]

Step 3: 3-hydroxy-5-phenyl-pyrrolidin-2-one

A mixture of methyl 3-phenyl-4,5-dihydroisoxazole-5-carboxylate (25.0 g, 121.8 mmol) and palladium (10% on carbon, 2.5 g) in ethanol (800 mL) was hydrogenated (50 psi) at 25° C. for 2 h and then filtered and the filtrate was concentrated under reduced pressure to afford crude 3-hydroxy-5-phenyl-pyrrolidin-2-one as a yellow solid (18.0 g, 83%), used in the next step without further purification. LCMS $R_T$=0.270 min, m/z=177.8 [M+H]$^-$.

LCMS (5 to 95% acetonitrile in water+0.03% trifluoacetic acid over 1.5 mins) retention time 0.270 min, ESI+ found [M+H]=177.8.

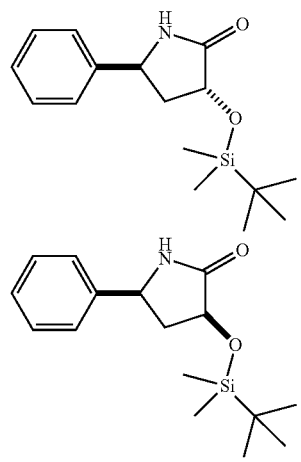

Step 4: cis-3-[tert-butyl(dimethyl)silyl]oxy-5-phenyl-pyrrolidin-2-one & trans-3-[tert-butyl(dimethyl)silyl]oxy-5-phenyl-pyrrolidin-2-one To a solution of 3-hydroxy-5-phenyl-pyrrolidin-2-one (15.0 g, 84.6 mmol) in dichloromethane (300 mL) was added tert-butyldimethylchlorosilane (19.1 g, 126.9 mmol) and imidazole (11.5 g, 169.3 mmol). The reaction mixture was stirred at 25° C. for 16 h and subsequently concentrated under reduced pressure. The residue was purified by column chromatography (silica gel, 100-200 mesh, 0 to 30% ethyl acetate in petroleum ether) to afford cis-3-[tert-butyl(dimethyl)silyl]oxy-5-phenyl-pyrrolidin-2-one (12.4 g, 51%). $^1$H NMR (400 MHz, CDCl$_3$) δ 7.37-7.25 (m, 5H), 4.88-4.53 (m, 1H), 4.54-4.46 (m, 1H), 2.89-2.79 (m, 1H), 1.80-1.71 (m, 1H), 0.93-0.90 (m, 9H), 0.19-0.12 (m, 6H) and trans-3-[tert-butyl(dimethyl)silyl]oxy-5-phenyl-pyrrolidin-2-one as a colorless oil (9.3 g, 38%). $^1$H NMR (400 MHz, CDCl$_3$) δ 7.44-7.34 (m, 2H), 7.29-7.24 (m, 3H), 4.87-4.80 (m, 1H), 4.44-4.41 (m, 1H), 2.45-2.37 (m, 1H), 2.27-2.22 (m, 1H), 0.93-0.90 (m, 9H), 0.16-0.13 (m, 6H).

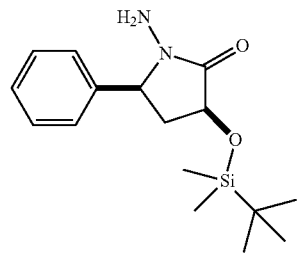

Step 5: cis-1-amino-3-[tert-butyl(dimethyl)silyl]oxy-5-phenyl-pyrrolidin-2-one To a solution of cis-3-[tert-butyl(dimethyl)silyl]oxy-5-phenyl-pyrrolidin-2-one (12.4 g, 42.8 mmol) in N,N-dimethylformamide (400 mL) was slowly added sodium hydride (60%, 2.6 g, 64.1 mmol) at 0° C. After addition, the mixture was stirred at 0° C. for 20 min and subsequently O-(diphenylphosphoryl)hydroxylamine (14.9 g, 64.1 mmol) was added. The reaction mixture was stirred at 25° C. for 16 h and then filtered. The filtrate was concentrated under reduced pressure to afford the crude cis-1-amino-3-[tert-butyl(dimethyl)silyl]oxy-5-phenyl-pyrrolidin-2-one as a yellow oil (9.5 g, 73%), used in the next step without further purification. LCMS $R_T$=0.877 min, m/z=307.0 [M+H]$^+$.

LCMS (5 to 95% acetonitrile in water+0.03% trifluoacetic acid over 1.5 mins) retention time 0.877 min, ESI+ found [M+H]=307.0.

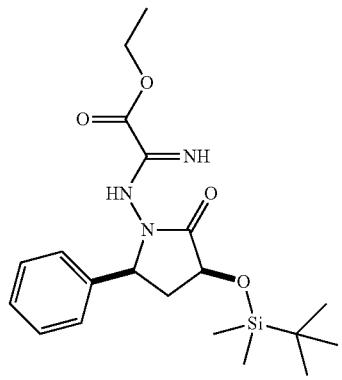 [SMILES: CCOC(=O)C(=N)NN1C(=O)[C@@H](O[Si](C)(C)C(C)(C)C)C[C@H]1c1ccccc1]

Step 6: ethyl 2-[[cis-3-[tert-butyl(dimethyl)silyl]oxy-2-oxo-5-phenyl-pyrrolidin-1-yl]amino]-2-imino-acetate To a solution of cis-1-amino-3-[tert-butyl(dimethyl)silyl]oxy-5-phenyl-pyrrolidin-2-one (9.5 g, 31.0 mmol) in ethanol (250 mL) was added ethyl 2-ethoxy-2-imino-acetate (6.7 g, 46.5 mmol). The reaction mixture was stirred at 60° C. for 6 h and subsequently concentrated under reduced pressure to afford crude ethyl 2-[[cis-3-[tert-butyl(dimethyl)silyl]oxy-2-oxo-5-phenyl-pyrrolidin-1-yl]amino]-2-imino-acetate as a yellow oil (10.6 g, 84%), used in the next step without further purification. LCMS $R_T$=2.106 min, m/z=406.2 [M+H]$^-$.

LCMS (10 to 80% acetonitrile in water+0.1% ammonia water over 3.0 mins) retention time 2.106 min, ESI+ found [M+H]=406.2.

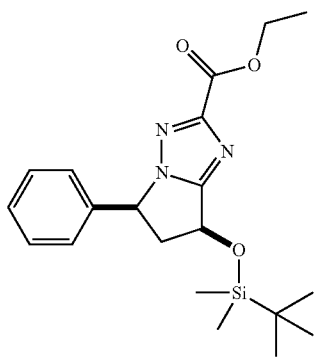 [SMILES: CCOC(=O)c1nc2n(n1)[C@H](c1ccccc1)C[C@@H]2O[Si](C)(C)C(C)(C)C]

Step 7: ethyl cis-7-[tert-butyl(dimethyl)silyl]oxy-5-phenyl-6,7-dihydro-5H-pyrrolo[1,2-b][1,2,4]triazole-2-carboxylate To a solution of ethyl 2-[[cis-3-[tert-butyl(dimethyl)silyl]oxy-2-oxo-5-phenyl-pyrrolidin-1-yl]amino]-2-imino-acetate (10.6 g, 26.1 mmol) in toluene (200 mL) was added p-toluenesulfonic acid (4.5 g, 26.1 mmol). The reaction mixture was heated at 120° C. for 24 h and subsequently concentrated under reduced pressure. The residue was purified by column chromatography (silica gel, 100-200 mesh, 0 to 80% ethyl acetate in petroleum ether) to afford ethyl cis-7-[tert-butyl(dimethyl)silyl]oxy-5-phenyl-6,7-dihydro-5H-pyrrolo[1,2-b][1,2,4]triazole-2-carboxylate as a white solid (6.5 g, 64%), used as is in the next step.

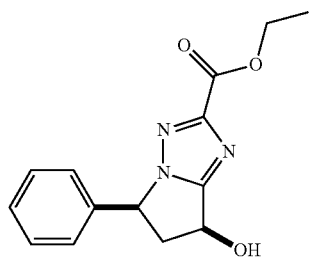 [SMILES: CCOC(=O)c1nc2n(n1)[C@H](c1ccccc1)C[C@@H]2O]

Step 8: ethyl cis-7-hydroxy-5-phenyl-6,7-dihydro-5H-pyrrolo[1,2-b][1,2,4]triazole-2-carboxylate A mixture of ethyl 2-[[cis-3-[tert-butyl(dimethyl)silyl]oxy-2-oxo-5-phenyl-pyrrolidin-1-yl]amino]-2-imino-acetate (3.1 g, 7.6 mmol) and tert-butylammonium fluoride (1.0 M in THF, 7.6 mL, 7.6 mmol) in tetrahydrofuran (60 mL) was heated at 60° C. for 18 h and subsequently concentrated under reduced pressure. The residue was purified by column chromatography (silica gel, 100-200 mesh, 0 to 100% ethyl acetate in petroleum ether) to give ethyl cis-7-hydroxy-5-phenyl-6,7-dihydro-5H-pyrrolo[1,2-b][1,2,4]triazole-2-carboxylate as white solid (1.4 g, 69%). $^1$H NMR (400 MHz, CDCl$_3$) δ7.39-7.32 (m, 5H), 5.73 (d, J=3.5 Hz, 1H), 5.50 (m, 1H), 4.41 (q, J=7.1 Hz, 2H), 3.73-3.65 (m, 1H), 2.76 (td, J=4.5 Hz, 13.9 Hz, 1H), 1.35 (t, J=7.1 Hz, 3H).

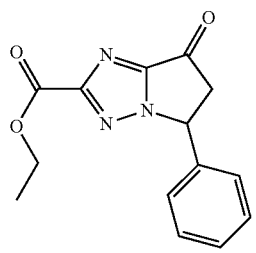 [SMILES: CCOC(=O)c1nc2n(n1)C(c1ccccc1)CC2=O]

Step 9: ethyl 7-oxo-5-phenyl-5,6-dihydropyrrolo[1,2-b][1,2,4]triazole-2-carboxylate To a solution of cis-7-hydroxy-5-phenyl-6,7-dihydro-5H-pyrrolo[1,2-b][1,2,4]triazole-2-carboxylate (1.0 g, 3.6 mmol) in dichloromethane (100 mL) was added manganese dioxide (0.9 g, 10.9 mmol). The mixture was heated at reflux for 3 h and subsequently filtered. The filtrate was concentrated under reduced pressure and the residue was purified by column chromatography (silica gel, 100-200 mesh, 0 to 50% ethyl acetate in petroleum ether) to afford ethyl 7-oxo-5-phenyl-5,6-dihydropyrrolo[1,2-b][1,2,4]triazole-2-carboxylate (350 mg, 35%) as a pink solid. LCMS $R_T$=0.725 min, m/z=271.9 [M+H]$^+$.

LCMS (5 to 95% acetonitrile in water+0.03% trifluoacetic acid over 1.5 mins) retention time 0.725 min, ESI+ found [M+H]=271.9.

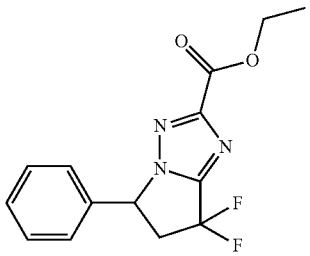 [SMILES: CCOC(=O)c1nc2n(n1)C(c1ccccc1)CC2(F)F]

Step 10: ethyl 7,7-difluoro-5-phenyl-5,6-dihydropyrrolo[1,2-b][1,2,4]triazole-2-carboxylate To a solution of ethyl 7-oxo-5-phenyl-5,6-dihydropyrrolo[1,2-b][1,2,4]triazole-2-carboxylate (300 mg, 1.1 mmol) in dichloromethane (10 mL) was added diethylaminosulfur trifluoride (1.78 g, 11.1 mmol) at 0° C. The reaction mixture was stirred at 25° C. for 2 h and subsequently quenched by addition of ice-water (20 mL). The mixture was extracted with dichloromethane (3×20 mL). The combined organic layers were washed with water (20 mL), brine (20 mL), dried over anhydrous sodium sulfate and concentrated under reduced pressure to afford crude ethyl 7,7-difluoro-5-phenyl-5,6-dihydropyrrolo[1,2-b][1,2,4]triazole-2-carboxylate as a yellow oil (280 mg, 86%), used in the next step without further purification. LCMS $R_T$=0.834 min, m/z=294.1 [M+H]$^+$.

LCMS (5 to 95% acetonitrile in water+0.03% trifluoacetic acid over 1.5 mins) retention time 0.834 min, ESI+ found [M+H]=294.1.

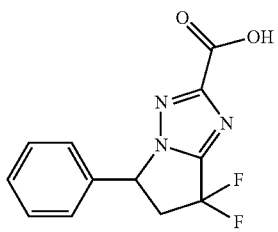 [SMILES: O=C(O)c1nc2n(n1)C(c1ccccc1)CC2(F)F]

Step 11: 7,7-difluoro-5-phenyl-5,6-dihydropyrrolo[1,2-b][1,2,4]triazole-2-carboxylic acid To a solution of ethyl 7,7-difluoro-5-phenyl-5,6-dihydropyrrolo[1,2-b][1,2,4]triazole-2-carboxylate (280 mg, 0.95 mmol) in tetrahydrofuran (10 mL) and water (2 mL) was added lithium hydroxide monohydrate (200 mg, 4.8 mmol). The reaction mixture was stirred at 25° C. for 3 h and subsequently concentrated under reduced pressure. The residue was adjusted to pH=5 by additional of hydrochloric acid (2 N). The resulting mixture was extracted with ethyl acetate (3×20 mL). The combined organic layers were washed with water (20 mL), brine (20 mL), dried over anhydrous sodium sulfate and concentrated under reduced pressure to afford crude 7,7-difluoro-5-phenyl-5,6-dihydropyrrolo[1,2-b][1,2,4]triazole-2-carboxylic acid as a yellow solid (240 mg, 95%), used in the next step without further purification.

Step 12: 7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide A mixture of 7,7-difluoro-5-phenyl-5,6-dihydropyrrolo[1,2-b][1,2,4]triazole-2-carboxylic acid (30 mg, 0.11 mmol), 1-hydroxybenzotriazole (23 mg, 0.17 mmol), 1-(3-dimethylaminopropyl)-3-ethylcarbodiimidehydrochloride (33 mg, 0.17 mmol), and (3S)-3-amino-7,9-difluoro-1,3,4,5-tetrahydro-1-benzazepin-2-one (29 mg, 0.14 mmol) in N,N-dimethylformamide (5 mL) was stirred at 25° C. for 2 h. The reaction mixture was concentrated under reduced pressure. The residue was purified by RP-HPLC (acetonitrile 42-72%/0.05% ammonia hydroxide in water) to afford 7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide (32.0 mg, 62%) as a white solid. $^1$H NMR (400 MHz, CD$_3$OD) δ 7.44-7.38 (m, 3H), 7.27-7.25 (m, 2H), 7.02-6.97 (m, 2H), 5.57-5.53 (m, 1H), 5.02-5.97 (m, 1H), 3.88-3.80 (m, 1H), 3.30-3.20 (m, 1H), 2.98-2.96 (m, 1H), 2.84-2.80 (m, 1H), 2.65-2.61 (m, 1H), 2.26-2.23 (m, 1H). LCMS: RT=0.736 min, m/z=460.1 [M+H]$^+$.

LCMS (5 to 95% acetonitrile in water+0.03% trifluoroacetic acid over 1.5 mins) retention time 0.736 min, ESI+ found [M+H]=460.1.

Example #25

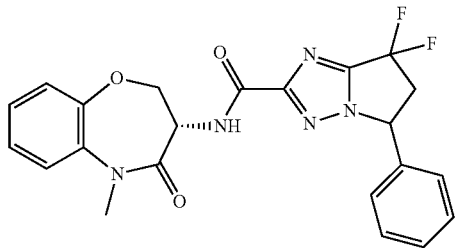 [SMILES: CN1C(=O)[C@@H](NC(=O)c2nc3n(n2)C(c2ccccc2)CC3(F)F)COc2ccccc21]

7,7-difluoro-5-phenyl-N-[(3S)-5-methyl-4-oxo-2,3-dihydro-1,5-benzoxazepin-3-yl]-5,6-dihydropyrrolo[1,2-b][1,2,4]triazole-2-carboxamide Prepared in a similar fashion to Example #24. The crude was purified by purified by RP-HPLC (acetonitrile 44-74%/0.05% ammonium hydroxide in water) to afford 7,7-difluoro-5-phenyl-N-[(3S)-5-methyl-4-oxo-2,3-dihydro-1,5-benzoxazepin-3-yl]-5,6-dihydropyrrolo[1,2-b][1,2,4]triazole-2-carboxamide (29.5 mg, 59%) as a white solid. $^1$H NMR (400 MHz, CD$_3$OD) δ 7.44-7.41 (m, 4H), 7.31-7.21 (m, 5H), 5.91-5.87 (m, 1H), 5.02-5.97 (m, 1H), 4.57-4.54 (m, 1H), 4.47-4.44 (m, 1H), 3.87-3.81 (m, 2H), 3.41 (s, 3H). LCMS: RT=0.749 min, m/z=440.1 [M+H]$^+$.

LCMS (5 to 95% acetonitrile in water+0.1% formic acid over 1.5 mins) retention time: 0.749 min, ESI+ found [M+H]=440.1.

Example #26

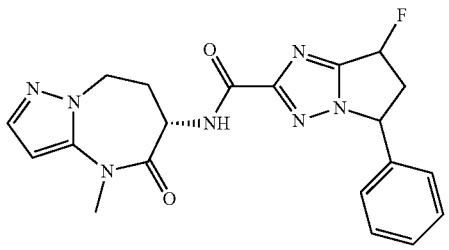 [SMILES: CN1C(=O)[C@@H](NC(=O)c2nc3n(n2)C(c2ccccc2)CC3F)CCn2nccc21]

7-fluoro-5-phenyl-N-[(6S)-4-methyl-5-oxo-7,8-di-hydro-6H-pyrazolo[1,5-a][1,3]diazepin-6-yl]-6,7-dihydro-5H-pyrrolo[1,2-b][1,2,4]triazole-2-carboxamide Prepared in a similar fashion to Example #24. A mixture of 7-fluoro-5-phenyl-6,7-dihydro-5H-pyrrolo[1,2-b][1,2,4]triazole-2-carboxylic acid (20 mg, 0.08 mmol), 1-hydroxybenzotriazole (16 mg, 0.12 mmol), 1-(3-dimethylaminopropyl)-3-ethylcarbodiimidehydrochloride (23 mg, 0.12 mmol) and (6S)-6-amino-4-methyl-7,8-dihydro-6H-pyrazolo[1,5-a][1,3]diazepin-5-one (17 mg, 0.10 mmol) in N,N-dimethylformamide (5 mL) was stirred at 25° C. for 2 h. The mixture was concentrated under reduced pressure. The residue was purified by RP-HPLC (acetonitrile 22-52%/0.05% ammonium hydroxide) to afford 7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (15 mg, 45%) as a white solid. $^1$H NMR (400 MHz, CD$_3$OD) δ 7.52 (d, J=4.0 Hz, 1H), 7.41-7.39 (m, 3H), 7.28-7.25 (m, 2H), 6.30 (d, J=2.0 Hz, 1H), 6.26-6.24 (m, 0.5H), 6.12-6.10 (m, 0.5H), 5.85-5.82 (m, 1H), 5.51-4.48 (m, 1H), 4.43-4.39 (m, 1H), 4.31-4.25 (m, 1H), 3.41-3.35 (m, 1H), 3.31 (s, 3H), 3.17-3.09 (m, 1H), 2.84-2.79 (m, 1H), 2.30-2.25 (m, 1H). LCMS R$_T$=0.763 min, m/z=410.0 [M+H]$^-$.

LCMS (5 to 95% acetonitrile in water+0.03% trifluoacetic acid over 1.5 mins) retention time: 0.763 min, ESI+ found [M+H]=410.0.

Example #27

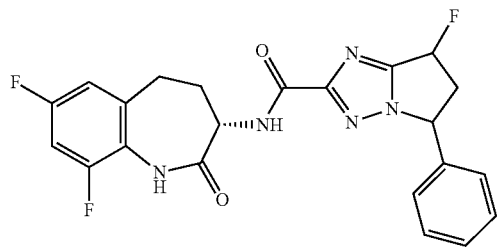 [SMILES: O=C(N[C@H]1CCc2cc(F)cc(F)c2NC1=O)c1nc2n(n1)C(c1ccccc1)CC2F]

7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Prepared in a similar fashion to Example #26. A mixture of 7-fluoro-5-phenyl-6,7-dihydro-5H-pyrrolo[1,2-b][1,2,4]triazole-2-carboxylic acid (20 mg, 0.08 mmol), 1-hydroxybenzotriazole (16 mg, 0.12 mmol), 1-(3-dimethylaminopropyl)-3-ethylcarbodiimidehydrochloride (23 mg, 0.12 mmol) and (3S)-3-amino-7,9-difluoro-1,3,4,5-tetrahydro-1-benzazepin-2-one (20 mg, 0.10 mmol) in N,N-dimethylformamide (5 mL) was stirred at 25° C. for 2 h. The mixture was concentrated under reduced pressure. The residue was purified by RP-HPLC (acetonitrile 35-65%/0.05% ammonium hydroxide in water) to afford 7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (13 mg, 36%) as a white solid. $^1$H NMR (400 MHz, CD$_3$OD) δ 7.41-7.38 (m, 3H), 7.28-7.25 (m, 2H), 7.02-6.97 (m, 2H), 6.26-6.24 (m, 0.5H), 6.12-6.10 (m, 0.5H), 5.86-5.82 (m, 1H), 4.59-4.54 (m, 1H), 3.46-3.36 (m, 1H), 2.99-2.96 (m, 1H), 2.84-2.82 (m, 1H), 2.81-2.78 (m, 1H), 2.66-2.62 (m, 1H), 2.24-2.18 (m, 1H). LCMS R$_T$=0.832 min, m/z=442.1 [M+H]$^+$.

LCMS (5 to 95% acetonitrile in water+0.03% trifluoacetic acid over 1.5 mins) retention time: 0.832 min, ESI+ found [M+H]=442.1.

Example #28

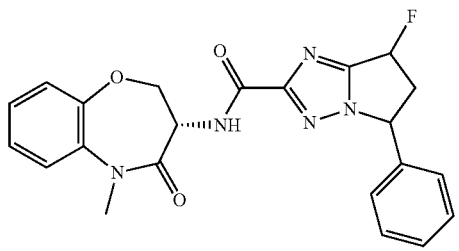 [SMILES: CN1C(=O)[C@@H](NC(=O)c2nc3n(n2)C(c2ccccc2)CC3F)COc2ccccc21]

7-fluoro-5-phenyl-N-[(3S)-5-methyl-4-oxo-2,3-di-hydro-1,5-benzoxazepin-3-yl]-6,7-dihydro-5H-pyrrolo[1,2-b][1,2,4]triazole-2-carboxamide Prepared in a similar fashion to Example #26. A mixture of 7-fluoro-5-phenyl-6,7-dihydro-5H-pyrrolo[1,2-b][1,2,4]triazole-2-carboxylic acid (20 mg, 0.08 mmol), 1-hydroxybenzotriazole (16 mg, 0.12 mmol), 1-(3-dimethylaminopropyl)-3-ethylcarbodiimidehydrochloride (23 mg, 0.12 mmol) and (3S)-3-amino-5-methyl-2,3-dihydro-1,5-benzoxazepin-4-one (19 mg, 0.10 mmol) in N,N-dimethylformamide (5 mL) was stirred at 25° C. for 2 h. The mixture was concentrated under reduced pressure. The residue was purified by RP-HPLC (acetonitrile 37-67%/0.05% ammonium hydroxide in water) to afford 7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (15 mg, 44%) as a white solid. $^1$H NMR (400 MHz, CD$_3$OD) δ 7.41-7.38 (m, 4H), 7.32-7.23 (m, 5H), 6.26-6.24 (m, 0.5H), 6.12-6.10 (m, 0.5H), 5.86-5.82 (m, 1H), 5.03-4.97 (m, 1H), 4.61-4.56 (m, 1H), 4.42-4.39 (m, 1H), 3.43-3.35 (m, 4H), 3.17-3.06 (m, 1H). LCMS R$_T$=0.855 min, m/z=422.1 [M+H]$^+$.

LCMS (5 to 95% acetonitrile in water+0.03% trifluoacetic acid over 1.5 mins) retention time: 0.855 min, ESI+ found [M+H]=422.1.

Example #29

(cis Mixture)

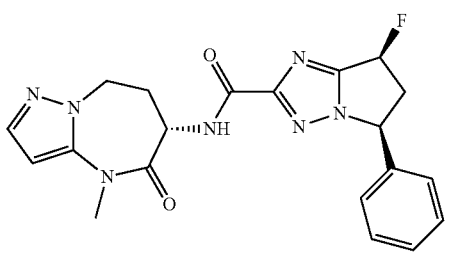 [SMILES: CN1C(=O)[C@@H](NC(=O)c2nc3n(n2)[C@H](c2ccccc2)C[C@@H]3F)CCn2nccc21]

Rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Prepared in a similar fashion to Example #26. A mixture of (6S)-6-amino-4-methyl-7,8-dihydro-6H-pyrazolo[1,5-a][1,3]diazepin-5-one (13 mg, 0.07 mmol), 1-hydroxybenzotriazole (12 mg, 0.09 mmol), 1-(3-dimethylaminopropyl)-3-ethylcarbodiimidehydrochloride (17 mg, 0.09 mmol) and rac-(5S,7S)-7-fluoro-5-phenyl-6,7-dihydro-5H-pyrrolo[1,2-b][1,2,4]triazole-2-carboxylic acid (18 mg, 0.07 mmol) in N,N-dimethylformamide (3 mL) was stirred at 25° C. for 15 h. The mixture was concentrated under reduced pressure. The residue was purified by RP-HPLC (acetonitrile 25-55%/0.05% ammonium hydroxide in water) to afford rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (14.7 mg, 48%) as a white solid. $^1$H NMR (400 MHz, CD$_3$OD) δ 7.52 (t, J=2.0 Hz, 1H), 7.42-7.34 (m, 3H), 7.26 (d, J=6.4 Hz, 2H), 6.30 (d, J=2.0 Hz, 1H), 6.17-6.01 (m, 1H), 5.70-5.61 (m, 1H), 4.52-4.48 (m, 1H), 4.45-4.39 (m, 1H), 4.31-4.24 (m, 1H), 3.80-3.69 (m, 1H), 3.35 (s, 3H), 2.87-2.75 (m, 2H), 2.32-2.24 (m, 1H). LCMS R$_T$=1.659 min, m/z=410.3 [M+H]$^+$.

LCMS (0 to 60% acetonitrile in water+0.03% trifluoroacetic acid over 3 mins) retention time 1.659 min, ESI+ found [M+H]=410.3.

Example #30

(cis Mixture)

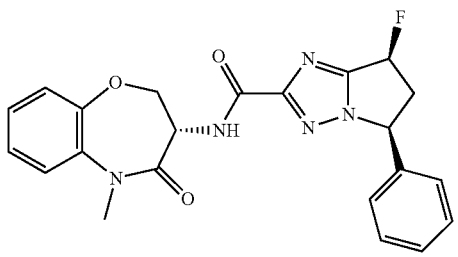 [SMILES: CN1C(=O)[C@@H](NC(=O)c2nc3n(n2)[C@H](c2ccccc2)C[C@@H]3F)COc2ccccc21]

Rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide Prepared in a similar fashion to Example #29. The crude was purified by purified by RP-HPLC (acetonitrile 40-70%/0.05% ammonium hydroxide in water) to afford rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (15 mg, 48%) as a white solid. $^1$H NMR (400 MHz, CD$_3$OD) δ 7.45-7.34 (m, 4H), 7.33-7.16 (m, 5H), 6.17-6.00 (m, 1H), 5.70-5.60 (m, 1H), 4.99 (dd, J=7.6, 11.2 Hz, 1H), 4.56-4.54 (m, 1H), 4.44-4.40 (m, 1H), 3.81-3.67 (m, 1H), 3.39 (s, 3H), 2.85-2.73 (m, 1H). LCMS R$_T$=1.886 min, m/z=422.2 [M+H]$^+$.

LCMS (0 to 60% acetonitrile in water+0.03% trifluoroacetic acid over 3 mins) retention time 1.886 min, ESI+ found [M+H]=422.2.

Example #31

(trans Mixture)

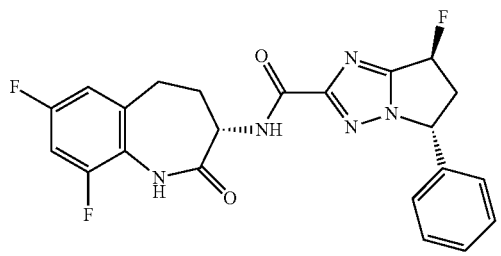 [SMILES: O=C(N[C@H]1CCc2cc(F)cc(F)c2NC1=O)c1nc2n(n1)[C@@H](c1ccccc1)C[C@@H]2F]

Rac-(5R,7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Prepared in a similar fashion to Example #29. A mixture of trans-7-fluoro-5-phenyl-6,7-dihydro-5H-pyrrolo[1,2-b][1,2,4]triazole-2-carboxylic acid (60 mg, 0.24 mmol), 1-hydroxybenzotriazole (34 mg, 0.25 mmol), 1-(3-dimethylaminopropyl)-3-ethylcarbodiimidehydrochloride (70 mg, 0.36 mmol) and (3S)-3-amino-7,9-difluoro-1,3,4,5-tetrahydro-1-benzazepin-2-one (77 mg, 0.36 mmol) in N,N-dimethylformamide (3 mL) was stirred at 25° C. for 15 h. The mixture was concentrated under reduced pressure. The residue was purified by RP-HPLC (acetonitrile 50 to 60%/0.05% ammonium hydroxide) to afford rac-(5R,7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (5.5 mg, 5%) as a white solid. $^1$H NMR (400 MHz, CD$_3$OD) δ 7.42-7.34 (m, 3H), 7.26-7.23 (m, 2H), 7.01-6.92 (m, 2H), 6.23 (d, J=5.6 Hz, 0.5H), 6.09 (d, J=5.2 Hz, 0.5H), 5.84-5.79 (m, 1H), 4.59-4.52 (m, 1H), 3.45-3.31 (m, 1H), 3.17-3.01 (m, 1H), 3.00-2.89 (m, 1H), 2.82-2.76 (m, 1H), 2.67-2.55 (m, 1H), 2.25-2.16 (m, 1H). LCMS R$_T$=1.009 min, m/z 442.2 [M+H]$^+$.

LCMS (10 to 80% acetonitrile in water+0.03% trifluoacetic acid over 2.0 mins) retention time 1.009 min, ESI+ found [M+H]=442.2.

Example #32

(trans Mixture)

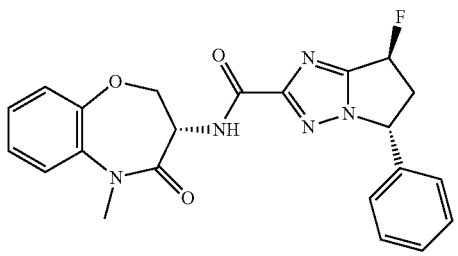 [SMILES: CN1C(=O)[C@@H](NC(=O)c2nc3n(n2)[C@@H](c2ccccc2)C[C@@H]3F)COc2ccccc21]

Rac-(5R,7S)—N-[(3S)-5-methyl-4-oxo-2,3-dihydro-1,5-benzoxazepin-3-yl]-6,7-dihydro-5H-pyrrolo[1,2-b][1,2,4]triazole-2-carboxamide Prepared in a similar fashion to Example #31. The crude was purified by purified by RP-HPLC (acetonitrile 46-56%/0.225% formic acid in water) to afford rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (7.8 mg, 8%) as a white solid. $^1$H NMR (400 MHz, CD$_3$OD) δ 7.42-7.36 (m, 4H), 7.31-7.24 (m, 4H), 7.22-7.18 (m, 1H), 6.23 (d, J=6.0 Hz, 0.5H), 6.10 (d, J=6.4 Hz, 0.5H), 5.87-5.80 (m, 1H), 5.05-4.96 (m, 1H), 4.56-4.53 (m, 1H), 4.43-4.34 (m, 1H), 3.45-3.30 (m, 4H), 3.17-3.02 (m, 1H). LCMS: R$_T$=1.042 min, m/z 422.2 [M+H]$^+$.

LCMS (10 to 80% acetonitrile in water+0.03% trifluoacetic acid over 2.0 mins) retention time 1.042 min, ESI+ found [M+H]=422.2.

Example #33

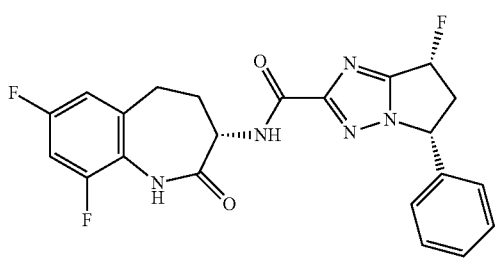 [SMILES: O=C(N[C@H]1CCc2cc(F)cc(F)c2NC1=O)c1nc2n(n1)[C@@H](c1ccccc1)C[C@H]2F]

(5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide A mixture of cis-7-fluoro-5-phenyl-6,7-dihydro-5H-pyrrolo[1,2-b][1,2,4]triazole-2-carboxylic acid (50 mg, 0.20 mmol), (3S)-3-amino-7,9-difluoro-1,3,4,5-tetrahydro-1-benzazepin-2-one (52 mg, 0.24 mmol), 1-(3-dimethylaminopropyl)-3-ethylcarbodiimidehydrochloride (58 mg, 0.30 mmol) and 1-hydroxybenzotriazole (29 mg, 0.21 mmol) in N,N-dimethylformamide (2 mL) was stirred at 25° C. for 15 h. The mixture was concentrated under reduced pressure. The residue was purified by RP-HPLC (acetonitrile 35-65%/0.05% ammonium hydroxide in water) to afford rac-(5R,7R)—N-[(3S)-7,9-difluoro-2-oxo-1,3,4,5-tetrahydro-1-benzazepin-3-yl]-7-fluoro-5-phenyl-6,7-dihydro-5H-pyrrolo[1,2-b][1,2,4]triazole-2-carboxamide, which was further separated by chiral SFC to afford arbitrarily assigned: (5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (peak 1, retention time=2.128 min) (4.9 mg, 5%) as a white solid. $^1$H NMR (400 MHz, CD$_3$OD) δ 7.44-7.30 (m, 3H), 7.29-7.18 (m, 2H), 7.02-6.92 (m, 2H), 6.14 (dd, J=2.0, 7.2 Hz, 0.5H), 6.00 (dd, J=2.0, 7.2 Hz, 0.5H), 5.64-5.52 (m, 1H), 4.57-4.52 (m, 1H), 3.81-3.62 (m, 1H), 3.02-2.89 (m, 1H), 2.86-2.71 (m, 2H), 2.68-2.53 (m, 1H), 2.26-2.17 (m, 1H). LCMS R$_T$=1.031 min, m/z=442.3 [M+H]$^+$.

LCMS (10 to 80% acetonitrile in water+0.03% trifluoacetic acid over 2.0 mins) retention time 1.031 min, ESI+ found [M+H]=442.3.

SFC conditions: Column: Chiralpak AS-H 150*4.6 mm I.D., 5 um, Mobile phase: A: CO2 B: ethanol (0.05% DEA), Gradient: hold 5% for 0.5 min, then from 5% to 40% of B in 3.5 min and hold 40% for 2.5 min, then 5% of B for 1.5 min, Flow rate: 3 mL/min Column temp: 40° C.

Example #34

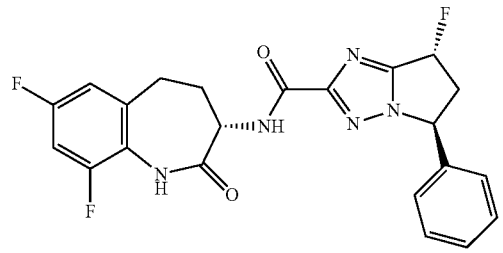 [SMILES: O=C(N[C@H]1CCc2cc(F)cc(F)c2NC1=O)c1nc2n(n1)[C@H](c1ccccc1)C[C@H]2F]

(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Prepared in a similar fashion to Example #31. The crude was purified by purified by RP-HPLC (acetonitrile 35 to 65%/0.05% ammonium hydroxide) to afford rac-(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (50 mg, 47%) as a white solid. The racemic mixture was further separated by chiral SFC to afford arbitrarily assigned:

(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (peak 1, retention time=1.220) (13.5 mg, 27%) as a white solid. $^1$H NMR (400 MHz, CD$_3$OD) δ 7.41-7.38 (m, 3H), 7.28-7.25 (m, 2H), 7.02-6.97 (m, 2H), 6.26-6.24 (m, 0.5H), 6.12-6.10 (m, 0.5H), 5.86-5.82 (m, 1H), 4.59-4.54 (m, 1H), 3.46-3.36 (m, 1H), 2.99-2.96 (m, 1H), 2.84-2.82 (m, 1H), 2.81-2.78 (m, 1H), 2.66-2.62 (m, 1H), 2.24-2.18 (m, 1H). LCMS R$_T$=0.821 min, m/z=442.1 [M+H]$^+$.

LCMS (5 to 95% acetonitrile in water+0.03% trifluoacetic acid over 1.5 mins) retention time: 0.821 min, ESI+ found [M+H]=442.1.

SFC conditions: Chiralcel OJ-3 50*4.6 mm I.D., 3 um; Mobile phase: A: CO2 B: ethanol (0.05% DEA);

Gradient: hold 5% for 0.2 min, then from 5% to 40% of B in 1.4 min and hold 40% for 1.05 min, then 5% of B for 0.35 min; Flow rate: 4 mL/min; Column temp: 40° C.

Example #35

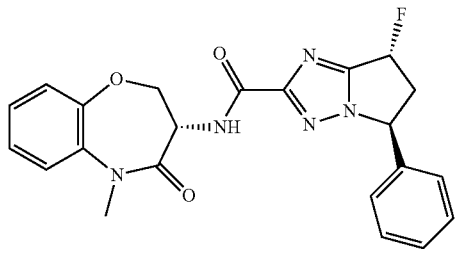 [SMILES: CN1C(=O)[C@@H](NC(=O)c2nc3n(n2)[C@H](c2ccccc2)C[C@H]3F)COc2ccccc21]

(5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide Prepared in a similar fashion to Example #31. The crude was purified by purified by RP-HPLC (acetonitrile 37 to 67%/0.05% ammonium hydroxide) to afford rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (50 mg, 49%) as a white solid. The racemic mixture was further separated by chiral SFC to afford arbitrarily assigned:

(5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (peak 1, retention time=1.188) (18.6 mg, 38%) as a white solid. $^1$H NMR (400 MHz, CD$_3$OD) δ 7.41-7.38 (m, 4H), 7.32-7.23 (m, 5H), 6.26-6.24 (m, 0.5H), 6.12-6.10 (m, 0.5H), 5.86-5.82 (m, 1H), 5.03-4.97 (m, 1H), 4.61-4.56 (m, 1H), 4.42-4.39 (m, 1H), 3.43-3.35 (m, 4H), 3.17-3.06 (m, 1H). LCMS R$_T$=0.849 min, m/z=422.1 [M+H]$^+$.

LCMS (5 to 95% acetonitrile in water+0.03% trifluoacetic acid over 1.5 mins) retention time: 0.849 min, ESI+ found [M+H]=422.1.

SFC conditions: Column: Chiralcel OJ-3 50*4.6 mm I.D., 3 um; Mobile phase: A: CO2 B: ethanol (0.05% DEA) Gradient: hold 5% for 0.2 min, then from 5% to 40% of B in 1.4 min and hold 40% for 1.05 min, then 5% of B for 0.35 min; Flow rate: 4 mL/min; Column temp: 40° C.

Example #36

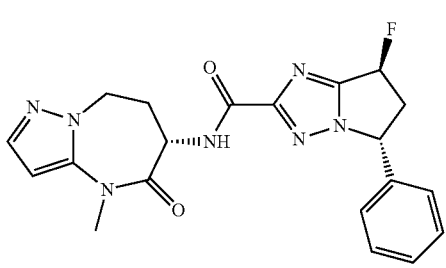 [SMILES: CN1C(=O)[C@@H](NC(=O)c2nc3n(n2)[C@@H](c2ccccc2)C[C@@H]3F)CCn2nccc21]

(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Prepared in a similar fashion to Example #31. The crude was purified by purified by RP-HPLC (acetonitrile 22 to 52%/0.05% ammonium hydroxide) to afford rac-(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (50 mg, 50%) as a white solid. The racemic mixture was further separated by chiral SFC to afford arbitrarily assigned:

(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (peak 2, retention time=1.274 min) (18 mg, 38%) as a white solid. $^1$H NMR (400 MHz, CD$_3$OD) δ 7.51 (d, J=2.0 Hz, 1H), 7.45-7.38 (m, 3H), 7.35-7.25 (m, 2H), 6.29 (d, J=2.4 Hz, 1H), 6.26-6.23 (m, 0.5H), 6.12-6.10 (m, 0.5H), 5.85-5.83 (m, 1H), 4.52-4.46 (m, 1H), 4.46-4.38 (m, 1H), 4.33-4.20 (m, 1H), 3.48-3.32 (m, 1H), 3.31 (s, 3H), 3.19-3.04 (m, 1H), 2.88-2.72 (m, 1H), 2.98-2.26 (m, 1H). LCMS R$_T$=0.765 min, m/z=410.1 [M+H]$^+$.

LCMS (5 to 95% acetonitrile in water+0.03% trifluoroacetic acid over 1.5 mins) retention time 0.765 min, ESI+ found [M+H]=410.1.

SFC conditions: Column: Chiralcel OJ-3 50*4.6 mm I.D., 3 um; Mobile phase: A: CO2 B: methanol (0.05% DEA); Gradient: hold 5% for 0.2 min, then from 5% to 40% of B in 1.4 min and hold 40% for 1.05 min, then 5% of B for 0.35 min; Flow rate: 4 mL/min; Column temp: 40° C.

Example #37

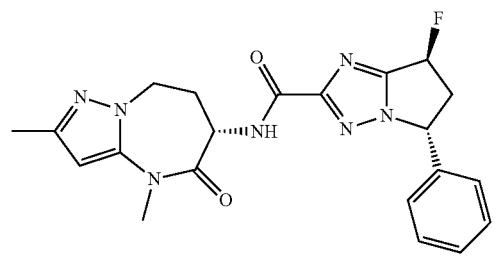 [SMILES: Cc1cc2n(n1)CC[C@H](NC(=O)c1nc3n(n1)[C@@H](c1ccccc1)C[C@@H]3F)C(=O)N2C]

(5R,7S)-7-fluoro-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Prepared in a similar fashion to Example #31. The crude was purified by purified by RP-HPLC (acetonitrile 28 to 58%/0.05% ammonium hydroxide) to afford rac-(5R,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (50 mg, 49%) as a white solid. The racemic mixture was further separated by chiral SFC to afford arbitrarily assigned:

(5R,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (peak 2, retention time=1.238 min) (16 mg, 31%) as a white solid. $^1$H NMR (400 MHz, CD$_3$OD) δ 7.41-7.38 (m, 3H), 7.28-7.25 (m, 2H), 6.26-6.24 (m, 0.5H), 6.12-6.10 (m, 1.5H), 5.86-5.82 (m, 1H), 4.51-4.48 (m, 1H), 4.31-4.27 (m, 1H), 4.24-4.20 (m, 1H), 3.50-3.42 (m, 1H), 3.31 (s, 3H), 3.17-3.09 (m, 1H), 2.84-2.79 (m, 1H), 2.29-2.20 (m, 4H). LCMS $R_T$=0.783 min, m/z=424.1 [M+H]$^+$.

LCMS (5 to 95% acetonitrile in water+0.03% trifluoacetic acid over 1.5 mins) retention time: 0.783 min, ESI+ found [M+H]=424.1.

Example #38 (SFC 1)

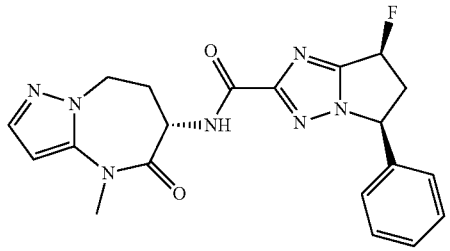 [SMILES: CN1C(=O)[C@@H](NC(=O)c2nc3n(n2)[C@H](c2ccccc2)C[C@@H]3F)CCn2nccc21]

rac-(5S,7S)-7-fluoro-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (3.17 mg, 22% yield)
Chiral Analytical
Sample Name: 82008679 SP pk1 Acquisition Method 7_Isocratic 20% MeOH Sample Set Name: SP 82008679_26_31 PURITY UV Wavelength: PDA Single 254.0 nm Project Name: 2016 Projects\October 2016 Column: Cellulose-3 Date Acquired: Oct. 27, 2016 9:20:42 AM Run Time: 2.5 Minutes Co-Solvent: MeOH w/0.1% NH4OH Injection Volume: 2.00 ul ColumnTemp: 40.0° C.

Example #39 (SFC 2)

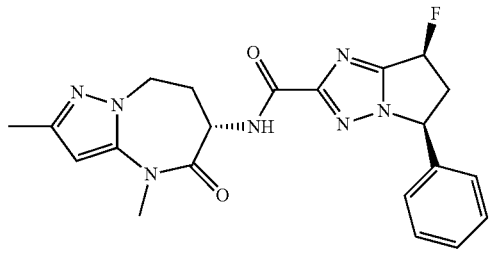 [SMILES: Cc1cc2n(n1)CC[C@H](NC(=O)c1nc3n(n1)[C@H](c1ccccc1)C[C@@H]3F)C(=O)N2C]

rac-(5S,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (3.7 mg, 23% yield)
Chiral Analytical
Sample Name: 82008726 SP pk1 Acquisition Method 7_Isocratic 20% MeOH Sample Set Name: SP 82008679_26_31 PURITY UV Wavelength: PDA Single 254.0 nm Project Name: 2016 Projects\October 2016 Column: Cellulose-3 Date Acquired: Oct. 27, 2016 9:26:42 AM Run Time: 2.5 Minutes Co-Solvent: MeOH w/0.1% NH4OH Injection Volume: 2.00 ul ColumnTemp: 40.0° C.

Example #40 (SFC 3)

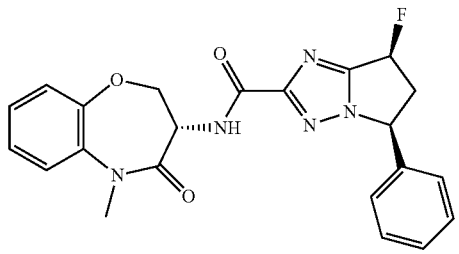 [SMILES: CN1C(=O)[C@@H](NC(=O)c2nc3n(n2)[C@H](c2ccccc2)C[C@@H]3F)COc2ccccc21]

(7.12 mg, 29% yield)
Chiral Analytical
Sample Name: 82010931 SP pk1 Acquisition Method 7_Isocratic 20% MeOH Sample Set Name: SP 82008679_26_31 PURITY UV Wavelength: PDA Single 254.0 nm Project Name: 2016 Projects\October 2016 Column: Cellulose-3 Date Acquired: Oct. 27, 2016 9:32:39 AM Run Time: 2.5 Minutes Co-Solvent: MeOH w/0.1% NH4OH Injection Volume: 2.00 ul ColumnTemp: 40.0° C.

Example #41 (SFC 4)

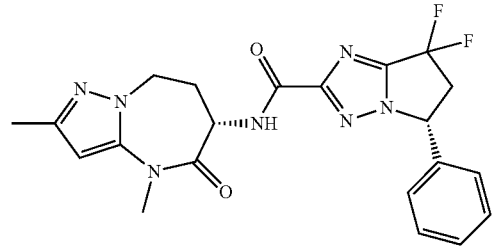 [SMILES: Cc1cc2n(n1)CC[C@H](NC(=O)c1nc3n(n1)[C@@H](c1ccccc1)CC3(F)F)C(=O)N2C]

rac-(5R)-7,7-difluoro-5-phenyl-N-[rac-(6S)-2,4-dimethyl-5-oxo-7,8-dihydro-6H-pyrazolo[1,5-a][1,3]diazepin-6-yl]-5,6-dihydropyrrolo[1,2-b][1,2,4]triazole-2-carboxamide (8.4 mg, 29% yield)
Chiral Analytical
Sample Name: 81888549 SP PK2 Acquisition Method 8_Isocratic 30% MeOH Sample Set Name: SP81888548_9 purity UV Wavelength: PDA Single 254.0 nm Project Name: 2016 Projects\August 2016 Column: Chiralpak IC Date Acquired: Aug. 30, 2016 4:05:13 PM Run Time: 2.5 Minutes Co-Solvent: MeOH w/0.1% NH4OH Injection Volume: 2.00 ul ColumnTemp: 40.0° C.

Example #42 (SFC 5)

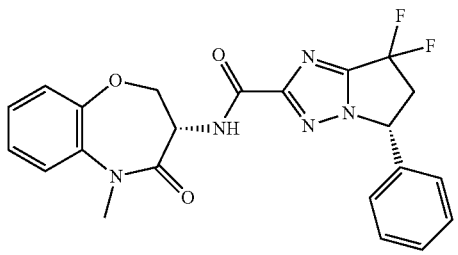 [SMILES: CN1C(=O)[C@@H](NC(=O)c2nc3n(n2)[C@@H](c2ccccc2)CC3(F)F)COc2ccccc21]

rac-(5R)-7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide (10.8 mg, 36% yield)

Chiral Analytical

Sample Name: 81888728 SP PK2 Acquisition Method 8_Isocratic 30% MeOH Sample Set Name: SP81888727_8 purity UV Wavelength: PDA Single 254.0 nm Project Name: 2016 Projects\August 2016 Column: Chiralpak IC Date Acquired: Aug. 30, 2016 4:19:41 PM Run Time: 2.5 Minutes Co-Solvent: MeOH w/0.1% NH4OH Injection Volume: 2.00 ul ColumnTemp: 40.0° C.

Example #43 (SFC 6)

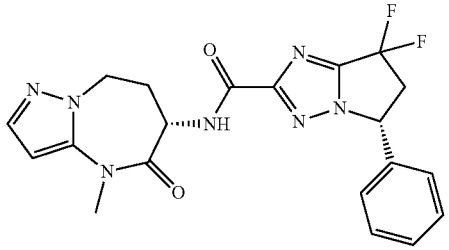 [SMILES: CN1C(=O)[C@@H](NC(=O)c2nc3n(n2)[C@@H](c2ccccc2)CC3(F)F)CCn2nccc21]

rac-(5R)-7,7-difluoro-5-phenyl-N-[rac-(6S)-4-methyl-5-oxo-7,8-dihydro-6H-pyrazolo[1,5-a][1,3]diazepin-6-yl]-5,6-dihydropyrrolo[1,2-b][1,2,4]triazole-2-carboxamide (8 mg, 26% yield)

Chiral Analytical

Sample Name: 81886337 SP PK2 Acquisition Method 9_Isocratic 35% MeOH Sample Set Name: SP81886336_7 purity UV Wavelength: PDA Single 254.0 nm Project Name: 2016 Projects\August 2016 Column: Chiralpak IC Date Acquired: Aug. 29, 2016 11:15:50 AM Run Time: 2.5 Minutes Co-Solvent: MeOH w/0.1% NH4OH Injection Volume: 2.00 ul ColumnTemp: 40.0

Example #44 (SFC 7)

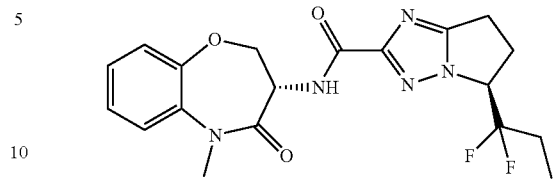

5-(1,1-difluoropropyl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (9.7 mg, 41% yield)

Chiral Analytical

Sample Name: 81822625 GH pk2 Acquisition Method 1_Isocratic 15% MeOH Sample Set Name: GH81822624_5 purity UV Wavelength: PDA Single 254.0 nm Project Name: 2016 Projects\June 2016 Column: AD Date Acquired: Jun. 20, 2016 4:17:34 PM Run Time: 2.5 Minutes Co-Solvent: MeOH w/0.1% NH4OH Injection Volume: 2.00 ul ColumnTemp: 40.0° C.

Example 45: RIP1 Kinase Inhibition Assays (Biochemical Assay)

The compounds of the present invention were tested for their capacity to inhibit RIP1K activity as described below.

Enzyme Assay:

The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph 7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. *Methods Enzymol* 63: 437-67]. The following equation was used to calculate fractional activity and $K_i^{app}$:

Fractional activity =

$$\frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in the following Tables along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers.

TABLE 1

| Compound Example # | RIP1 Ki (μM) | Structure and Name | Stereo-chemistry | $^1$H NMR Data | MS (m/z) R.T. |
|---|---|---|---|---|---|
| Example #9 | 0.021 | 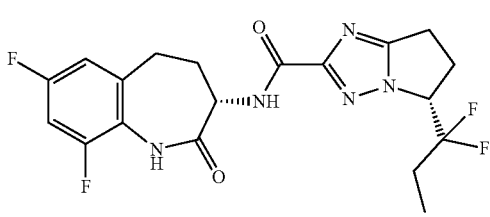 [SMILES: CCC(F)(F)[C@H]1CCc2nc(C(=O)N[C@H]3CCc4cc(F)cc(F)c4NC3=O)nn21]<br>(5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Single Unknown Stereo-isomer | $^1$H NMR (400 MHz, CD$_3$OD) δ 7.04-6.98 (m, 2H), 4.60-4.55 (m, 2H), 3.01-2.95 (m, 3H), 2.89-2.79 (m, 2H), 2.71-2.64 (m, 1H), 2.29-2.18 (m, 2H), 2.18-2.02 (m, 2H), 1.10 (t, J = 7.2 Hz, 3H). | 426.3 1.747 min |
| Example #10 | 0.009 | 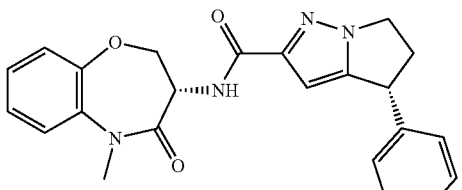<br>(4R)-4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide | Single Unknown Stereo-isomer | $^1$H NMR (400 MHz, CD$_3$OD) δ 7.45-7.42 (m, 1H), 7.35-7.29 (m, 4H), 7.25-7.20 (m, 4H), 6.37 (s, 1H), 4.99-4.96 (m, 1H), 4.59-4.56 (m, 1H), 4.52-4.48 (m, 1H), 4.42-4.34 (m, 2H), 4.25-4.20 (m, 1H), 3.42 (s, 3H), 3.15-3.10 (m 1H), 2.56-2.51 (m, 1H). | 403.2 1.960 min |
| Example #32 | 0.014 | 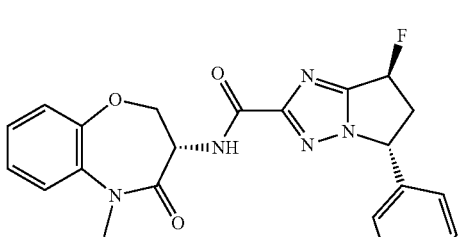<br>rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | $^1$H NMR (400 MHz, CD$_3$OD) δ 7.42-7.36 (m, 4H), 7.31-7.24 (m, 4H), 7.22-7.18 (m, 1H), 6.23 (d, J = 6.0 Hz, 0.5H), 6.10 (d, J = 6.4 Hz, 0.5H), 5.87-5.80 (m, 1H), 5.05-4.96 (m, 1H), 4.56-4.53 (m, 1H), 4.43-4.34 (m, 1H), 3.45-3.30 (m, 4H), 3.17-3.02 (m, 1H). | 422.2 1.042 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #31 | 0.015 | 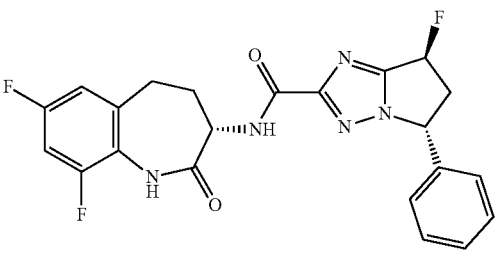 [SMILES: O=C(N[C@H]1CCc2cc(F)cc(F)c2NC1=O)c1nc2n(n1)[C@@H](c1ccccc1)C[C@@H]2F]<br>rac-(5R,7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Mixture of Diastereomers | ¹H NMR (400 MHz, CD₃OD) δ 7.42-7.34 (m, 3H), 7.26-7.23 (m, 2H), 7.01-6.92 (m, 2H), 6.23 (d, J = 5.6 Hz, 0.5H), 6.09 (d, J = 5.2 Hz, 0.5H), 5.84-5.79 (m, 1H), 4.59-4.52 (m, 1H), 3.45-3.31 (m, 1H), 3.17-3.01 (m, 1H), 3.00-2.89 (m, 1H), 2.82-2.76 (m, 1H), 2.67-2.55 (m, 1H), 2.25-2.16 (m, 1H). | 422.2 1.009 min |
| Example #33 | 0.013 | 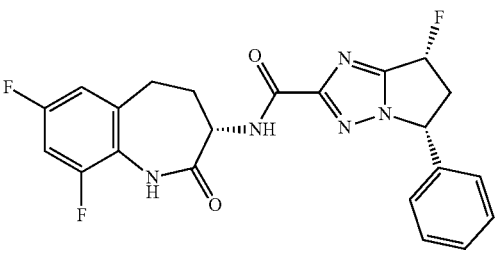 [SMILES: O=C(N[C@H]1CCc2cc(F)cc(F)c2NC1=O)c1nc2n(n1)[C@@H](c1ccccc1)C[C@H]2F]<br>(5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Single Unknown Stereo-isomer | ¹H NMR (400 MHz, CD₃OD) δ 7.44-7.30 (m, 3H), 7.29-7.18 (m, 2H), 7.02-6.92 (m, 2H), 6.14 (dd, J = 2.0, 7.2 Hz, 0.5H), 6.00 (dd, J = 2.0, 7.2 Hz, 0.5H), 5.64-5.52 (m, 1H), 4.57-4.52 (m, 1H), 3.81-3.62 (m, 1H), 3.02-2.89 (m, 1H), 2.86-2.71 (m, 2H), 2.68-2.53 (m, 1H), 2.26-2.17 (m, 1H). | 422.2 1.031 min |
| Example #3 | 0.035 | 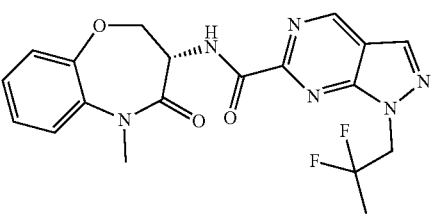 [SMILES: CN1C(=O)[C@@H](NC(=O)c2ncc3cnn(CC(C)(F)F)c3n2)COc2ccccc21]<br>1-(2,2-difluoropropyl)-N-[(3S)-5-methyl-4-oxo-2,3-dihydro-1,5-benzoxazepin-3-yl]pyrazolo[3,4-d]pyrimidine-6-carboxamide | Single Known Stereo-isomer | ¹H NMR (400 MHz, CD₃OD) δ 9.43 (s, 1H), 8.47 (s, 1H), 7.48-7.28 (m, 4H), 5.10-5.01 (m, 3H), 4.74-4.69 (m, 1H), 4.51-4.45 (m, 1H), 3.46 (s, 3H), 1.71 (t, J = 18.8 Hz, 3H). | 417.1 1.625 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #4 | 0.022 | 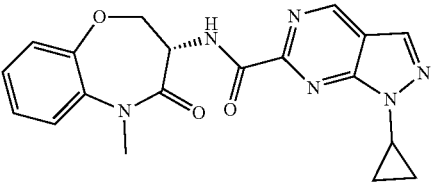 [SMILES: CN1C(=O)[C@@H](NC(=O)c2ncc3cnn(C4CC4)c3n2)COc2ccccc21]<br>1-cyclopropyl-N-[(3S)-5-methyl-4-oxo-2,3-dihydro-1,5-benzoxazepin-3-yl]pyrazolo[3,4-d]pyrimidine-6-carboxamide | Single Known Stereo-isomer | ¹H NMR (400 MHz, CD₃OD) δ 9.34 (s, 1H), 8.31 (s, 1H), 7.49-7.43 (m, 1H), 7.37-7.30 (m, 2H), 7.30-7.24 (m, 1H), 5.08-5.06 (m, 1H), 4.74-4.70 (m, 1H), 4.49-4.43 (m, 1H), 4.15-4.10 (m, 1H), 3.45 (s, 3H), 1.40-1.31 (m, 2H), 1.26-1.18 (m, 2H). | 379.0 0.785 min |
| Example #12 | 0.024 | 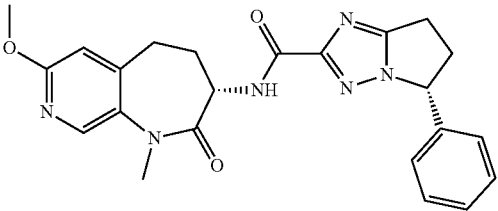 [SMILES: COc1cc2c(cn1)N(C)C(=O)[C@@H](NC(=O)c1nc3n(n1)[C@@H](c1ccccc1)CC3)CC2]<br>(5R)-5-phenyl-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide | Single Unknown Stereo-isomer | ¹H NMR (400 MHz, CD₃OD) δ 8.13 (s, 1H), 7.40-7.34 (m, 3H), 7.21-7.20 (m, 2H), 6.77 (s, 1H), 5.55-5.51 (m, 1H), 4.54-4.49 (m, 1H), 3.92 (s, 3H), 3.39 (s, 3H), 3.30-3.24 (m, 1H), 3.06-3.04 (m, 2H), 2.81-2.70 (m, 3H), 2.50-2.48 (m, 1H), 2.15-2.13 (m, 1H) | 433.0 0.731 min |
| Example #13 | 0.041 | 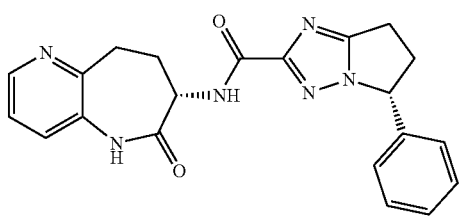 [SMILES: O=C(N[C@H]1CCc2ncccc2NC1=O)c1nc2n(n1)[C@@H](c1ccccc1)CC2]<br>(5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide | Single Unknown Stereo-isomer | ¹H NMR (400 MHz, CDCl₃) δ 8.43-8.35 (m, 1H), 8.17 (s, 1H), 7.95 (d, J = 2.0 Hz, 1H), 7.40-7.29 (m, 4H), 7.23-7.17 (m, 1H), 7.13-7.06 (m, 2H), 5.50-5.40 (m, 1H), 4.82-4.73 (m, 1H), 3.27-3.08 (m, 3H), 3.06-2.90 (m, 3H), 2.72-2.61 (m, 1H), 2.22-2.09 (m, 1H). | 389.2 1.314 min |
| Example #9 | 0.014 | 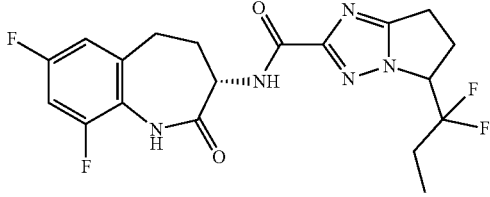 [SMILES: CCC(F)(F)C1CCc2nc(C(=O)N[C@H]3CCc4cc(F)cc(F)c4NC3=O)nn21]<br>5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Mixture of Diastereomers | ¹HNMR (400 MHz, CD₃OD) δ 7.02-6.99 (m, 2H), 4.86-4.82 (m, 1H), 4.65-4.54 (m, 1H), 3.10-2.79 (m, 6H), 2.77-2.63 (m, 1H), 2.31-2.03 (m, 3H), 1.12 (t, J = 7.2 Hz, 3H). | 426.2 0.989 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #30 | 0.018 | 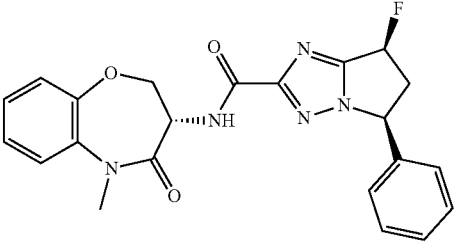 [SMILES: CN1C(=O)[C@@H](NC(=O)c2nc3n(n2)[C@H](c2ccccc2)C[C@@H]3F)COc2ccccc21]<br>rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | ¹H NMR (400 MHz, CD₃OD) δ 7.45-7.34 (m, 4H), 7.33-7.16 (m, 5H), 6.17-6.00 (m, 1H), 5.70-5.60 (m, 1H), 4.99 (dd, J = 7.6, 11.2 Hz, 1H), 4.56-4.54 (m, 1H), 4.44-4.40 (m, 1H), 3.81-3.67 (m, 1H), 3.39 (s, 3H), 2.85-2.73 (m, 1H). | 422.2 1.886 min |
| Example #29 | 0.043 | 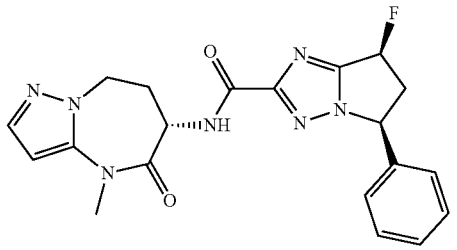 [SMILES: CN1C(=O)[C@@H](NC(=O)c2nc3n(n2)[C@H](c2ccccc2)C[C@@H]3F)CCn2nccc21]<br>rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Mixture of Diastereomers | ¹H NMR (400 MHz, CD₃OD) δ 7.52 (t, J = 2.0 Hz, 1H), 7.42-7.34 (m, 3H), 7.26 (d, J = 6.4 Hz, 2H), 6.30 (d, J = 2.0 Hz, 1H), 6.17-6.01 (m, 1H), 5.70-5.61 (m, 1H), 4.52-4.48 (m, 1H), 4.45-4.39 (m, 1H), 4.31-4.24 (m, 1H), 3.80-3.69 (m, 1H), 3.35 (s, 3H), 2.87-2.75 (m, 2H), 2.32-2.24 (m, 1H). | 410.3 1.659 min |
| Example #11 | 0.011 | 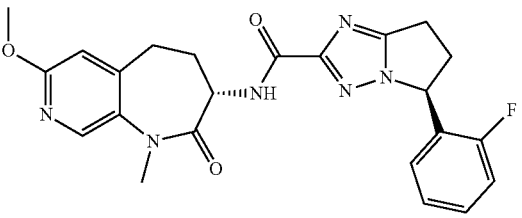 [SMILES: COc1cc2c(cn1)N(C)C(=O)[C@@H](NC(=O)c1nc3n(n1)[C@H](c1ccccc1F)CC3)CC2]<br>(5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide | Single Unknown Stereo-isomer | ¹H NMR (400 MHz, CD₃OD) δ 8.14 (s, 1H), 7.43-7.36 (m, 1H), 7.22-7.13 (m, 3H), 6.78 (s, 1H), 5.79-5.74 (m, 1H), 4.56-4.50 (m, 1H), 3.93 (s, 3H), 3.40 (s, 3H), 3.34-3.29 (m, 1H), 3.13-3.08 (m, 2H), 2.85-2.81 (m, 1H), 2.76-2.70 (m, 2H), 2.54-2.48 (m, 1H), 2.18-2.13 (m, 1H). | 451.0 0.818 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #14 | 0.019 | 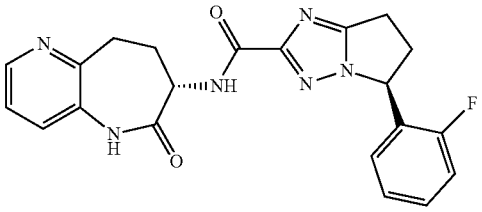 [SMILES: O=C(N[C@H]1CCc2ncccc2NC1=O)c1nc2n(n1)[C@H](c1ccccc1F)CC2]<br>(5S)-5-(2-fluorophenyl)-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide | Single Unknown Stereo-isomer | ¹H NMR (400 MHz, CD₃OD) δ 8.33 (d, J = 4.8 Hz, 1H), 7.51 (dd, J = 1.6, 8.0 Hz, 1H), 7.39-7.37 (m, 2H), 7.20-7.15 (m, 3H), 5.77 (dd, J = 5.6, 8.8 Hz, 1H), 4.56 (dd, J = 8.0, 11.8 Hz, 1H), 3.30-3.25 (m, 1H), 3.23-3.06 (m, 3H), 3.02-2.90 (m, 1H), 2.79-2.66 (m, 2H), 2.36-2.26 (m, 1H). | 407.2 1.384 min |
| Example #16 | 0.029 | 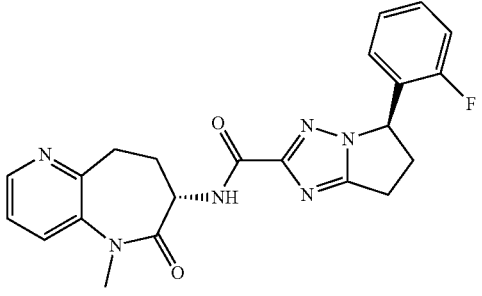 [SMILES: CN1C(=O)[C@@H](NC(=O)c2nc3n(n2)[C@@H](c2ccccc2F)CC3)CCc2ncccc21]<br>(5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide | Single Unknown Stereo-isomer | 1H NMR (400 MHz, CD₃OD) δ 8.39 (d, J = 5.2 Hz, 1H), 7.83 (d, J = 8.0 Hz, 1H), 7.48-7.44 (m, 1H), 7.43-7.36 (m,1H), 7.20-7.15 (m, 3H), 5.79-5.74 (m, 1H), 4.51 (dd, J = 8.0, 11.6 Hz, 1H), 3.41 (s, 3H), 3.29-3.24 (m, 1H), 3.20-3.03 (m, 3H), 2.95-2.87 (m, 1H), 2.76-2.67 (m, 1H), 2.66-2.57 (m, 1H), 2.33-2.22 (m, 1H). | 421.2 1.454 min |
| Example #10 | 0.028 | 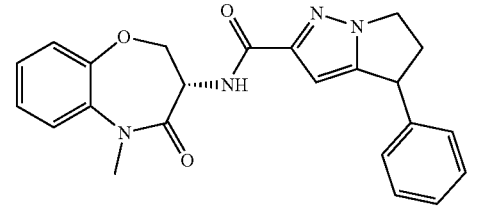 [SMILES: CN1C(=O)[C@@H](NC(=O)c2cc3n(n2)CCC3c2ccccc2)COc2ccccc21]<br>4-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide | Mixture of Diastereomers | 1H NMR (400 MHz, CD₃OD) δ 7.50-7.40 (m, 1H), 7.37-7.20 (m, 8H), 6.38 (s, 1H), 5.02-4.96 (m, 1H), 4.65-4.56 (m, 1H), 4.55-4.46 (m, 1H), 4.45-4.27 (m, 2H), 4.25-4.18 (m, 1H), 3.42 (s, 3H), 3.15-3.09 (m, 1H), 2.56-2.52 (m, 1H). | 403.1 0.875 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #6 | 0.004 | (4S)-4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide | Single Unknown Stereoisomer | ¹H NMR (400 MHz, CD₃OD) δ 7.43-7.40 (m, 1H), 7.37 (s, 5H), 7.33-7.26 (m, 2H), 7.23-7.19 (m, 1H), 6.18 (s, 1H), 5.80 (s, 1H), 4.97-4.94 (m, 1H), 4.57-4.53 (m, 1H), 4.41-4.34 (m, 3H), 4.32-4.26 (m, 1H), 4.21-4.14 (m, 1H), 3.40 (s, 3H) | 419.2 1.899 min, |
| Example #5 | 0.011 | 4-phenyl-N-[(3S)-7,9-difluoro-2-oxo-1,3,4,5-tetrahydro-1-benzazepin-3-yl]-6,7-dihydro-4H-pyrazolo[5,1-c][1,4]oxazine-2-carboxamide | Mixture of Diastereomers | ¹H NMR (400 MHz, CD₃OD) δ 7.37 (s, 5H), 7.02-6.96 (m, 2H), 6.18 (s, 1H), 5.80 (s, 1H), 4.53 (dd, J = 8.0, 11.6 Hz, 1H), 4.40-4.27 (m, 3H), 4.21-4.14 (m, 1H), 2.98-2.94 (m, 1H), 2.83-2.78 (m, 1H), 2.62-2.59 (m, 1H), 2.23-2.15 (m, 1H). | 439.1 1.838 min |
| Example #2 | 0.029 | 1-(2,2-difluoropropyl)-N-[(3S)-5-methyl-4-oxo-2,3-dihydro-1,5-benzoxazepin-3-yl]pyrazolo[4,3-c]pyridine-6-carboxamide | Single Known Stereoisomer | ¹H NMR (400 MHz, CD₃OD) δ 9.13 (s, 1H), 8.38 (s, 1H), 8.28 (s, 1H), 7.47-7.41 (m, 1H), 7.35-7.29 (m, 2H), 7.27-7.20 (m, 1H), 5.07-5.05 (m, 1H), 4.94 (t, J = 13.2 Hz, 2H), 4.70-4.66 (m, 1H), 4.42-4.39 (m, 1H), 3.44 (s, 3H), 1.65 (t, J = 18.8 Hz, 3H). | 416.1 1.858 min |
| Example #1 | | 1-cyclopropyl-N-[(3S)-5-methyl-4-oxo-2,3-dihydro-1,5-benzoxazepin-3-yl]pyrazolo[4,3-c]pyridine-6-carboxamide | Single Known Stereoisomer | ¹H NMR (400 MHz, CD₃OD) δ 9.10 (s, 1H), 8.34 (s, 1H), 8.26 (s, 1H), 7.49-7.42 (m, 1H), 7.38-7.30 (m, 2H), 7.27-7.23 (m, 1H), 5.10-5.05 (m, 1H), 4.74-4.67 (m, 1H), 4.45-4.42 (m, 1H), 3.79-3.76 (m, 1H), 3.44 (s, 3H), 1.24-1.21 (m, 4H). | 378.0 0.822 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #15 | 0.042 | (7S)-7-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide | Single Unknown Stereo-isomer | ¹H NMR (400 MHz, CD$_3$OD) δ 8.39 (d, J = 4.8 Hz, 1H), 7.85 (d, J = 8.0 Hz, 1H), 7.48 (dd, J = 4.8, 8.0 Hz, 1H), 7.39-7.25 (m, 2H), 7.22-7.08 (m, 2H), 4.77-4.69 (m, 1H), 4.55-4.49 (m, 1H), 4.45-4.35 (m, 1H), 4.34-4.24 (m, 1H), 3.41 (s, 3H), 3.20-3.09 (m, 1H), 2.95-2.88 (m, 1H), 2.78-2.57 (m, 2H), 2.33-2.24 (m, 1H). | 421.2 1.473 min |
| Example #17 | 0.037 | (7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide | Single Unknown Stereo-isomer | ¹H NMR (400 MHz, CD$_3$OD) δ 8.39 (d, J = 4.8 Hz, 1H), 7.84 (d, J = 8.0 Hz, 1H), 7.47 (dd, J = 4.0, 4.0 Hz, 1H), 7.39-7.32 (m, 2H), 7.31-7.25 (m, 3H), 4.56-4.48 (m, 2H), 4.43-4.36 (m, 1H), 4.30-4.22 (m, 1H), 3.40 (s, 3H), 3.29-3.22 (m, 1H), 3.18-3.08 (m, 1H), 2.95-2.87 (m, 1H), 2.67-2.58 (m, 2H), 2.33-2.21 (m, 1H). | 403.1 0.698 min |
| Example #18 | 0.044 | (5S)-5-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide | Single Unknown Stereo-isomer | ¹H NMR (400 MHz, CD$_3$OD) δ 8.37 (d, J = 4.0 Hz, 1H), 7.82 (d, J = 7.6 Hz, 1H), 7.47-7.45 (m, 1H), 7.40-7.31 (m, 3H), 7.21-7.19 (m, 2H), 5.55-5.50 (m, 1H), 4.52-4.47 (m, 1H), 3.40 (s, 3H), 3.26-3.20 (m, 1H), 3.17-3.09 (m, 2H), 3.08-3.00 (m, 1H), 2.91-2.90 (m, 1H), 2.70-2.56 (m, 2H), 2.30-2.21 (m, 1H). | 403.1 1.417 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #34 | 0.031 | 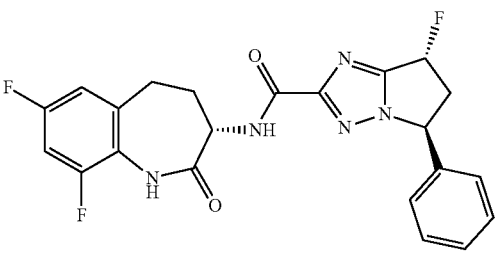 [SMILES: O=C(N[C@H]1CCc2cc(F)cc(F)c2NC1=O)c1nc2n(n1)[C@H](c1ccccc1)C[C@H]2F]<br>(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Single Unknown Stereo-isomer | ¹H NMR (400 MHz, CD₃OD) δ 7.41-7.38 (m, 3H), 7.28-7.25 (m, 2H), 7.02-6.97 (m, 2H), 6.26-6.24 (m, 0.5H), 6.12-6.10 (m, 0.5H), 5.86-5.82 (m, 1H), 4.59-4.54 (m, 1H), 3.46-3.36 (m, 1H), 2.99-2.96 (m, 1H), 2.84-2.82 (m, 1H), 2.81-2.78 (m, 1H), 2.66-2.62 (m, 1H), 2.24-2.18 (m, | 442.1 0.821 min |
| Example #35 | 0.015 | 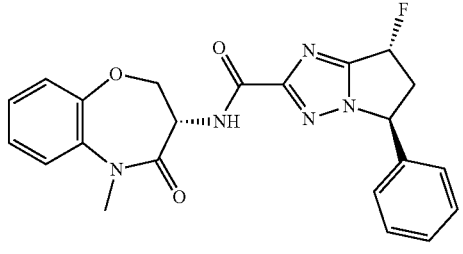 [SMILES: CN1C(=O)[C@@H](NC(=O)c2nc3n(n2)[C@H](c2ccccc2)C[C@H]3F)COc2ccccc21]<br>(5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereo-isomer | ¹H NMR (400 MHz, CD₃OD) δ 7.41-7.38 (m, 4H), 7.32-7.23 (m, 5H), 6.26-6.24 (m, 0.5H), 6.12-6.10 (m, 0.5H), 5.86-5.82 (m, 1H), 5.03-4.97 (m, 1H), 4.61-4.56 (m, 1H), 4.42-4.39 (m, 1H), 3.43-3.35 (m, 4H), 3.17-3.06 (m, 1H). | 422.1 0.849 min |
| Example #37 | 0.030 | 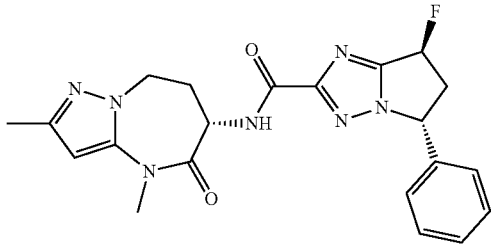 [SMILES: Cc1cc2n(n1)CC[C@H](NC(=O)c1nc3n(n1)[C@@H](c1ccccc1)C[C@@H]3F)C(=O)N2C]<br>(5R,7S)-7-fluoro-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | ¹H NMR (400 MHz, CD₃OD) δ 7.41-7.38 (m, 3H), 7.28-7.25 (m, 2H), 6.26-6.24 (m, 0.5H), 6.12-6.10 (m, 1.5H), 5.86-5.82 (m, 1H), 4.51-4.48 (m, 1H), 4.31-4.27 (m, 1H), 4.24-4.20 (m, 1H), 3.50-3.42 (m, 1H), 3.31 (s, 3H), 3.17-3.09 (m, 1H), 2.84-2.79 (m, 1H), 2.29-2.20 (m, 4H). | 424.1 0.783 min |

TABLE 1-continued

| Compound Example # | RIP1 Ki (μM) | Structure and Name | Stereo-chemistry | $^1$H NMR Data | MS (m/z) R.T. |
|---|---|---|---|---|---|
| Example #36 | 0.032 | 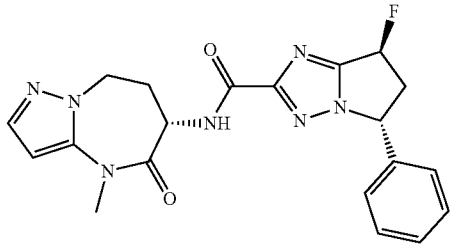 [SMILES: CN1C(=O)[C@@H](NC(=O)c2nc3n(n2)[C@@H](c2ccccc2)C[C@@H]3F)CCn2nccc21]<br>(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | $^1$H NMR (400 MHz, CD$_3$OD) δ 7.51 (d, J = 2.0 Hz, 1H), 7.45-7.38 (m, 3H), 7.35-7.25 (m, 2H), 6.29 (d, J = 2.4 Hz, 1H), 6.26-6.23 (m, 0.5H), 6.12-6.10 (m, 0.5H), 5.85-5.83 (m, 1H), 4.52-4.46 (m, 1H), 4.46-4.38 (m, 1H), 4.33-4.20 (m, 1H), 3.48-3.32 (m, 1H), 3.31 (s, 3H), 3.19-3.04 (m, 1H), 2.88-2.72 (m, 1H), 2.98-2.26 (m, 1H). | 410.1 0.765 min |
| Example #6 | 0.009 | 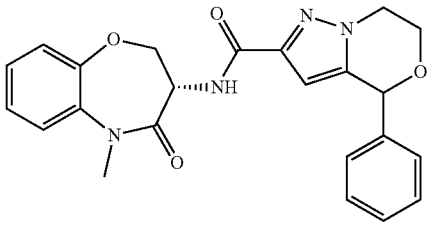 [SMILES: CN1C(=O)[C@@H](NC(=O)c2cc3n(n2)CCOC3c2ccccc2)COc2ccccc21]<br>4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide | Mixture of Diastereomers | $^1$H NMR (400 MHz, CD$_3$OD) δ 7.40-7.37 (m, 1H), 7.34 (s, 5H), 7.29-7.25 (m, 2H), 7.20-7.17 (m, 1H), 6.15 (s, 1H), 5.77 (s, 1H), 4.54-4.50 (m, 1H), 4.37-4.33 (m, 2H), 4.31-4.21 (m, 2H), 4.21-4.08 (m, 2H), 3.37 (s, 3H). | 419.1 1.889 min |
| Example #24 | 0.022 | 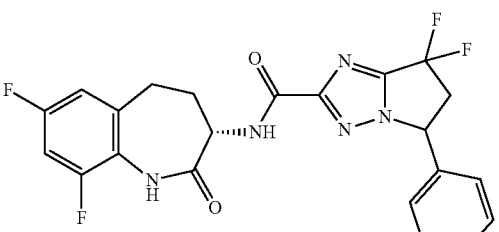<br>7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide | Mixture of Diastereomers | $^1$H NMR (400 MHz, CD$_3$OD) δ 7.42-7.38 (m, 3H), 7.27-7.25 (m, 2H), 7.02-6.97 (m, 2H), 5.57-5.53 (m, 1H), 5.02-5.97 (m, 1H), 3.88-3.80 (m, 1H), 3.30-3.20 (m, 1H), 2.98-2.96 (m, 1H), 2.84-2.80 (m, 1H), 2.65-2.61 (m, 1H), 2.26-2.23 (m, 1H). | 460.1 0.736 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #25 | 0.033 | 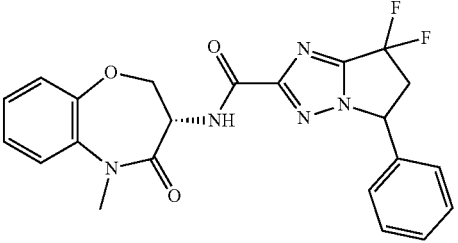 [SMILES: CN1C(=O)[C@@H](NC(=O)c2nc3n(n2)C(c2ccccc2)CC3(F)F)COc2ccccc21]<br>7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide | Mixture of Diastereomers | ¹H NMR (400 MHz, CD₃OD) δ 7.44-7.41 (m, 4H), 7.31-7.21 (m, 5H), 5.91-5.87 (m, 1H), 5.02-5.97 (m, 1H), 4.57-4.54 (m, 1H), 4.47-4.44 (m, 1H), 3.87-3.81 (m, 2H), 3.41 (s, 3H). | 440.1 0.749 min |
| Example #27 | 0.014 | 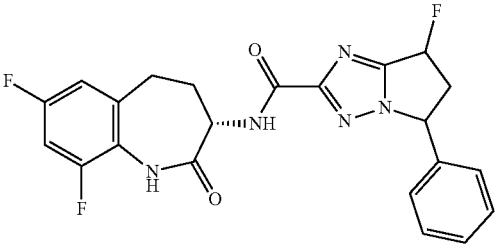 [SMILES: O=C(N[C@H]1CCc2cc(F)cc(F)c2NC1=O)c1nc2n(n1)C(c1ccccc1)CC2F]<br>7-fluoro-5-phenyl-N-[rac-(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Mixture of Diastereomers | ¹H NMR (400 MHz, CD₃OD) δ 7.41-7.38 (m, 3H), 7.28-7.25 (m, 2H), 7.02-7.25 (m, 2H), 6.26-6.24 (m, 0.5H), 6.12-6.10 (m, 0.5H), 5.86-5.82 (m, 1H), 4.59-4.54 (m, 1H), 3.46-3.36 (m, 1H), 2.99-2.96 (m, 1H), 2.84-2.82 (m, 1H), 2.81-2.78 (m, 1H), 2.66-2.62 (m, 1H), 2.24-2.18 (m, 1H). | 442.1 0.832 min |
| Example #28 | 0.012 | 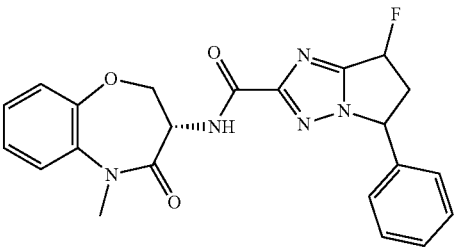 [SMILES: CN1C(=O)[C@@H](NC(=O)c2nc3n(n2)C(c2ccccc2)CC3F)COc2ccccc21]<br>7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | ¹H NMR (400 MHz, CD₃OD) δ 7.41-7.38 (m, 4H), 7.32-7.23 (m, 5H), 6.26-6.24 (m, 0.5H), 6.12-6.10 (m, 0.5H), 5.86-5.82 (m, 1H), 5.03-4.97 (m, 1H), 4.61-4.56 (m, 1H), 4.42-4.39 (m, 1H), 3.43-3.35 (m, 4H), 3.17-3.06 (m, 1H). | 422.1 0.855 min |

TABLE 1-continued

| Compound Example # | RIP1 Ki (μM) | Structure and Name | Stereo-chemistry | $^1$H NMR Data | MS (m/z) R.T. |
|---|---|---|---|---|---|
| Example #26 | 0.049 | 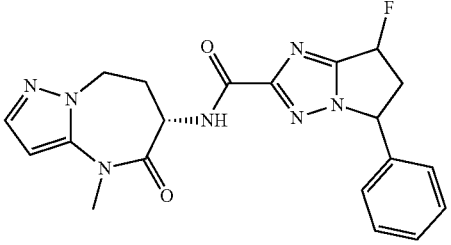 [SMILES: CN1C(=O)[C@@H](NC(=O)c2nc3n(n2)C(c2ccccc2)CC3F)CCn2nccc21]<br>7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Mixture of Diastereomers | $^1$H NMR (400 MHz, CD$_3$OD) δ 7.52 (d, J = 4.0 Hz, 1H), 7.41-7.39 (m, 3H), 7.28-7.25 (m, 2H), 6.30 (d, J = 2.0 Hz, 1H), 6.26-6.24 (m, 0.5H), 6.12-6.10 (m, 0.5H), 5.85-5.82 (m, 1H), 5.51-4.48 (m, 1H), 4.43-4.39 (m, 1H), 4.31-4.25 (m, 1H), 3.41-3.35 (m, 1H), 3.31 (s, 3H), 3.17-3.09 (m, 1H), 2.84-2.79 (m, 1H), 2.30-2.25 (m, 1H). | 410.0 0.763 min |
| Example #7 | 0.022 | 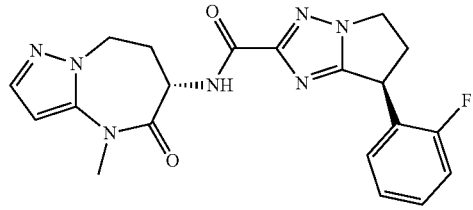 [SMILES: CN1C(=O)[C@@H](NC(=O)c2nc3n(n2)CC[C@H]3c2ccccc2F)CCn2nccc21]<br>(7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | $^1$H NMR (400 MHz, CD$_3$OD) δ 7.51 (s, 1H), 7.35-7.27 (m, 2H), 7.19-7.15 (m, 2H), 6.29 (d, J = 2.0 Hz, 1H), 4.75-4.72 (m, 1H), 4.52-4.47 (m, 1H), 4.43-4.30 (m, 2H), 4.28-4.20 (m, 2H), 3.31 (s, 3H), 2.88-2.74 (m, 2H), 2.70-2.65 (m, 1H), 2.28-2.24 (m, 1H). | 410.0 0.758 min |
| Example #8 | 0.018 | 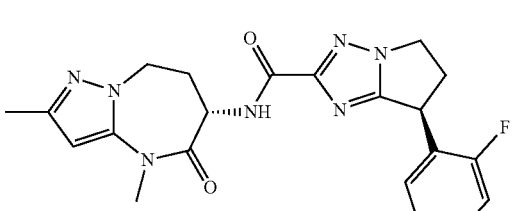<br>(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | $^1$H NMR (400 MHz, CD$_3$OD) δ 7.39-7.26 (m, 2H), 7.20-7.10 (m, 2H), 6.11 (s, 1H), 4.77-4.69 (m, 1H), 4.56-4.49 (m, 1H), 4.46-4.37 (m, 1H), 4.35-4.26 (m, 2H), 4.25-4.15 (m, 1H), 3.32 (s, 3H), 2.91-2.64 (m, 3H), 2.30-2.19 (m, 4H). | 424.1 0.764 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #21 | 0.026 | 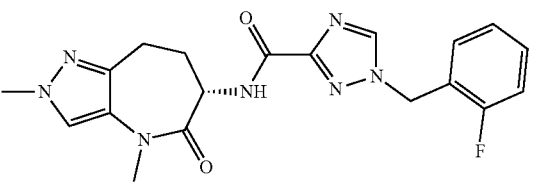 [SMILES: CN1C(=O)[C@@H](NC(=O)c2ncn(Cc3ccccc3F)n2)CCc2nn(C)cc21]<br>1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide | Single Unknown Stereo-isomer | ¹H NMR (400 MHz, CD₃OD) δ 8.84 (s, 1H), 7.88 (s, 1H), 7.42-7.40 (m, 2H), 7.23-7.16 (m, 2H), 5.59 (s, 2H), 4.72-4.68 (m, 1H), 3.93 (s, 3H), 3.32 (s, 3H), 3.06-2.89 (m, 2H), 2.53-2.43 (m, 1H), 2.32-2.21 (m, 1H). | 398.3 1.095 min |
| Example #20 | 0.046 | 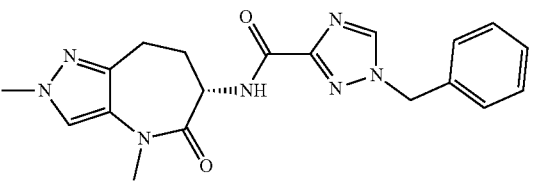 [SMILES: CN1C(=O)[C@@H](NC(=O)c2ncn(Cc3ccccc3)n2)CCc2nn(C)cc21]<br>1-benzyl-N-[(6S)-2,4-dimethyl-5-oxo-7,8-dihydro-6H-pyrazolo[4,3-b]azepin-6-yl]-1,2,4-triazole-3-carboxamide | Single Unknown Stereo-isomer | ¹H NMR (400 MHz, CD₃OD) δ 8.81 (s, 1H), 7.84 (s, 1H), 7.38-7.33 (m, 5H), 5.51 (s, 2H), 4.73-4.68 (m, 1H), 3.93 (s, 3H), 3.31 (s, 3H), 3.00-2.90 (m, 2H), 2.50-2.45 (m, 1H), 2.27-2.22 (m, 1H). | 380.2 1.088 min |
| Example #23 | 0.013 | 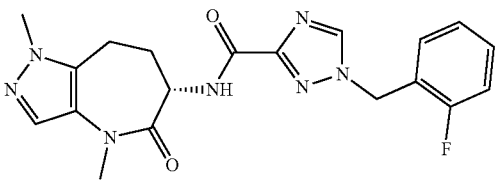 [SMILES: CN1C(=O)[C@@H](NC(=O)c2ncn(Cc3ccccc3F)n2)CCc2c1cnn2C]<br>1-[(2-fluorophenyl)methyl]-N-[(6S)-1,4-dimethyl-5-oxo-7,8-dihydro-6H-pyrazolo[4,3-b]azepin-6-yl]-1,2,4-triazole-3-carboxamide | Single Unknown Stereo-isomer | ¹H NMR (400 MHz, CD₃OD) δ 8.57 (s, 1H), 7.48 (s, 1H), 7.37 (t, J = 6.8 Hz, 2H), 7.22-7.09 (m, 2H), 5.54 (s, 2H), 4.59-4.55 (m, 1H), 3.77 (s, 3H), 3.33 (s, 3H), 3.18-3.07 (m, 1H), 2.97-2.86 (m, 1H), 2.47-2.36 (m, 1H), 2.23-2.10 (m, 1H). | 398.1 1.433 min |
| Example #22 | 0.014 | 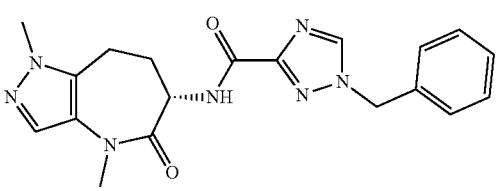 [SMILES: CN1C(=O)[C@@H](NC(=O)c2ncn(Cc3ccccc3)n2)CCc2c1cnn2C]<br>1-benzyl-N-[(6S)-1,4-dimethyl-5-oxo-7,8-dihydro-6H-pyrazolo[4,3-b]azepin-6-yl]-1,2,4-triazole-3-carboxamide | Single Unknown Stereo-isomer | ¹H NMR (400 MHz, CD₃OD) δ 8.56 (s, 1H), 7.48 (s, 1H), 7.35-7.31 (m, 5H), 5.46 (s, 2H), 4.59-4.55 (m, 1H), 3.77 (s, 3H), 3.28 (s, 3H), 3.13-3.10 (m, 1H), 2.95-2.92 (m, 1H), 2.41-2.40 (m, 1H), 2.19-2.16 (m, 1H). | 380.2 1.875 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #19 | 0.016 | 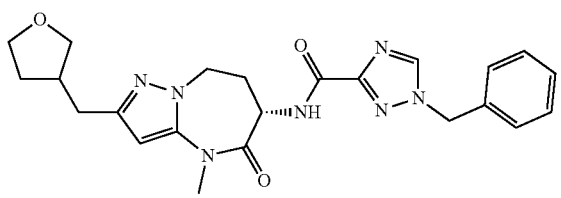 [SMILES: CN1C(=O)[C@@H](NC(=O)c2ncn(Cc3ccccc3)n2)CCn2nc(CC3CCOC3)cc21]<br>1-benzyl-N-[rac-(6S)-4-methyl-5-oxo-2-(tetrahydrofuran-3-ylmethyl)-7,8-dihydro-6H-pyrazolo[1,5-a][1,3]diazepin-6-yl]-1,2,4-triazole-3-carboxamide | Mixture of Diastereomers | ¹H NMR (400 MHz, CD₃OD) δ 8.56 (s, 1H), 7.38-7.32 (m, 5H), 6.17 (s, 1H), 5.47 (s, 2H), 4.53-4.49 (m, 1H), 4.37-4.30 (m, 1H), 4.26-4.18 (m, 1H), 3.91-3.84 (m, 2H), 3.79-3.72 (m, 1H), 3.50-3.46 (m, 1H), 3.33 (s, 3H), 2.87-2.81 (m, 1H), 2.71-2.66 (m, 2H), 2.63-2.56 (m, 1H), 2.30-2.21 (m, 1H), 2.12-2.05 (m, 1H), 1.70-1.66 (m, 1H). | 450.2 1.486 min |
| Example #38 SFC 1 | 0.024 | 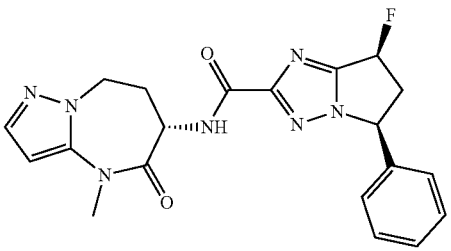 [SMILES: CN1C(=O)[C@@H](NC(=O)c2nc3n(n2)[C@H](c2ccccc2)C[C@@H]3F)CCn2nccc21]<br>rac-(5S,7S)-7-fluoro-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | ¹H NMR (400 MHz, DMSO-d₆) δ 8.75-8.59 (m, 1H), 7.61-7.10 (m, 6H), 6.39-6.23 (m, 1H), 6.20-6.00 (m, 1H), 5.81-5.50 (m, 1H), 4.51-3.95 (m, 3H), 3.93-3.53 (m, 1H), 3.24 (s, 3H), 2.80-2.52 (m, 1H), 2.47-2.12 (m, 1H). | 410.2 3.95 min |
| Example #39 SFC 2 | 0.027 | 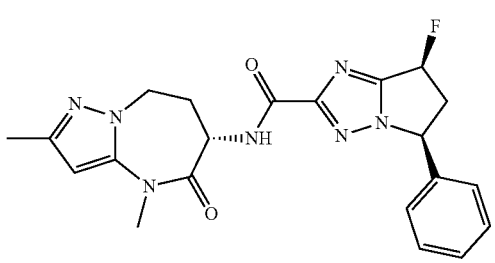 [SMILES: Cc1cc2n(n1)CC[C@H](NC(=O)c1nc3n(n1)[C@H](c1ccccc1)C[C@@H]3F)C(=O)N2C]<br>rac-(5S,7S)-7-fluoro-5-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereo-isomer | ¹H NMR (400 MHz, DMSO-d6) δ 8.67 (d, J = 7.9 Hz. 1H), 7.50-7.31 (m, 2H), 7.30-7.17 (m, 2H), 6.29 (d, J = 5.4 Hz, 1H), 6.18-6.03 (m, 1H), 5.79-5.58 (m, 1H), 4.45-4.18 (m, 2H), 4.17-3.96 (m, 1H), 3.84-3.55 (m, 1H), 3.21 (s, 3H), 2.67 (d, J = 1.9 Hz, 1H), 2.43-2.24 (m, 1H), 2.16 (s, 3H), 2.07 (s, 1H). | 424.2 4.14 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #40 SFC 3 | 0.005 | 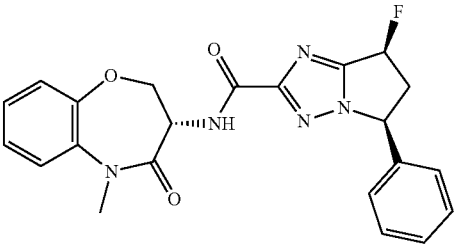 [SMILES: CN1C(=O)[C@@H](NC(=O)c2nc3n(n2)[C@H](c2ccccc2)C[C@@H]3F)COc2ccccc21]<br>rac-(5S,7S)-7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereo-isomer | 1H NMR (400 MHz, DMSO-d6) δ 8.61 (d, J = 8.1 Hz, 1H), 7.53-7.16 (m, 8H), 6.36-6.07 (m, 1H), 5.80-5.55 (m, 1H), 5.00-4.75 (m, 1H), 4.61 (dd, J = 11.6, 9.9 Hz, 1H), 4.39 (dd, J = 9.9, 7.7 Hz, 1H), 3.74 (d, J = 25.4 Hz, 1H), 2.86-2.58 (m, 1H). | 422.1 4.90 min |
| Example #41 SFC 4 | 0.035 | 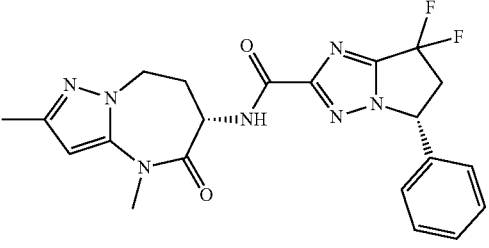 [SMILES: Cc1cc2n(n1)CC[C@H](NC(=O)c1nc3n(n1)[C@@H](c1ccccc1)CC3(F)F)C(=O)N2C]<br>rac-(5R)-7,7-difluoro-5-phenyl-N-[rac-(6S)-2,4-dimethyl-5-oxo-7,8-dihydro-6H-pyrazolo[1,5-a][1,3]diazepin-6-yl]-5,6-dihydropyrrolo[1,2-b][1,2,4]triazole-2-carboxamide | Single Unknown Stereo-isomer | | 442.1 4.79 min |
| Example #42 SFC 5 | 0.005 | 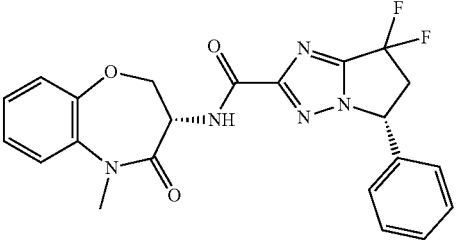 [SMILES: CN1C(=O)[C@@H](NC(=O)c2nc3n(n2)[C@@H](c2ccccc2)CC3(F)F)COc2ccccc21]<br>rac-(5R)-7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide | Single Unknown Stereo-isomer | 1H NMR (400 MHz, DMSO-d6) δ 9.92 (s, 1H), 8.58 (d, J = 7.6 Hz, 1H), 7.50-7.38 (m, 3H), 7.34-7.20 (m, 3H), 7.13 (s, 1H), 6.10-5.91 (m, 1H), 4.51-4.22 (m, 1H), 3.99-3.80 (m, 1H), 2.94-2.61 (m, 2H), 2.43-2.16 (m, 2H). | 440.1 5.58 min |

TABLE 1-continued

| Compound Example # | RIP1 Ki (μM) | Structure and Name | Stereo-chemistry | ¹H NMR Data | MS (m/z) R.T. |
|---|---|---|---|---|---|
| Example #43 SFC 6 | 0.028 | 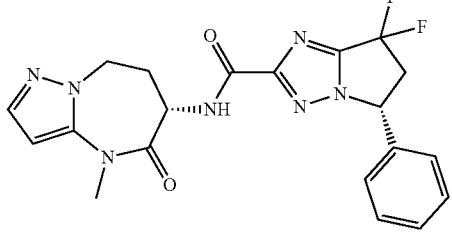<br>rac-(5R)-7,7-difluoro-5-phenyl-N-[rac-(6S)-4-methyl-5-oxo-7,8-dihydro-6H-pyrazolo[1,5-a][1,3]diazepin-6-yl]-5,6-dihydropyrrolo[1,2-b][1,2,4]triazole-2-carboxamide | Single Unknown Stereo-isomer | | 428.1 4.48 min |
| Example #44 SFC 7 | 0.007 | 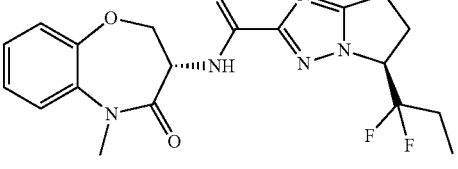<br>5-(1,1-difluoropropyl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereo-isomer | 1H NMR (400 MHz, DMSO-d6) δ 8.46 (d, J = 8.0 Hz, 1H), 7.58-7.41 (m, 1H), 7.44-7.17 (m, 3H), 4.98 (dd, J = 14.8, 8.4 Hz, 1H), 4.84(dt, J = 11.4, 7.8 Hz, 1H), 4.57 (dd, J = 11.5, 9.9 Hz, 1H), 4.42 (dd, J = 9.9, 7.7 Hz. 1H), 3.32 (s, 3H), 3.02-2.84 (m, 3H), 2.79-2.63 (m, 1H), 2.26-1.92 (m, 2H), 1.01 (t, J = 7.5 Hz. 3H). | 406.1 4.66 min |

All of the U.S. patents, U.S. patent publications, U.S. patent applications, foreign patents, foreign patent applications and non-patent publications referred to in this specification are incorporated herein by reference in their entireties. Although the invention has been described in some detail to facilitate understanding, it will be apparent that certain changes and modifications may be practiced within the scope of the appended claims. The described embodiments are to be considered as illustrative and not restrictive, and the invention is not to be limited to the details given herein, but may be modified within the scope and equivalents of the appended claims.

The invention claimed is:

1. A compound selected from the group consisting of:

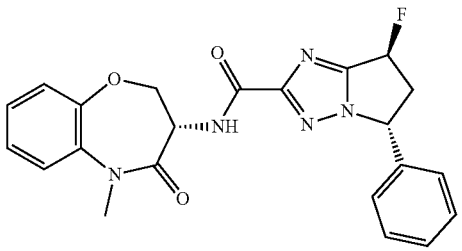 [SMILES: CN1C(=O)[C@@H](NC(=O)c2nc3n(n2)[C@@H](c2ccccc2)C[C@@H]3F)COc2ccccc21]

(5R)-5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

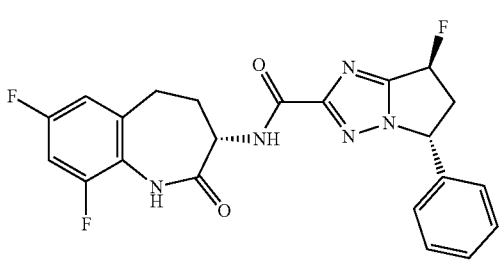 [SMILES: O=C(N[C@H]1CCc2cc(F)cc(F)c2NC1=O)c1nc2n(n1)[C@@H](c1ccccc1)C[C@@H]2F]

rac-(5R,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;

rac-(5R, 7S)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

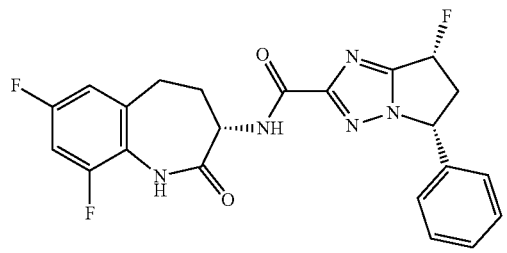

(5R,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

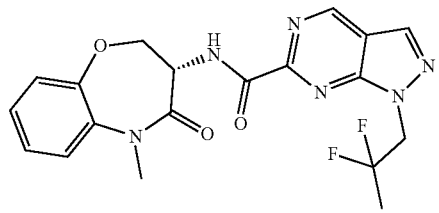 [SMILES: CN1C(=O)[C@@H](NC(=O)c2ncc3cnn(CC(C)(F)F)c3n2)COc2ccccc21]

1-(2,2-difluoropropyl)-N-[(3S)-5-methyl-4-oxo-2,3-dihydro-1,5-benzoxazepin-3-yl]pyrazolo[3,4-d]pyrimidine-6-carboxamide;

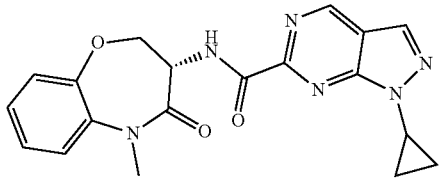 [SMILES: CN1C(=O)[C@@H](NC(=O)c2ncc3cnn(C4CC4)c3n2)COc2ccccc21]

1-cyclopropyl-N-[(3S)-5-methyl-4-oxo-2,3-dihydro-1,5-benzoxazepin-3-yl]pyrazolo [3,4-d]pyrimidine-6-carboxamide;

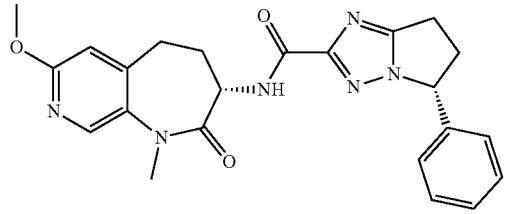 [SMILES: COc1cc2c(cn1)N(C)C(=O)[C@@H](NC(=O)c1nc3n(n1)[C@@H](c1ccccc1)CC3)CC2]

(5R)-5-phenyl-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;

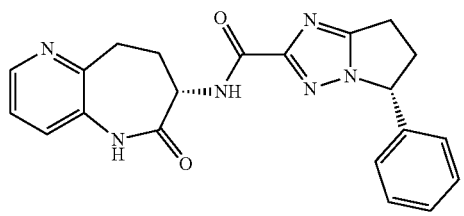 [SMILES: O=C(N[C@H]1CCc2ncccc2NC1=O)c1nc2n(n1)[C@@H](c1ccccc1)CC2]

(5R)-5-phenyl-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;

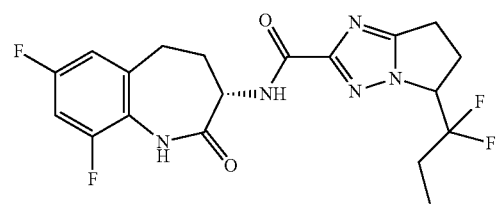 [SMILES: CCC(F)(F)C1CCc2nc(C(=O)N[C@H]3CCc4cc(F)cc(F)c4NC3=O)nn21]

5-(1,1-difluoropropyl)-N-[(3S)-7,9-difluoro-2-oxo-1,3,4,5-tetrahydro-1-benzazepin-3-yl]-6,7-dihydro-5H-pyrrolo[1,2-b][1,2,4]triazole-2carboxamide;

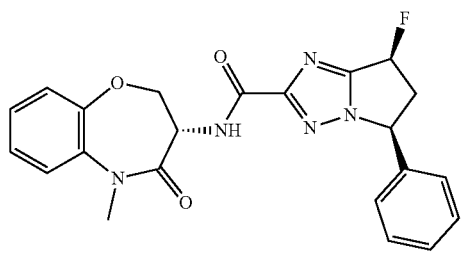 [SMILES: CN1C(=O)[C@@H](NC(=O)c2nc3n(n2)[C@H](c2ccccc2)C[C@@H]3F)COc2ccccc21]

rac-(5S,7S)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;

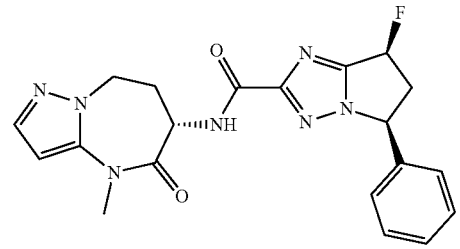 [SMILES: CN1C(=O)[C@@H](NC(=O)c2nc3n(n2)[C@H](c2ccccc2)C[C@@H]3F)CCn2nccc21]

rac-(5S,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

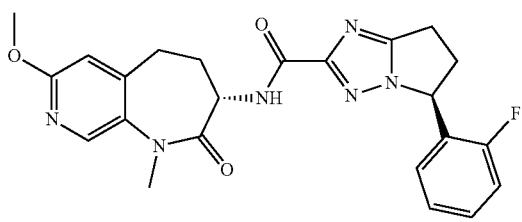 [SMILES: COc1cc2c(cn1)N(C)C(=O)[C@@H](NC(=O)c1nc3n(n1)[C@H](c1ccccc1F)CC3)CC2]

(5S)-5-(2-fluorophenyl)-N-[(3S)-7-methoxy-1-methyl-2-oxo-4,5-dihydro-3H-pyrido[3,4-b]azepin-3-yl]-6,7-dihydro-5H-pyrrolo[1,2-b][1,2,4]triazole-2-carboxamide;

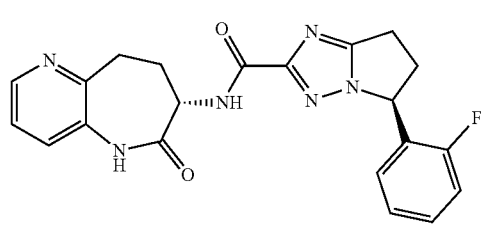 [SMILES: O=C(N[C@H]1CCc2ncccc2NC1=O)c1nc2n(n1)[C@H](c1ccccc1F)CC2]

(5S)-5-(2-fluorophenyl)-N-[(7S)-6-oxo-5,7,8,9-tetrahydropyrido[3,2-b]azepin-7-yl]-6,7-dihydro-5H-pyrrolo[1,2-b][1,2,4]triazole-2-carboxamide;

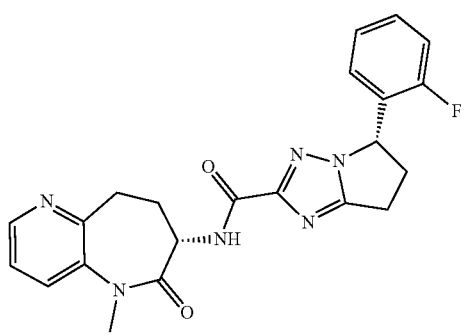 [SMILES: CN1C(=O)[C@@H](NC(=O)c2nc3n(n2)[C@H](c2ccccc2F)CC3)CCc2ncccc21]

(5R)-5-(2-fluorophenyl)-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2-carboxamide;

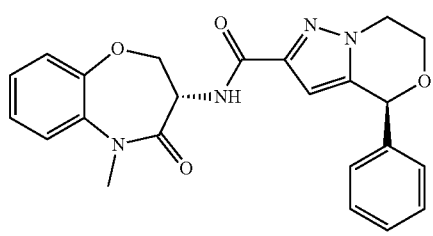 [SMILES: CN1C(=O)[C@@H](NC(=O)c2cc3n(n2)CCO[C@H]3c2ccccc2)COc2ccccc21]

(4S)-4-phenyl-N-[(3S)-5-methyl-4-oxo-2,3-dihydro-1,5-benzoxazepin-3-6,7-dihydro-4H-pyrazolo[5,1-c][1,4]oxazine-2-carboxamide;

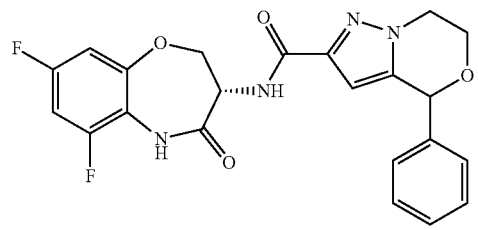

4-phenyl-N-[(3S)-7,9-difluoro-2-oxo-1,3,4,5-tetrahydro-1-benzazepin-3-6,7-dihydro-4H-pyrazolo[5,1-c][1,4]oxazine-2-carboxamide;

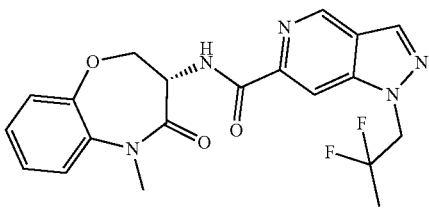 [SMILES: CN1C(=O)[C@@H](NC(=O)c2cc3c(cn2)cnn3CC(C)(F)F)COc2ccccc21]

1-(2,2-difluoropropyl)-N-[(3S)-5-methyl-4-oxo-2,3-dihydro-1,5-benzoxazepin-3-yl]pyrazolo[4,3-c]pyridine-6-carboxamide;

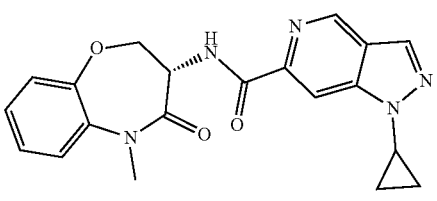 [SMILES: CN1C(=O)[C@@H](NC(=O)c2cc3c(cn2)cnn3C2CC2)COc2ccccc21]

1-cyclopropyl-N-[(3S)-5-methyl-4-oxo-2,3-dihydro-1,5-benzoxazepin-3-yl]pyrazolo[4,3-c]pyridine-6-carboxamide;

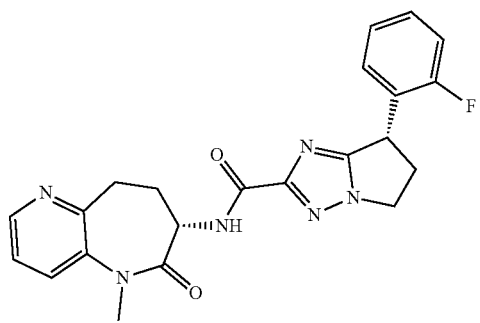 [SMILES: CN1C(=O)[C@@H](NC(=O)c2nc3n(n2)CC[C@H]3c2ccccc2F)CCc2ncccc21]

(7S)-7-(2-fluorophenyl)-N-[(7S)-5-methyl-6-oxo-8,9-dihydro-7H-pyrido[3,2-b]-azepin-7-yl]-6,7-dihydro-5H-pyrrolo[1,2-b][1,2,4]triazole-2-carboxamide;

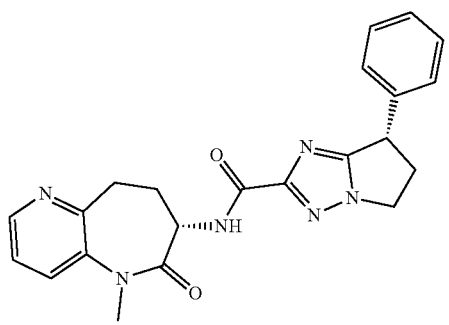 [SMILES: CN1C(=O)[C@@H](NC(=O)c2nc3n(n2)CC[C@H]3c2ccccc2)CCc2ncccc21]

(7S)-7-phenyl-N-[(7S)-5-methyl-6-oxo-8,9-dihydro-7H-pyrido[3,2-b]azepin-7-yl]-6,7-dihydro-5H-pyrrolo[1,2-b][1,2,4]triazole-2carboxamide;

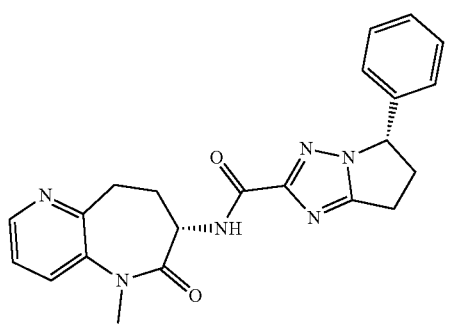 [SMILES: CN1C(=O)[C@@H](NC(=O)c2nc3n(n2)[C@H](c2ccccc2)CC3)CCc2ncccc21]

(5S)-5-phenyl-N-[(7S)-5-methyl-6-oxo-8,9-dihydro-7H-pyrido[3,2-b ]azepin-7-yl]-6,7-dihydro-5H-pyrrolo[1,2-b][1,2,4]triazole-2carboxamide;

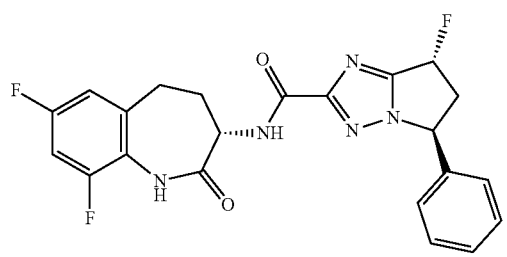 [SMILES: O=C(N[C@H]1CCc2cc(F)cc(F)c2NC1=O)c1nc2n(n1)[C@H](c1ccccc1)C[C@H]2F]

(5S,7R)-7-fluoro-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

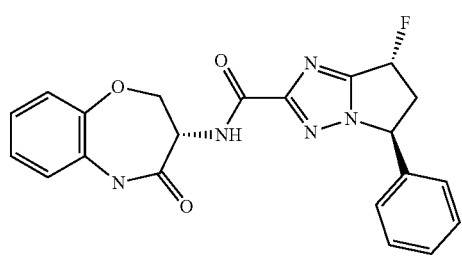 [SMILES: O=C(N[C@H]1COc2ccccc2NC1=O)c1nc2n(n1)[C@H](c1ccccc1)C[C@H]2F]

(5S,7R)-7-fluoro-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;

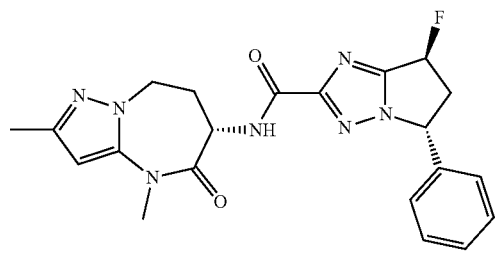 [SMILES: Cc1cc2n(n1)CC[C@H](NC(=O)c1nc3n(n1)[C@@H](c1ccccc1)C[C@@H]3F)C(=O)N2C]

(5R,7S)-7-fluoro-5-phenyl-N-[(6S)-2,4-dimethyl-5-oxo-7,8-dihydro-6H-pyrazolo [1,5-a][1,3]diazepin-6-yl]-6,7-dihydro-5H-pyrrolo[1,2-b][1,2,4]triazole-2-carboxamide;

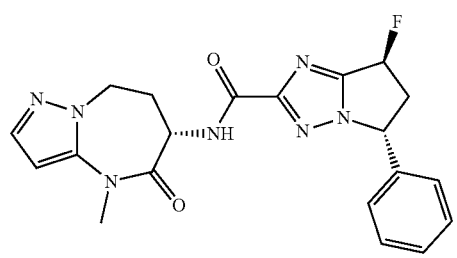 [SMILES: CN1C(=O)[C@@H](NC(=O)c2nc3n(n2)[C@@H](c2ccccc2)C[C@@H]3F)CCn2nccc21]

(5R,7S)-7-fluoro-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

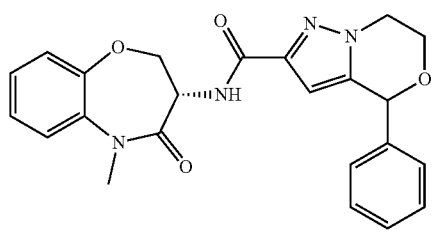 [SMILES: CN1C(=O)[C@@H](NC(=O)c2cc3n(n2)CCOC3c2ccccc2)COc2ccccc21]

4-phenyl-N-[(3S)-5-methyl-4-oxo-2,3-dihydro-1,5-benzoxazepin-3-yl]-6,7-dihydro-4H-pyrazolo[5,1-c][1,4]oxazine-2-carboxamide;

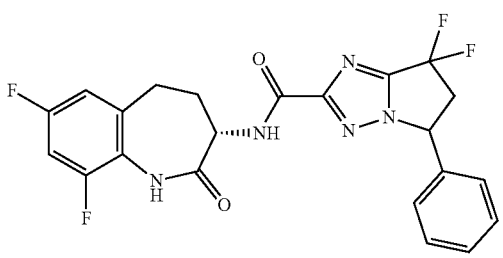 [SMILES: O=C(N[C@H]1CCc2cc(F)cc(F)c2NC1=O)c1nc2n(n1)C(c1ccccc1)CC2(F)F]

7,7-difluoro-5-phenyl-N-[(3S)-7,9-difluoro-2-oxo-1,3,4,5-tetrahydro-1-benzazepin-3-yl]-5,6-dihydropyrrolo[1,2-b][1,2,4]triazole-2-carboxamide;

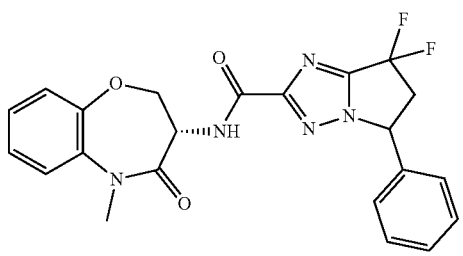 [SMILES: CN1C(=O)[C@@H](NC(=O)c2nc3n(n2)C(c2ccccc2)CC3(F)F)COc2ccccc21]

7,7-difluoro-5-phenyl-N-[rac-(3S)-5-methyl-4-oxo-2,3-dihydro-1,5-benzoxazepin-3-yl]-5,6-dihydropyrrolo[1,2-b][1,2,4]triazole-2-carboxamide;

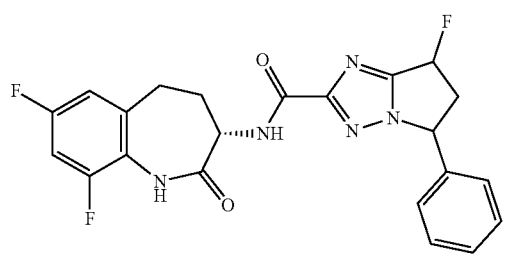 [SMILES: O=C(N[C@H]1CCc2cc(F)cc(F)c2NC1=O)c1nc2n(n1)C(c1ccccc1)CC2F]

7-fluoro-5-phenyl-N-[rac-(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide;

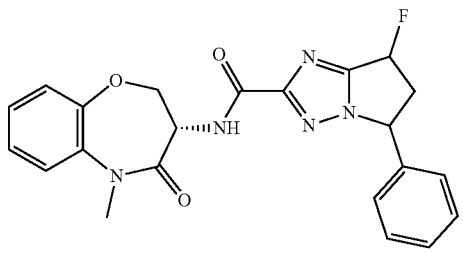 [SMILES: CN1C(=O)[C@@H](NC(=O)c2nc3n(n2)C(c2ccccc2)CC3F)COc2ccccc21]

7-fluoro-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide;

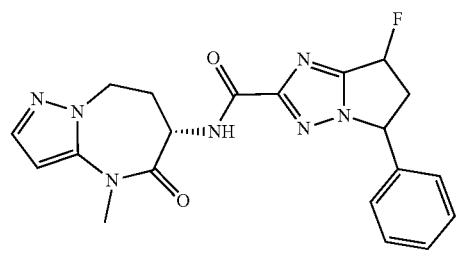 [SMILES: CN1C(=O)[C@@H](NC(=O)c2nc3n(n2)C(c2ccccc2)CC3F)CCn2nccc21]

7-fluoro-5-phenyl-N-[6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

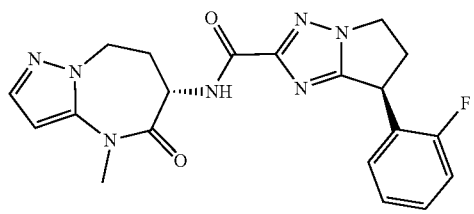 [SMILES: CN1C(=O)[C@@H](NC(=O)c2nc3n(n2)CC[C@H]3c2ccccc2F)CCn2nccc21]

(7S)-7-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

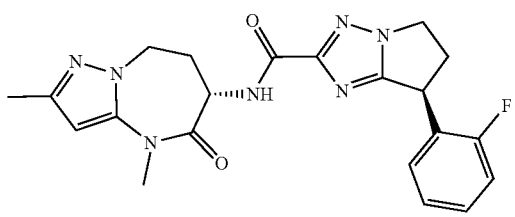 [SMILES: Cc1cc2n(n1)CC[C@H](NC(=O)c1nc3n(n1)CC[C@H]3c1ccccc1F)C(=O)N2C]

(7S)-7-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

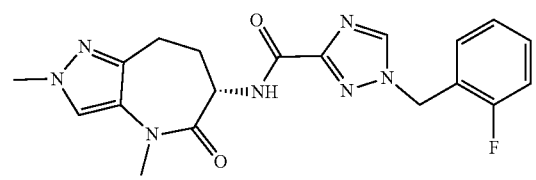 [SMILES: CN1C(=O)[C@@H](NC(=O)c2ncn(Cc3ccccc3F)n2)CCc2nn(C)cc21]

1-[(2-fluorophenyl)methyl]-N-[(6S)-2,4-dimethyl-5-oxo-7,8-dihydro-6H-pyrazolo[4,3-b]azepin-6-yl]-1,2,4-triazole-3-carboxamide;

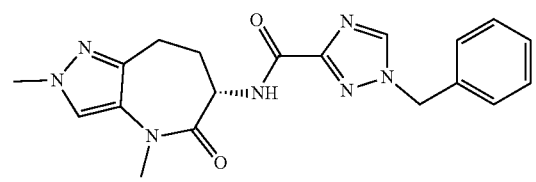 [SMILES: CN1C(=O)[C@@H](NC(=O)c2ncn(Cc3ccccc3)n2)CCc2nn(C)cc21]

1-benzyl-N-[(6S)-2,4-dimethyl-5-oxo-7,8-dihydro-6H-pyrazolo[4,3-b]azepin-6-yl]-1,2,4-triazole-3-carboxamide;

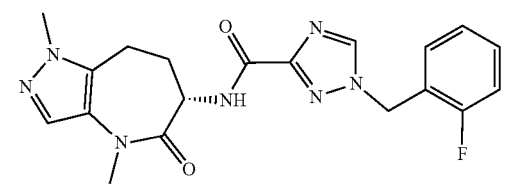 [SMILES: CN1C(=O)[C@@H](NC(=O)c2ncn(Cc3ccccc3F)n2)CCc2c1cnn2C]

1-[(2-fluorophenyl)methyl]-N-[6S]-1,4-dimethyl-5-oxo-
7,8-dihydro-6H-pyrazolo[4,3-b]azepin-6-yl]-1,2,4-tri-
azole-3-carboxamide;

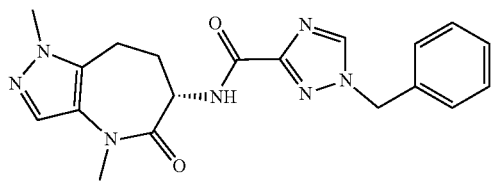 [SMILES: CN1C(=O)[C@@H](NC(=O)c2ncn(Cc3ccccc3)n2)CCc2c1cnn2C]

1-benzyl-N-[(6S)-1,4-dimethyl-5-oxo-7,8-dihydro-6H-
pyrazolo[4,3-b]azepin-6-yl]-1,2,4-triazole-3-carbox-
amide;

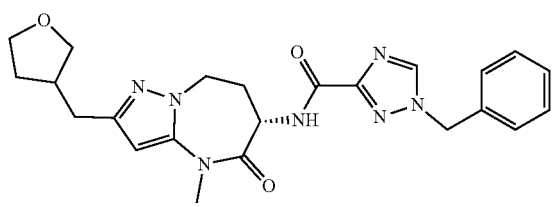 [SMILES: CN1C(=O)[C@@H](NC(=O)c2ncn(Cc3ccccc3)n2)CCn2nc(CC3CCOC3)cc21]

1-benzyl-N-[rac-(6S)-4-methyl-5-oxo-2-(tetrahydro-
furan-3-ylmethyl)-7,8-dihydro-6H-pyrazolo[1,5-a][1,
3]diazepin-6-yl]-1,2,4-triazole-3-carboxamide;

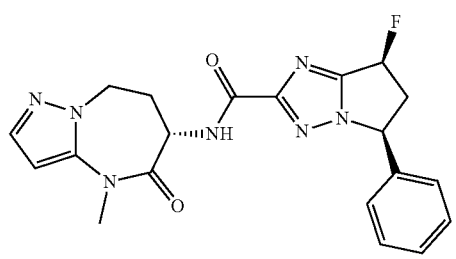 [SMILES: CN1C(=O)[C@@H](NC(=O)c2nc3n(n2)[C@H](c2ccccc2)C[C@@H]3F)CCn2nccc21]

rac-(5S,7S)-7-fluoro-5-phenyl-N-[rac-(6S)-4-methyl-5-
oxo-7,8-dihydro-6H-pyrazolo[1,5-a][1,3]diazepin-6-
yl]-6,7-dihydro-5H-pyrrolo[1,2-b][1,2,4]triazole-2-
carboxamide;

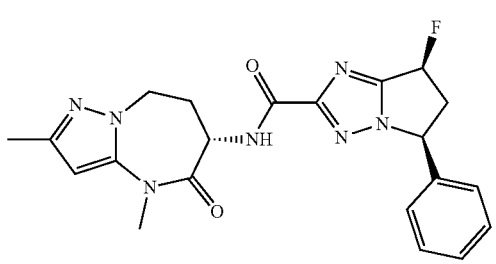 [SMILES: Cc1cc2n(n1)CC[C@H](NC(=O)c1nc3n(n1)[C@H](c1ccccc1)C[C@@H]3F)C(=O)N2C]

rac-(5S,7S)-7-fluoro-5-phenyl-N-[rac-(6S)-2,4-dimethyl-
5-oxo-7,8-dihydro-6H-pyrazolo[1,5-a][1,3]diazepin-6-
yl]-6,7-dihydro-5H-pyrrolo[1,2-b][1,2,4]triazole-2-
carboxamide;

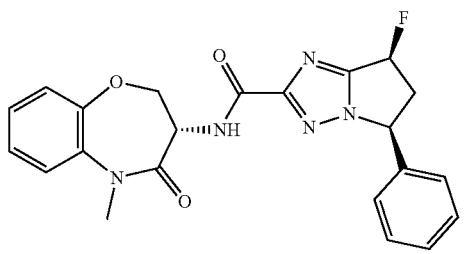 [SMILES: CN1C(=O)[C@@H](NC(=O)c2nc3n(n2)[C@H](c2ccccc2)C[C@@H]3F)COc2ccccc21]

rac-(5S,7S)-7-fluoro-5-phenyl-N-[rac-(3S)-5-methyl-4-
oxo-2,3-dihydro-1,5-benzoxazepin-3-yl]-6,7-dihydro-
5H-pyrrolo[1,2-b][1,2,4]triazole-2-carboxamide;

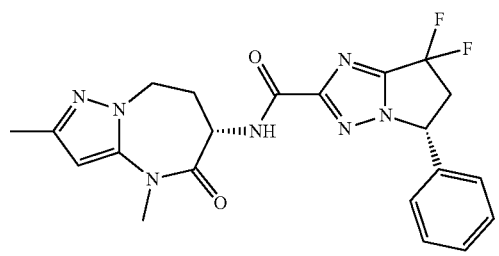 [SMILES: Cc1cc2n(n1)CC[C@H](NC(=O)c1nc3n(n1)[C@@H](c1ccccc1)CC3(F)F)C(=O)N2C]

rac-(5R)-7,7-difluoro-5-phenyl-N-[rac-(6S)-2,4-dim-
ethyl-5-oxo-7,8-dihydro-6H-pyrazolo[1,5-a][1,3]diaz-
epin-6-yl]-5,6-dihydropyrrolo[1,2-b][1,2,4]triazole-2-
carboxamide;

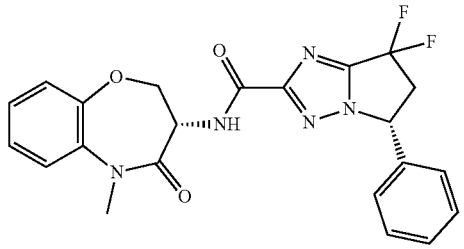 [SMILES: CN1C(=O)[C@@H](NC(=O)c2nc3n(n2)[C@@H](c2ccccc2)CC3(F)F)COc2ccccc21]

rac-(5R)-7,7-difluoro-5-phenyl-N-[rac-(3S)-5-methyl-4-
oxo-2,3-dihydro-1,5-benzoxazepin-3-yl]-5,6-dihydro-
pyrrolo[1,2-b][1,2,4]triazole-2-carboxamide;

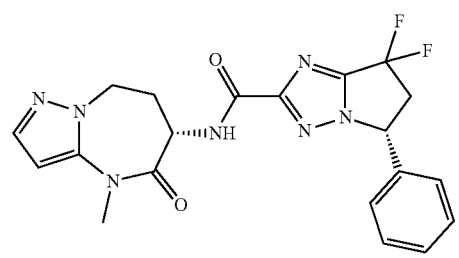 [SMILES: CN1C(=O)[C@@H](NC(=O)c2nc3n(n2)[C@@H](c2ccccc2)CC3(F)F)CCn2nccc21]

rac-(5R)-7,7-difluoro-5-phenyl-N-[rac-(6S)-4-methyl-5-
oxo-7,8-dihydro-6H-pyrazolo[1,5-a][1,3]diazepin-6-
yl]-5,6-dihydropyrrolo[1,2-b][1,2,4]triazole-2-carbox-
amide; and

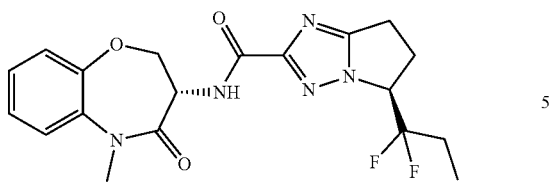

5-(1,1-difluoropropyl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide;
or an enantiomer thereof, or a pharmaceutically acceptable salt thereof.

2. A pharmaceutical composition comprising a compound of claim 1, or an enantiomer thereof, or a pharmaceutically acceptable salt thereof, and a therapeutically inert carrier.

3. A method for the treatment of a disease or disorder in a human, the method comprising administration to the human of an effective treatment amount of a compound of claim 1, or an enantiomer thereof, or a pharmaceutically acceptable salt thereof, wherein the disease or disorder is selected from the group consisting of irritable bowel disorder (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney disease, acute respiratory distress syndrome (ARDS) and chronic obstructive pulmonary disease (COPD).

* * * * *